United States Patent
Jung et al.

(10) Patent No.: US 11,563,184 B2
(45) Date of Patent: Jan. 24, 2023

(54) HETEROCYCLIC COMPOUND AND ORGANIC LIGHT EMITTING ELEMENT CONTAINING SAME

(71) Applicant: LG CHEM, LTD., Seoul (KR)

(72) Inventors: Min Woo Jung, Daejeon (KR); Dong Hoon Lee, Daejeon (KR); Jungoh Huh, Daejeon (KR); Seongmi Cho, Daejeon (KR); Jungha Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 435 days.

(21) Appl. No.: 16/629,216

(22) PCT Filed: Jul. 11, 2018

(86) PCT No.: PCT/KR2018/007842
§ 371 (c)(1),
(2) Date: Jan. 7, 2020

(87) PCT Pub. No.: WO2019/013542
PCT Pub. Date: Jan. 17, 2019

(65) Prior Publication Data
US 2020/0227646 A1 Jul. 16, 2020

(30) Foreign Application Priority Data

Jul. 11, 2017 (KR) .................. 10-2017-0087832

(51) Int. Cl.
*C07D 405/10* (2006.01)
*H01L 51/00* (2006.01)
*H01L 51/50* (2006.01)

(52) U.S. Cl.
CPC ........ *H01L 51/0067* (2013.01); *C07D 405/10* (2013.01); *H01L 51/0073* (2013.01);
(Continued)

(58) Field of Classification Search
None
See application file for complete search history.

(56) References Cited

U.S. PATENT DOCUMENTS

| | | | |
|---|---|---|---|
| 7,014,925 B2 * | 3/2006 | Thoms | H05B 33/14 313/506 |
| 2003/0168970 A1 * | 9/2003 | Tominaga | C07F 7/0814 556/415 |

(Continued)

FOREIGN PATENT DOCUMENTS

| | | |
|---|---|---|
| CN | 101440082 | 5/2009 |
| JP | 2009191232 | 8/2009 |

(Continued)

*Primary Examiner* — Robert S Loewe
(74) *Attorney, Agent, or Firm* — Dentons US LLP

(57) ABSTRACT

Provided is a heterocyclic compound of Chemical Formula 1:

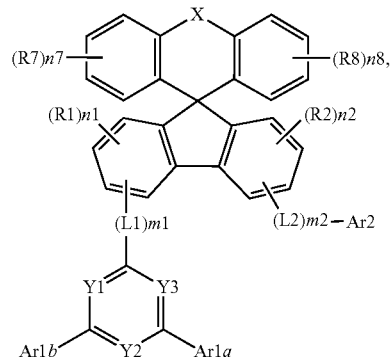

and an organic light emitting device including the same.

23 Claims, 1 Drawing Sheet

(52) U.S. Cl.
CPC ...... *H01L 51/5072* (2013.01); *H01L 51/5092* (2013.01); *H01L 51/5096* (2013.01)

(56) References Cited

U.S. PATENT DOCUMENTS

| | | |
|---|---|---|
| 2004/0251816 A1 | 12/2004 | Leo et al. |
| 2015/0115241 A1 | 4/2015 | Zoellner et al. |
| 2015/0295181 A1* | 10/2015 | Mujica-Fernaud .... H05B 33/20 252/500 |
| 2016/0118599 A1* | 4/2016 | Jeong .................. C07F 9/65586 546/276.7 |
| 2017/0222157 A1 | 8/2017 | Jatsch et al. |
| 2018/0248124 A1 | 8/2018 | Mujica-Fernaud et al. |
| 2019/0355915 A1* | 11/2019 | Heo ...................... C07D 413/04 |
| 2020/0223857 A1* | 7/2020 | He ....................... C07D 487/04 |

FOREIGN PATENT DOCUMENTS

| | | |
|---|---|---|
| KR | 10-20150083917 | 7/2015 |
| KR | 10-1593368 | 2/2016 |
| KR | 10-20170032414 | 3/2017 |

\* cited by examiner

【FIG. 1】
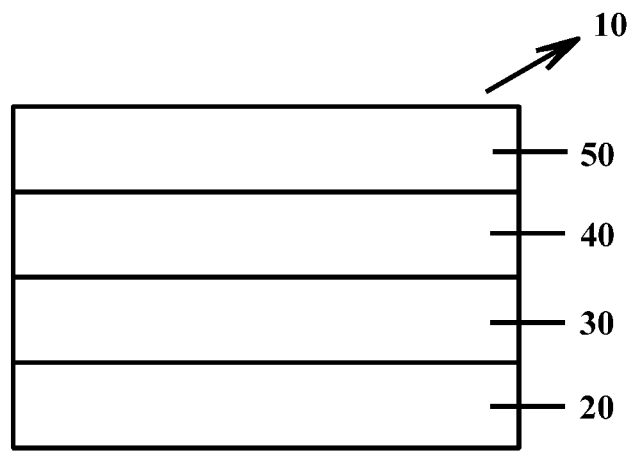
【FIG. 2】
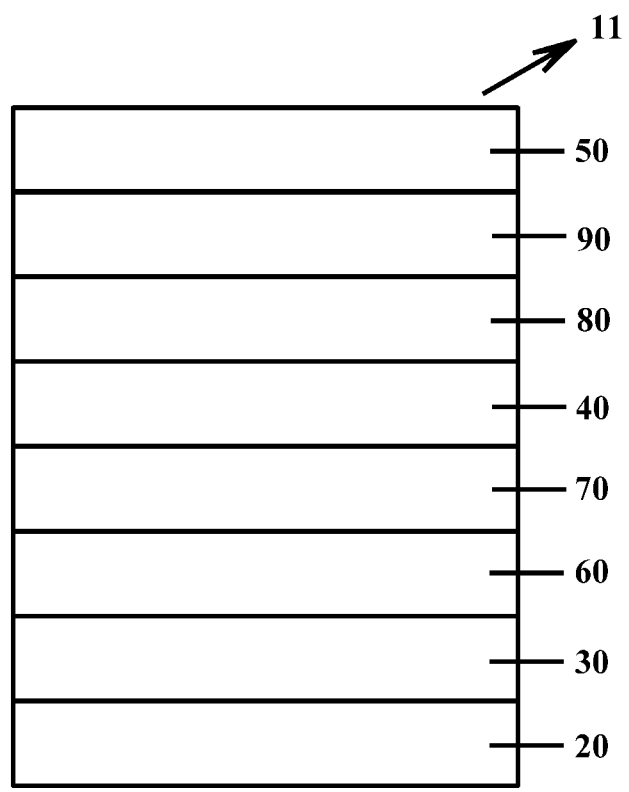

HETEROCYCLIC COMPOUND AND ORGANIC LIGHT EMITTING ELEMENT CONTAINING SAME

CROSS-REFERENCE TO RELATED APPLICATION(S)

This application is a National Stage Application of International Application No. PCT/KR2018/007842 filed on Jul. 11, 2018, which claims priority to and the benefits of Korean Patent Application No. 10-2017-0087832, filed with the Korean Intellectual Property Office on Jul. 11, 2017, the entire contents of which are incorporated herein by reference.

TECHNICAL FIELD

The present specification relates to a heterocyclic compound and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be famed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

US Patent Application Laid-Open Publication No. 2004-0251816

Technical Problem

The present specification is directed to providing a heterocyclic compound and an organic light emitting device including the same.

Technical Solution

One embodiment of the present specification provides a heterocyclic compound of Chemical Formula 1:

[Chemical Formula 1]

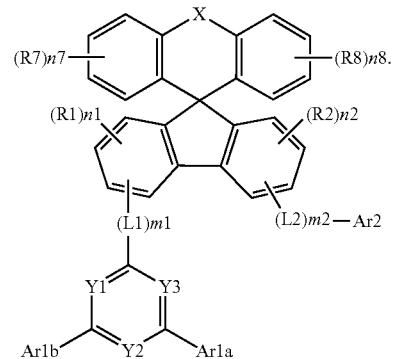

In Chemical Formula 1:

X is O or S;

Y1 to Y3 are the same as or different from each other and each independently is N or CR, and at least two of Y1 to Y3 are N;

Ar1a and Ar1b are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

Ar2 is an aryl group unsubstituted or substituted with an alkyl group;

L1 is a direct bond;

L2 is a direct bond or a substituted or unsubstituted arylene group;

R, R1, R2, R7 and R8 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and n1 and n2 are each independently an integer of 0 to 3, n7 and n8 are each independently an integer of 0 to 4, m1 and m2 are each independently an integer of 1 or 2; and when n1, n2, n7 and n8 are each an integer of 2 or greater, substituents in the parentheses are the same as or different from each other;

and when m1 and m2 are each an integer of 2 or greater, substituents in the parentheses are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the heterocyclic compound of Chemical Formula 1.

Advantageous Effects

A heterocyclic compound according to one embodiment of the present specification can be used as a material of an organic material layer of an organic light emitting device, and by using the same, efficiency can be enhanced, a low driving voltage can be obtained and/or lifetime properties can be enhanced in the organic light emitting device.

DESCRIPTION OF DRAWINGS

FIG. 1 illustrates an organic light emitting device (10) according to one embodiment of the present specification.

FIG. 2 illustrates an organic light emitting device (11) according to another embodiment of the present specification.

MODE FOR DISCLOSURE

Herein, the present specification will be described in more detail.

One embodiment of the present specification provides a heterocyclic compound of Chemical Formula 1.

The heterocyclic compound according to one embodiment of the present specification has a non-linear structure, and is capable of enhancing efficiency, obtaining a low driving voltage, and/or enhancing lifetime properties in an organic light emitting device.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a nitrile group, a nitro group, an imide group, an amide group, a carbonyl group, an ester group, a hydroxyl group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, and a substituted or unsubstituted heteroaryl group, or being substituted with a substituent linking two or more substituents among the substituents illustrated above, or having no substituents. For example, "a substituent linking two or more substituents" can include a biphenyl group. In other words, a biphenyl group can be an aryl group, or interpreted as a substituent linking two phenyl groups.

In the present specification, the number of carbon atoms of the imide group is not particularly limited, but is preferably from 1 to 30. Specifically, compounds having structures as below can be included, however, the imide group is not limited thereto:

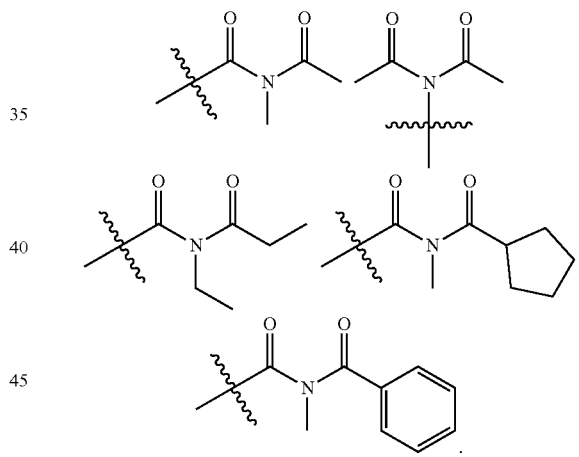

In the present specification, in the amide group, the nitrogen of the amide group can be substituted with a linear, branched or cyclic alkyl group having 1 to 30 carbon atoms or an aryl group having 6 to 30 carbon atoms. Specifically, compounds having the following structural formulae can be included, however, the amide group is not limited thereto:

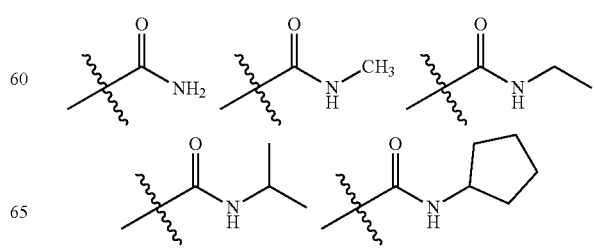

-continued

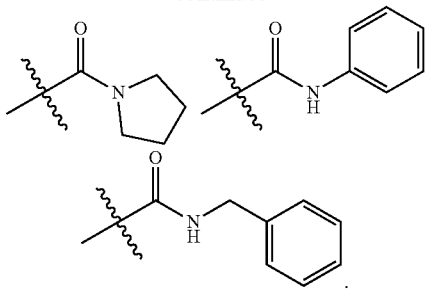

In the present specification, in the ester group, the oxygen of the ester group can be substituted with a linear, branched or cyclic alkyl group having 1 to 25 carbon atoms or an aryl group having 6 to 30 carbon atoms. Specifically, compounds having the following structural formulae can be included, however, the ester group is not limited thereto:

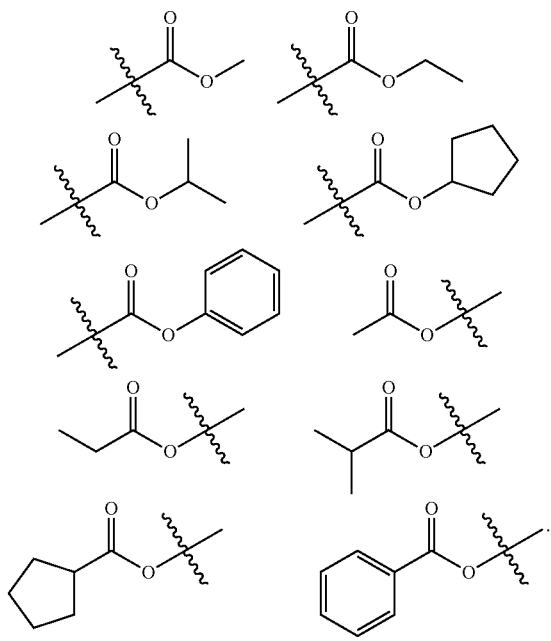

In the present specification, the alkyl group can be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof can include a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethylpropyl group, a 1,1-dimethylpropyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 30 carbon atoms and more preferably has 3 to 20 carbon atoms. Specific examples thereof can include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group can be linear, branched or cyclic. The number of carbon atoms of the alkoxy group is not particularly limited, but is preferably from 1 to 30. Specifically, the number of carbon atoms is preferably 1 to 20. More specifically, the number of carbon atoms is preferably 1 to 10. Specific examples thereof can include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, an 2-ethylbutyloxy group, an n-octyloxy group, an n-nonyloxy group, an n-decyloxy group, a benzyloxy group, a p-methylbenzyloxy group and the like, but are not limited thereto.

In the present specification, the amine group can be selected from the group consisting of —$NH_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30. Specific examples of the amine group can include a methylamine group, a dimethylamine group, an ethylamine group; a diethylamine group, a phenylamine group, a naphthylamine group, a biphenylamine group, an anthracenylamine group, a 9-methylanthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenyl-amine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group can include a methylthioxy group, an ethylthioxy group, a tert-butylthioxy group, a hexylthioxy group, an octylthioxy group and the like, and the alkylsulfoxy group can include mesyl, an ethylsulfoxy group, a propylsulfoxy group, a butylsulfoxy group and the like, however, the alkylthoixy group and the alkylsulfoxy group are not limited thereto.

In the present specification, the alkenyl group can be linear or branched, and although not particularly limited thereto, the number of carbon atoms is preferably from 2 to 30. More specifically, the number of carbon atoms is preferably from 2 to 20. Specific examples thereof can include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the silyl group can be a chemical formula of —SiRaRbRc, and Ra, Rb and Rc are the same as or different from each other, and each independently is hydrogen, a substituted or unsubstituted alkyl group, or a substituted or unsubstituted aryl group. Specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group can be —BR$_{100}$R$_{101}$, and R$_{100}$ and R$_{101}$ are the same as or different from each other, and can be each independently selected from the group consisting of hydrogen, deuterium, a halogen group, a nitrile group, a substituted or unsubstituted monocyclic or polycyclic cycloalkyl group having 3 to 30 carbon atoms, a substituted or unsubstituted linear or branched alkyl group having 1 to 30 carbon atoms, a substituted or unsubstituted monocyclic or polycyclic aryl group having 6 to 30 carbon atoms, and a substituted or unsubstituted monocyclic or polycyclic heteroaryl group having 2 to 30 carbon atoms.

In the present specification, specific examples of the phosphine oxide group can include a diphenylphosphine oxide group, a dinaphthylphosphine oxide group and the like, but are not limited thereto.

In the present specification, the aryl group is not particularly limited, but preferably has 6 to 30 carbon atoms, and more preferably has 6 to 20 carbon atoms. The aryl group can be monocyclic or polycyclic. When the aryl group is a monocyclic aryl group, the number of carbon atoms is not particularly limited, but is preferably from 6 to 30. More specifically, the number of carbon atoms is preferably from 6 to 20. Specific examples of the monocyclic aryl group can include a phenyl group, a biphenyl group, a terphenyl group and the like, but are not limited thereto. When the aryl group is a polycyclic aryl group, the number of carbon atoms is not particularly limited, but is preferably from 10 to 30, and more specifically, the number of carbon atoms is preferably from 10 to 20. Specific examples of the polycyclic aryl group can include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

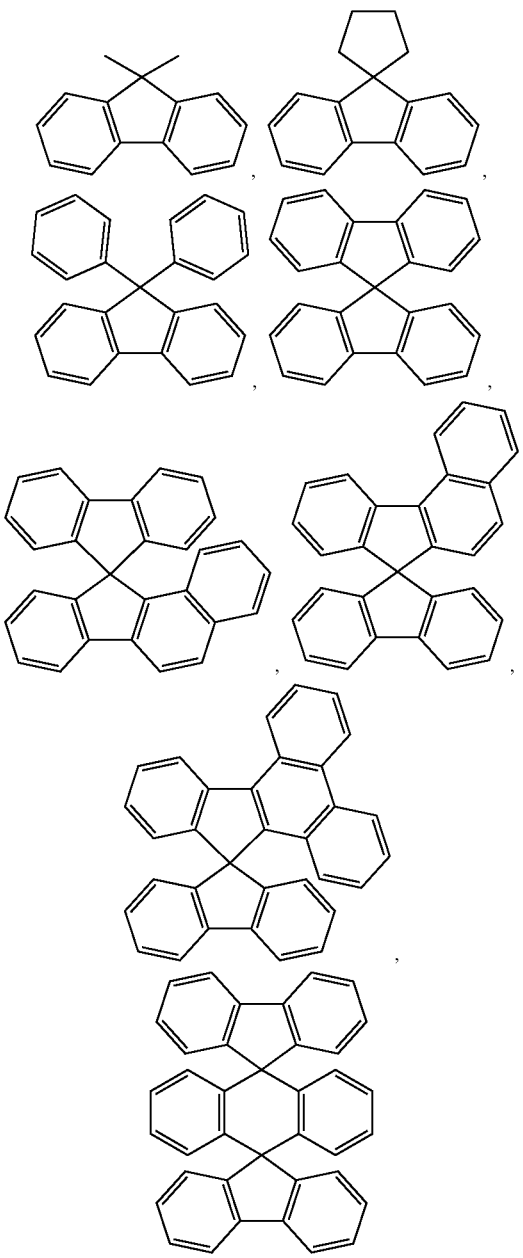

and the like can be included. However, the compound is not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group can include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like. Specific examples of the arylthioxy group can include a phenylthioxy group, a 2-methylphenylthioxy group, a 4-tert-butylphenylthioxy group and the like, and specific examples of the arylsulfoxy group can include a benzenesulfoxy group, a p-toluenesulfoxy group and the like. However, the aryloxy group, the arylthioxy group and the arylsulfoxy group are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30 and more preferably from 2 to 20, and the heteroaryl group can be monocyclic or polycyclic. Examples of the heteroaryl group can include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above can be applied thereto except for each being a divalent group.

In the present specification, the heteroarylene group means a heteroaryl group having two bonding sites, that is, a divalent group. Descriptions on the heteroaryl group provided above can be applied thereto except for each being a divalent group.

According to one embodiment of the present specification, Ar1a and Ar1b are the same as or different from each other, and each independently is hydrogen, deuterium, a nitrile group, a nitro group, a hydroxyl group, a carbonyl group, an ester group, an imide group, an amide group, a substituted or unsubstituted alkyl group having 1 to 30 carbon atoms, a substituted or unsubstituted cycloalkyl group having 3 to 30 carbon atoms, a substituted or unsubstituted alkoxy group having 1 to 30 carbon atoms, a substituted or unsubstituted alkenyl group having 2 to 30 carbon atoms, a substituted or unsubstituted silyl group, a substituted or unsubstituted amine group, a substituted or unsubstituted aryl group having 6 to 30 carbon atoms, or a substituted or unsubstituted heteroaryl group having 2 to 30 carbon atoms.

According to one embodiment of the present specification, Ar1a and Ar1b are the same as or different from each other, and each independently a substituted or unsubstituted aryl group having 6 to 30 carbon atoms or a substituted or unsubstituted heteroaryl group having 2 to 30 carbon atoms.

According to one embodiment of the present specification, Ar1a and Ar1b are the same as or different from each other, and each independently an aryl group unsubstituted or substituted with an alkyl group, an aryl group or a heteroaryl group, or a heteroaryl group unsubstituted or substituted with an aryl group or a heteroaryl group.

According to one embodiment of the present specification, Ar1a and Ar1b are the same as or different from each other, and each independently is a substituted or unsubstituted phenyl group, a biphenyl group, a terphenyl group, a substituted or unsubstituted fluorene group, a substituted or unsubstituted dibenzofuran group, a substituted or unsubstituted dibenzothiophene group, or a substituted or unsubstituted carbazole group.

According to one embodiment of the present specification, Ar1a and Ar1b are the same as or different from each other, and each independently is a phenyl group unsubstituted or substituted with an aryl group or a heteroaryl group, a biphenyl group, a terphenyl group, a fluorene group unsubstituted or substituted with an alkyl group, a dibenzofuran group, a dibenzothiophene group, or a carbazole group unsubstituted or substituted with an aryl group.

According to one embodiment of the present specification, Ar1a and Ar1b are the same as or different from each other, and each independently is a phenyl group unsubstituted or substituted with a phenyl group, a fluorene group substituted with a methyl group, a dibenzofuran group or a dibenzothiophene group, a biphenyl group, a terphenyl group, a fluorene group unsubstituted or substituted with a methyl group, a dibenzofuran group, a dibenzothiophene group, or a carbazole group unsubstituted or substituted with a phenyl group.

According to one embodiment of the present specification, Ar1a and Ar1b are the same as or different from each other, and can be each independently one selected from among the following structural formulae:

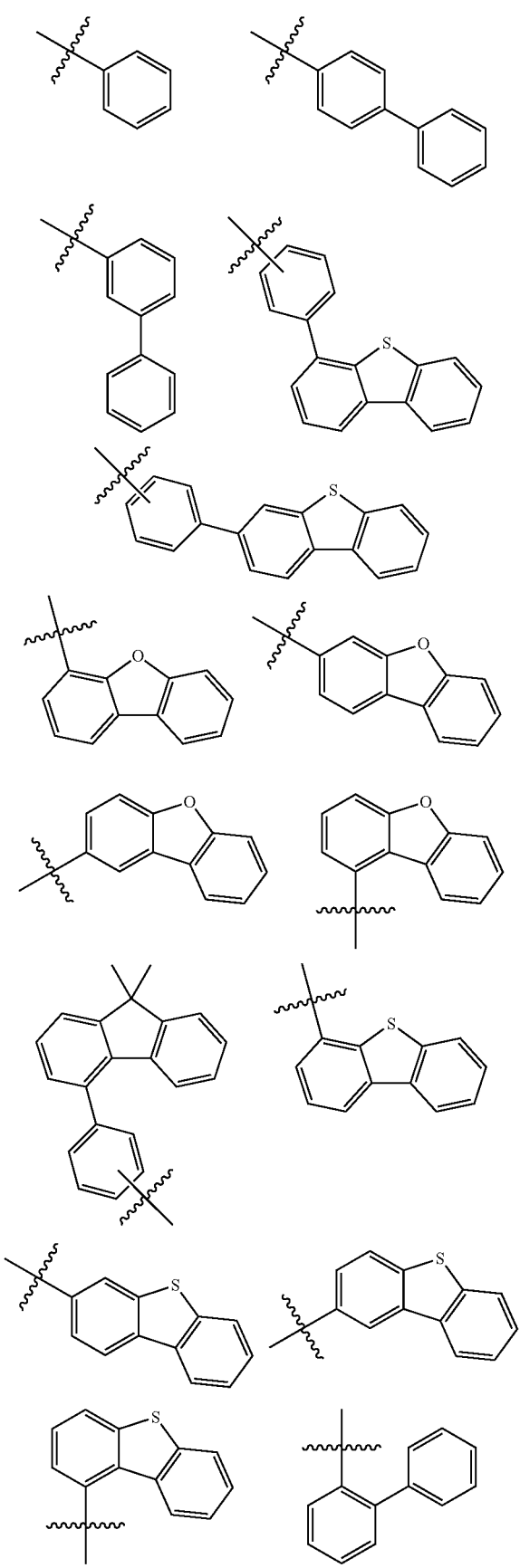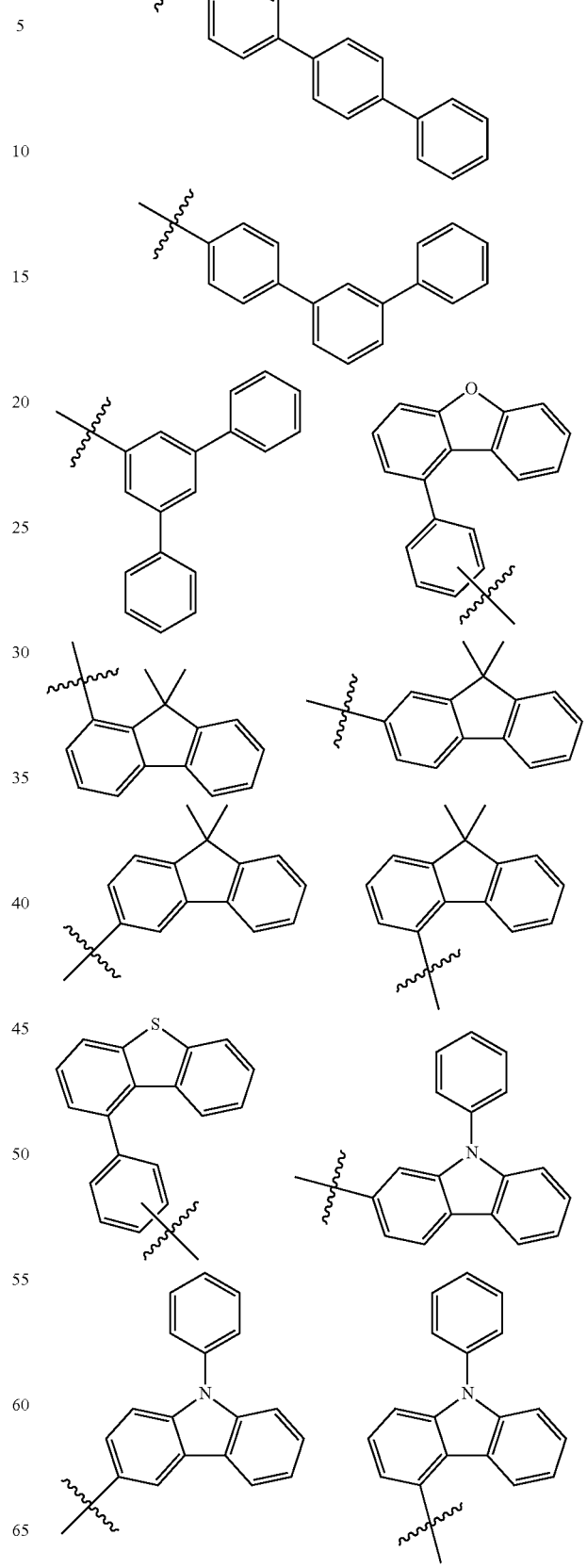

-continued

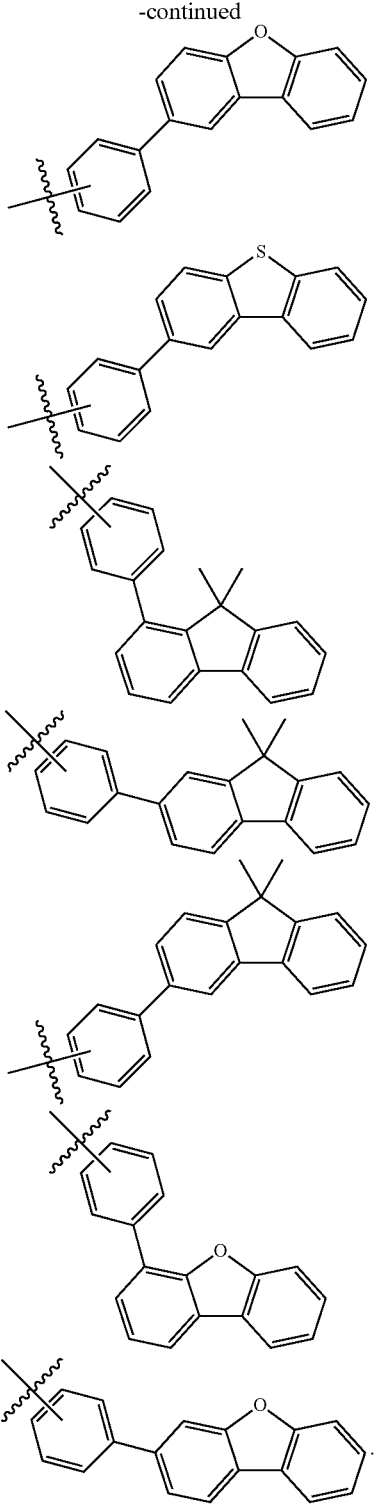

According to one embodiment of the present specification, Ar2 is a substituted or unsubstituted aryl group having 6 to 30 carbon atoms.

According to one embodiment of the present specification, Ar2 is a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted triphenylene group, a substituted or unsubstituted phenanthrene group, a substituted or unsubstituted chrysene group, a substituted or unsubstituted fluoranthene group, a substituted or unsubstituted pyrene group, a substituted or unsubstituted perylene group, a substituted or unsubstituted benzophenanthrene group, a substituted or unsubstituted benzotetraphene group, or a substituted or unsubstituted tetraphene group.

According to one embodiment of the present specification, Ar2 is a phenyl group, a biphenyl group, a terphenyl group, a quaterphenyl group, a naphthyl group, a triphenylene group, a phenanthrene group, a chrysene group, a fluoranthene group, a pyrene group, a perylene group, a benzophenanthrene group, a benzotetraphene group, or a tetraphene group.

According to one embodiment of the present specification, Ar2 can be one selected from among the following structural formulae:

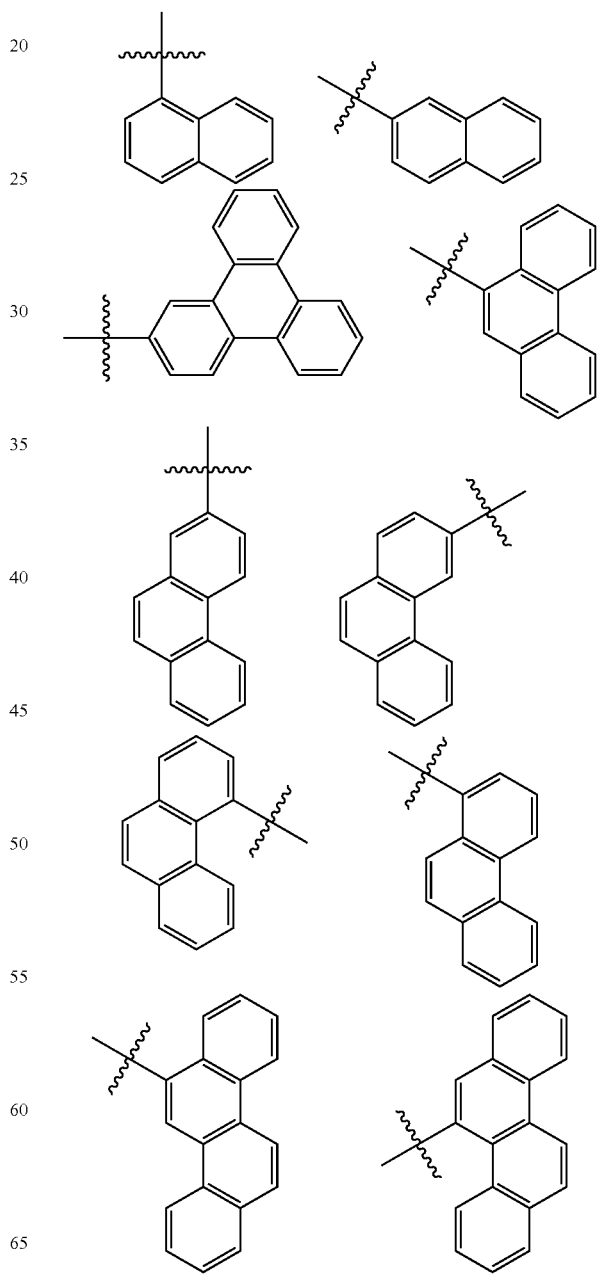

-continued

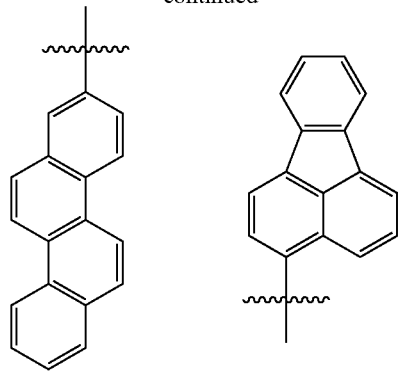

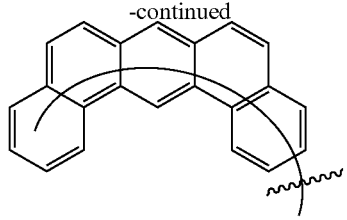

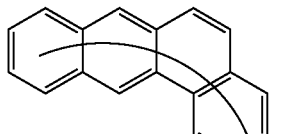

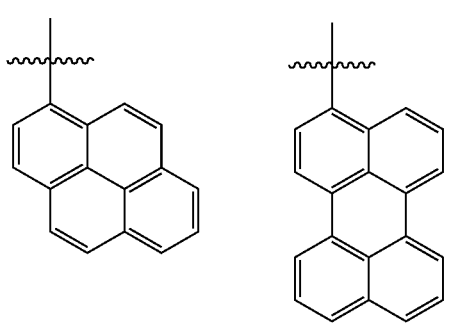

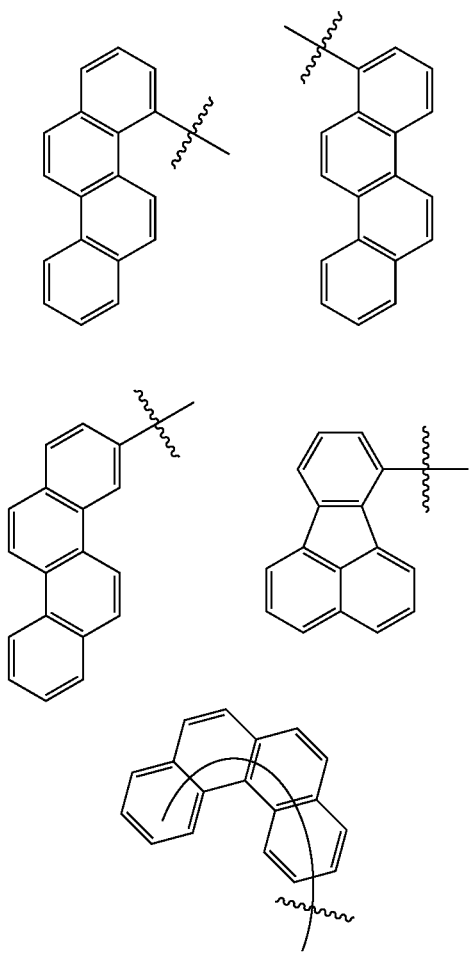

According to one embodiment of the present specification, Ar2 can be Chemical Formula 2:

[Chemical Formula 2]

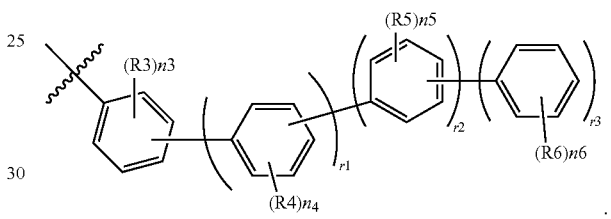

In Chemical Formula 2:

R3 to R6 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

n3 to n5 are each independently an integer of 0 to 4, n6 is an integer of 0 to 5, and when n3 to n6 are each an integer of 2 or greater, substituents in the parentheses are the same as or different from each other;

r1 to r3 are each independently an integer of 0 to 5, and when r1 to r3 are each an integer of 2 or greater, structures in the parentheses are the same as or different from each other; and $n3+r1=5, n4+r2=5$ and $n5+r3=5$.

According to one embodiment of the present specification, Chemical Formula 2 can be selected from among the following Chemical Formulae 2-1 to 2-6:

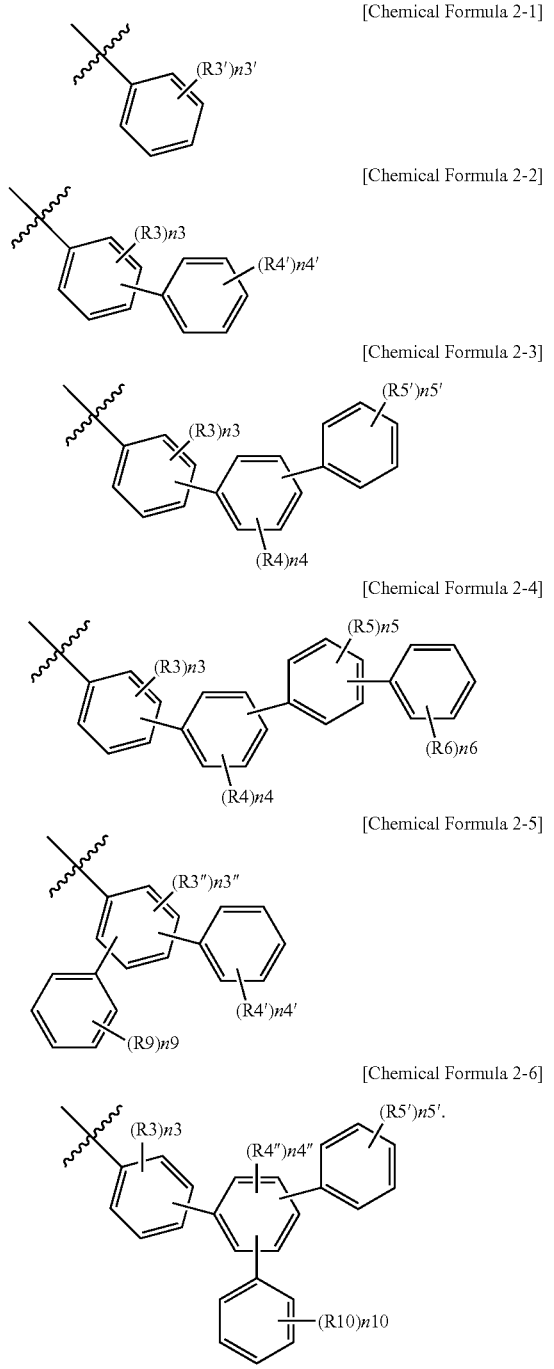

[Chemical Formula 2-1]
[Chemical Formula 2-2]
[Chemical Formula 2-3]
[Chemical Formula 2-4]
[Chemical Formula 2-5]
[Chemical Formula 2-6]

In Chemical Formulae 2-1 to 2-6, R3' to R5' have the same definitions as R3 to R5 in Chemical Formula 2, respectively, R9 and R10 have the same definitions as R4 and R5 in Chemical Formula 2, respectively, n3' to n5', and n9 and n10 are each an integer of 0 to 5, n3" and n4" are each an integer of 0 to 3, and when n3' to n5', n3", n4", n9 and n10 are each an integer of 2 or greater, substituents in the parentheses are the same as or different from each other, and the remaining substituents have the same definitions as in Chemical Formula 2.

According to one embodiment of the present specification, R3 to R6 are hydrogen.

According to one embodiment of the present specification, R3 to R6, R3' to R5', and R9 and R10 are hydrogen.

According to one embodiment of the present specification, L1 and L2 are the same as or different from each other, and each independently is a direct bond or an arylene group having 6 to 30 carbon atoms.

According to one embodiment of the present specification, L1 and L2 are the same as or different from each other, and each independently is a direct bond, a substituted or unsubstituted phenylene group, a substituted or unsubstituted biphenylene group, a substituted or unsubstituted naphthylene group, a substituted or unsubstituted terphenylene group, a substituted or unsubstituted quaterphenylene group, a substituted or unsubstituted anthracenylene group, a substituted or unsubstituted phenanthrenylene group, a substituted or unsubstituted triphenylenylene group, a substituted or unsubstituted pyrenylene group, a substituted or unsubstituted fluorenylene group, or a substituted or unsubstituted spirocyclopentanefluorenylene group.

According to one embodiment of the present specification, L1 and L2 are the same as or different from each other, and each independently is a direct bond, a phenylene group, a biphenylene group unsubstituted or substituted with a nitrile group, a naphthylene group, a terphenylene group, a quaterphenylene group, an anthracenylene group, a phenanthrenylene group, a triphenylenylene group, a pyrenylene group, a fluorenylene group unsubstituted or substituted with an alkyl group or an aryl group, or a spirocyclopentanefluorenylene group.

According to one embodiment of the present specification, L1 and L2 are the same as or different from each other, and can be each independently is a direct bond, or one of the following structural formulae:

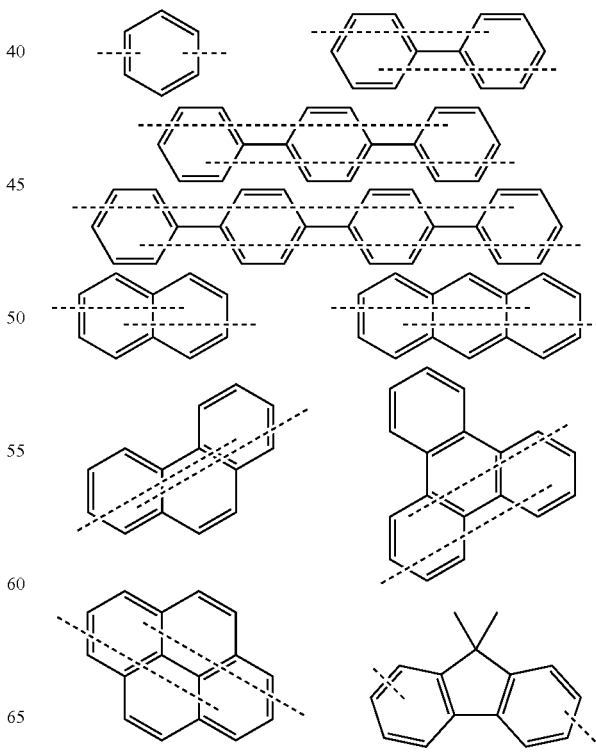

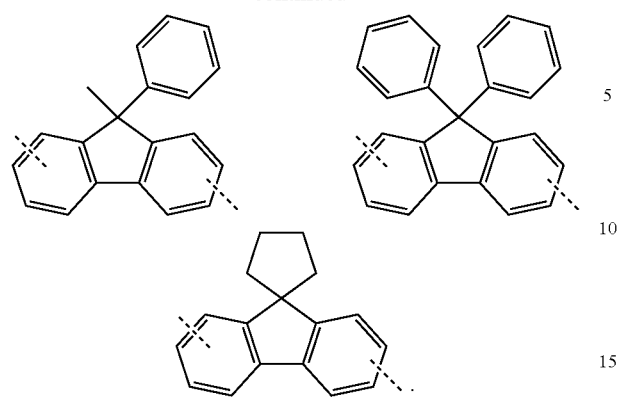
In the structures, ----- is a site bonding to a main chain.
According to one embodiment of the present specification, Chemical Formula 1 can be one selected from among the following Chemical Formulae 1-1 to 1-16:
[Chemical Formula 1-1]
[Chemical Formula 1-2]
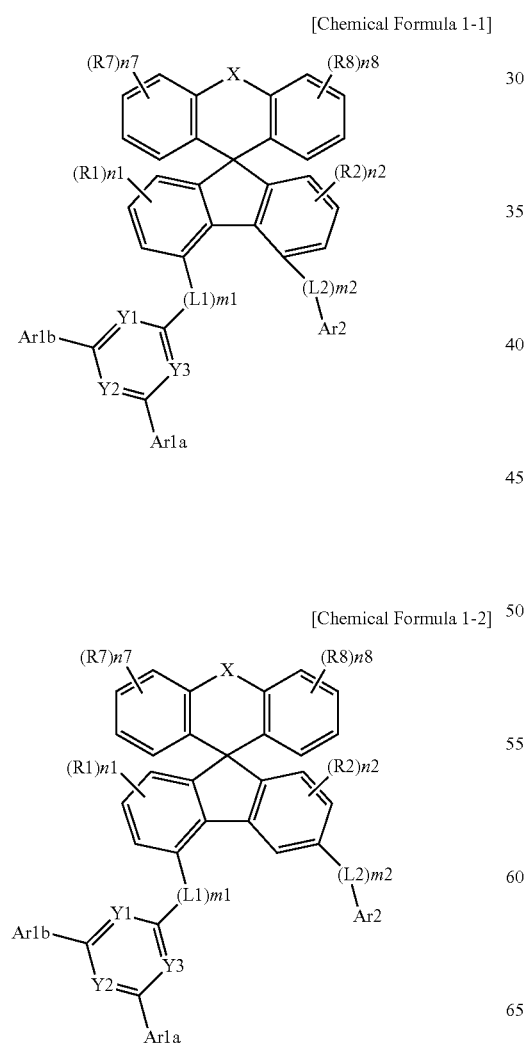
[Chemical Formula 1-3]
[Chemical Formula 1-4]
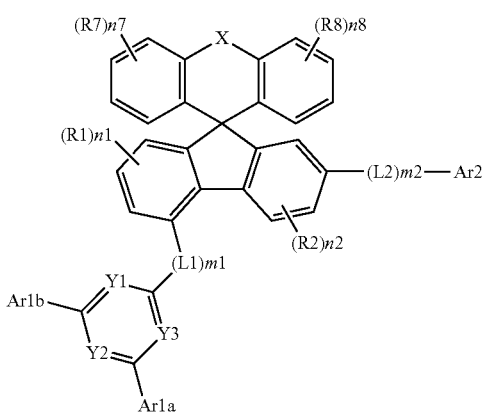
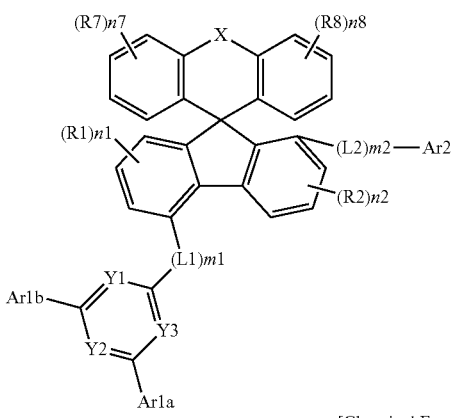
[Chemical Formula 1-5]
[Chemical Formula 1-6]
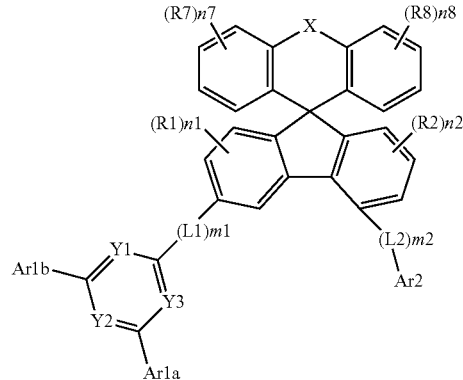

[Chemical Formula 1-7]
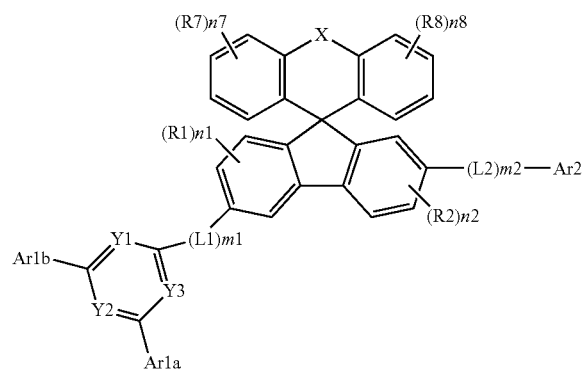
[Chemical Formula 1-8]
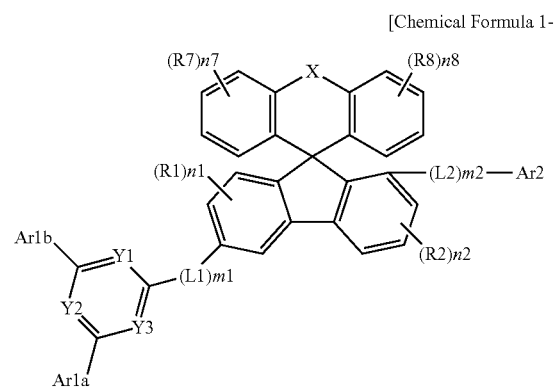
[Chemical Formula 1-9]
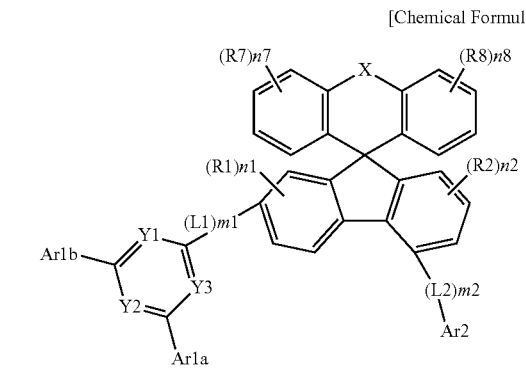
[Chemical Formula 1-10]
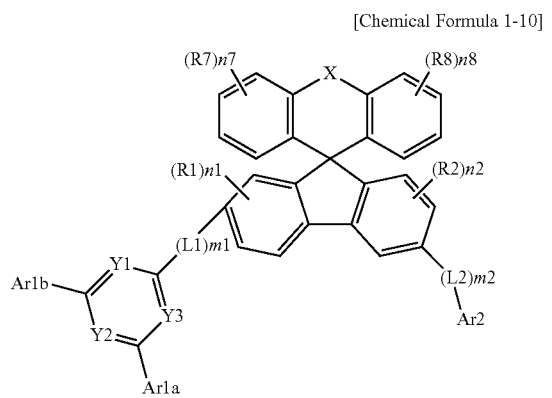
[Chemical Formula 1-11]
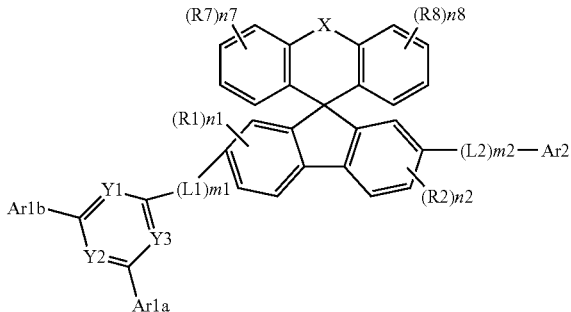
[Chemical Formula 1-12]
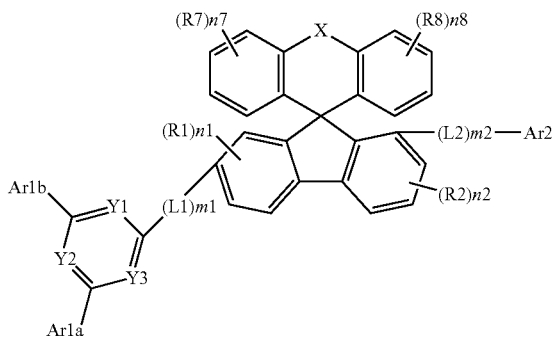
[Chemical Formula 1-13]
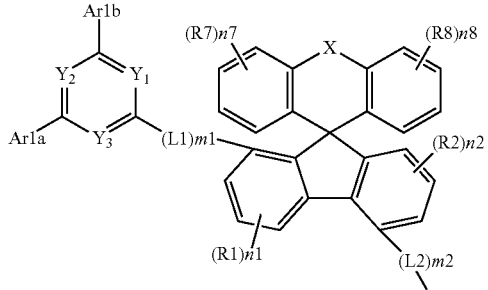
[Chemical Formula 1-14]
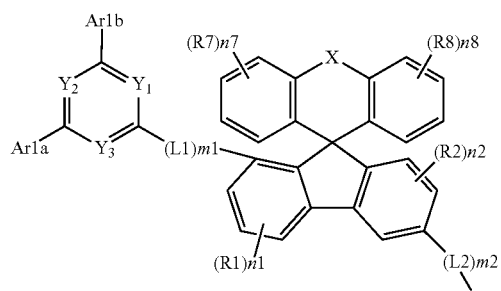
[Chemical Formula 1-15]
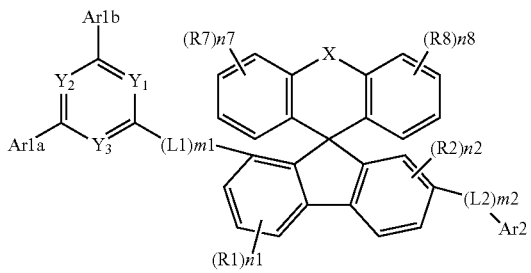

[Chemical Formula 1-16]

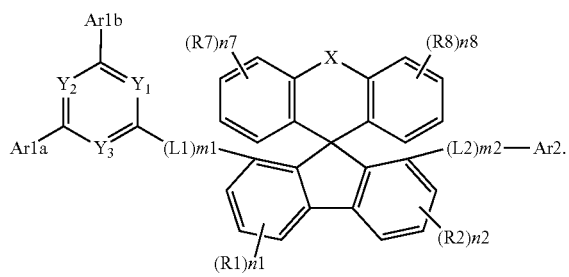

In Chemical Formulae 1-1 to 1-16, the substituents have the same definitions as in Chemical Formula 1.

According to one embodiment of the present specification, Chemical Formula 1 can be one selected from among the following Chemical Formulae 1-17 to 1-32:

[Chemical Formula 1-17]

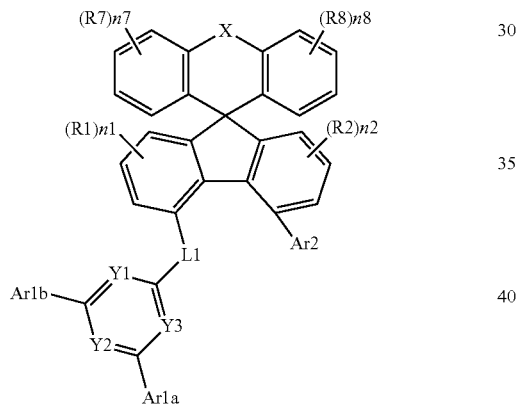

[Chemical Formula 1-18]

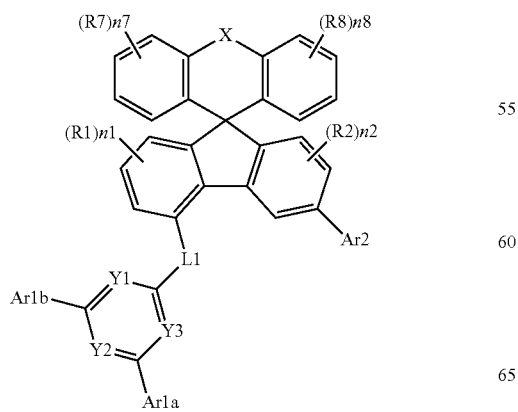

[Chemical Formula 1-19]

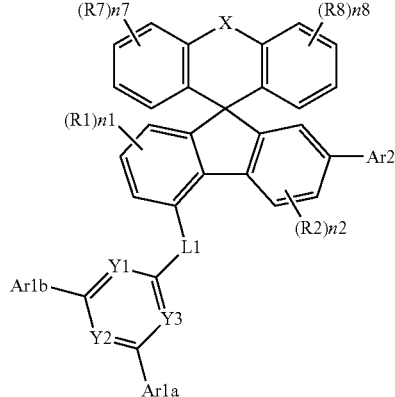

[Chemical Formula 1-20]

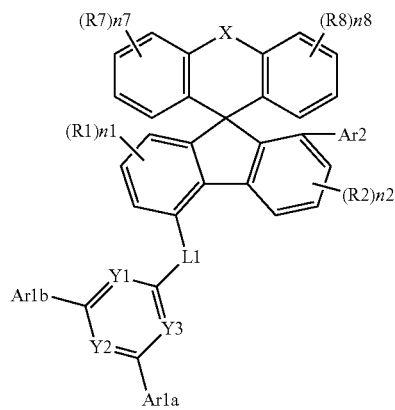

[Chemical Formula 1-21]

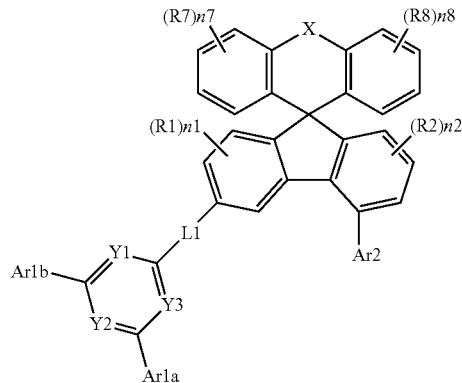

[Chemical Formula 1-22]

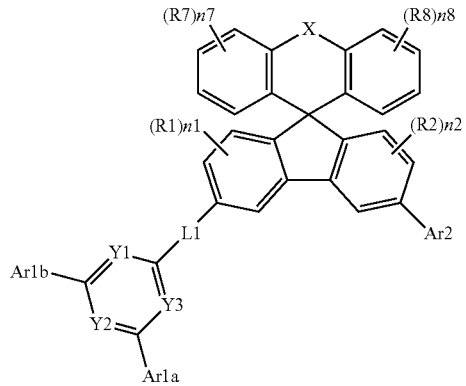

[Chemical Formula 1-23]
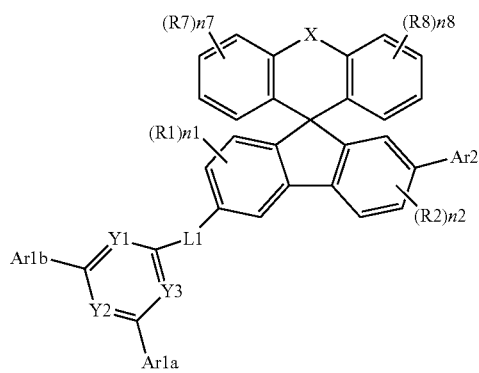
[Chemical Formula 1-24]
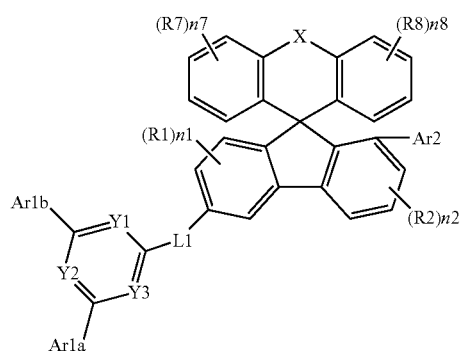
[Chemical Formula 1-25]
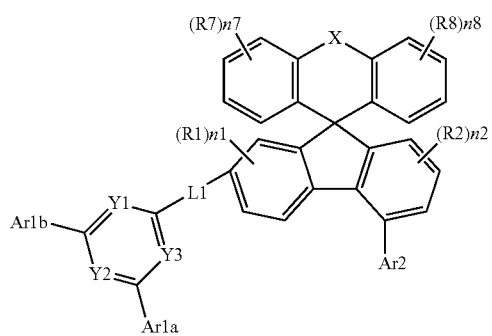
[Chemical Formula 1-26]
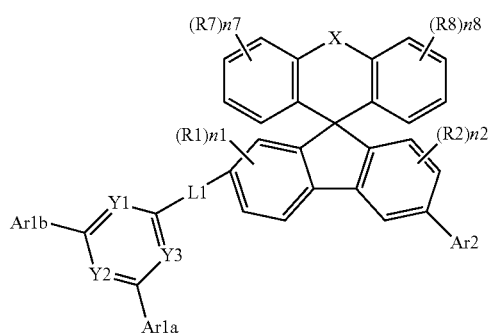
[Chemical Formula 1-27]
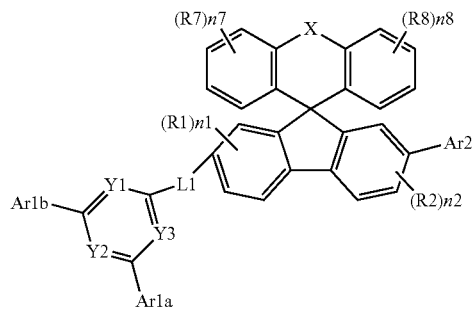
[Chemical Formula 1-28]
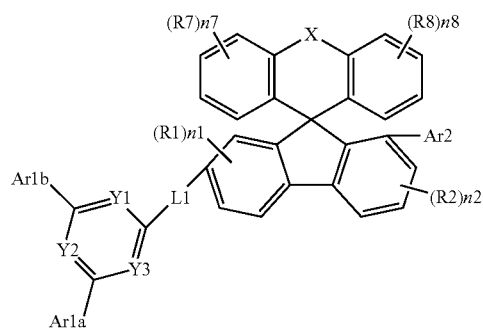
[Chemical Formula 1-29]
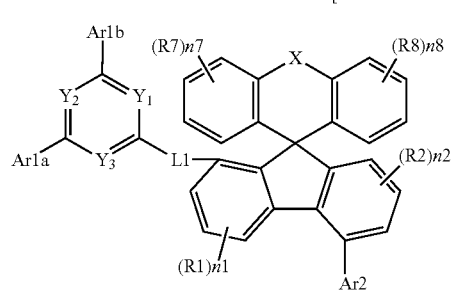

[Chemical Formula 30]

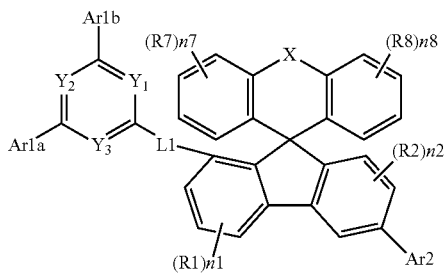

[Chemical Formula 1-31]

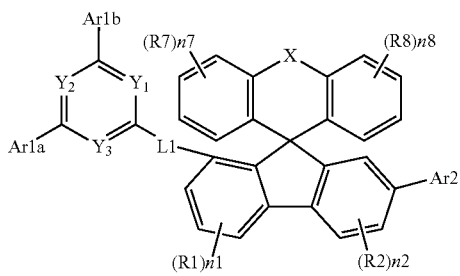

[Chemical Formula 1-32]

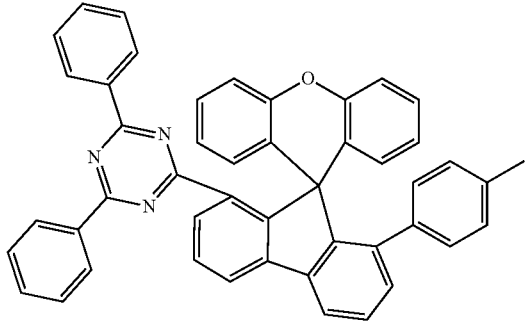

In Chemical Formulae 1-17 to 1-32, the substituents have the same definitions as in Chemical Formula 1.

According to one embodiment of the present specification, Y1 to Y3 are N.

According to one embodiment of the present specification, R1, R2, R7 and R8 are hydrogen.

According to one embodiment of the present specification, Chemical Formula 1 can be one selected from among the following compounds:

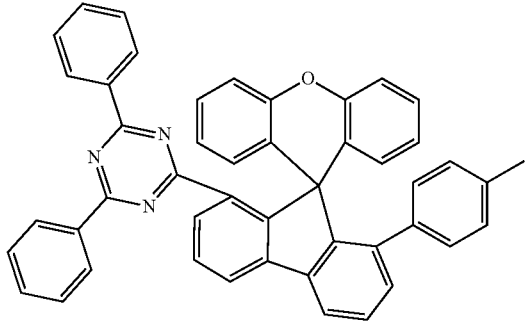

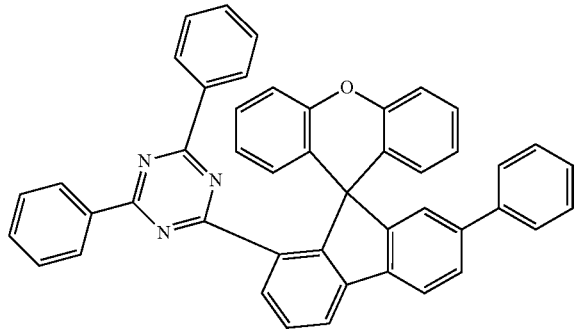

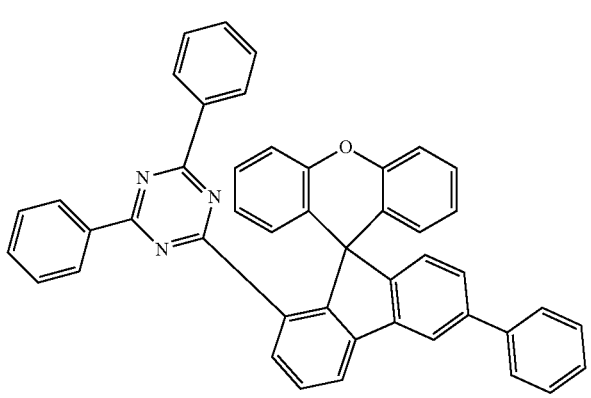

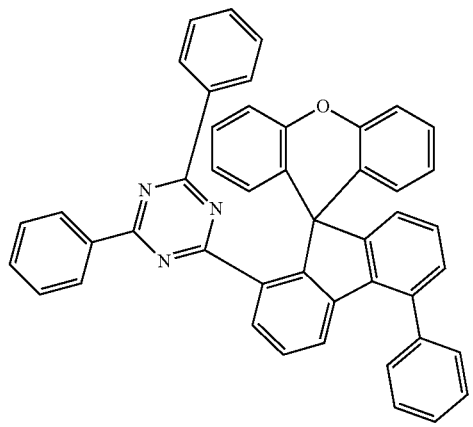

-continued
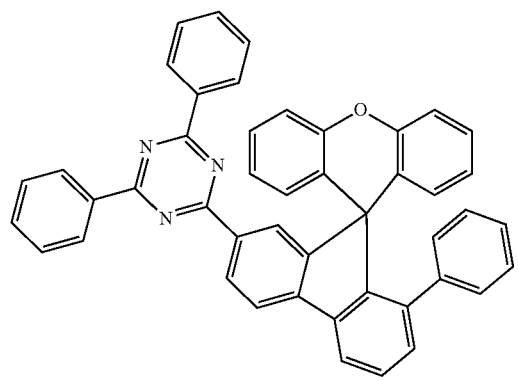
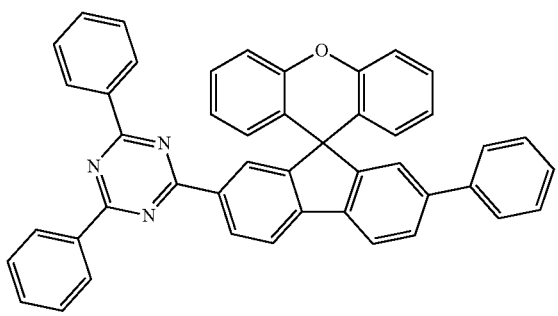
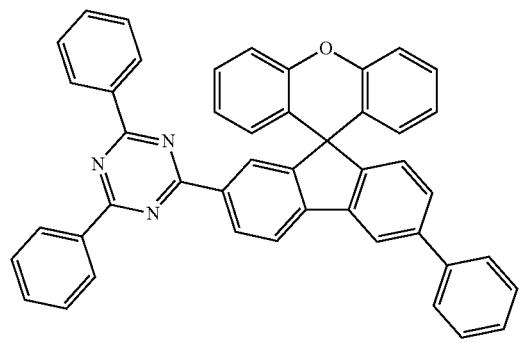
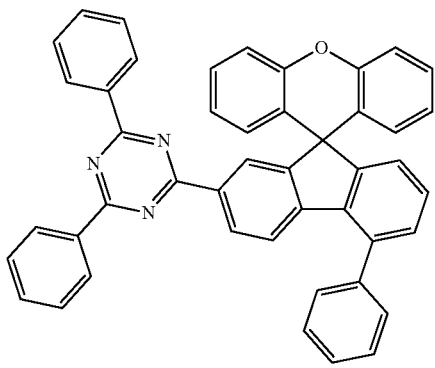
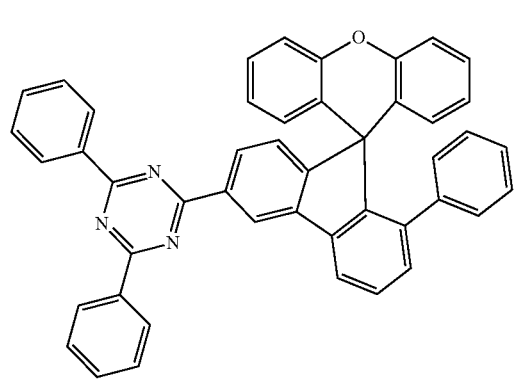
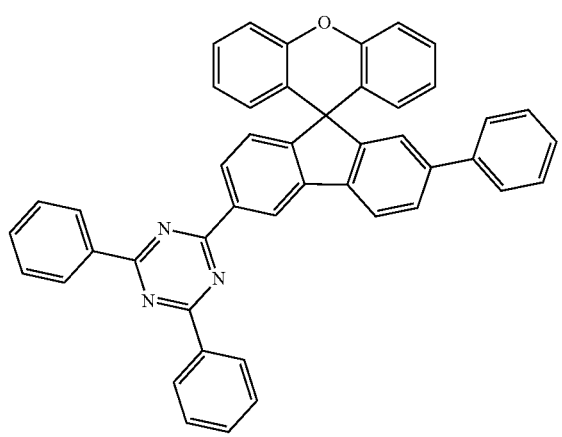
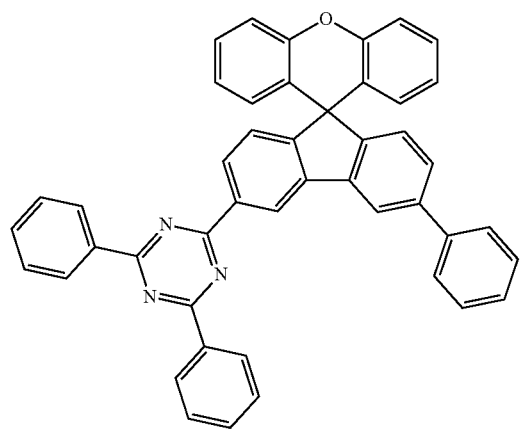
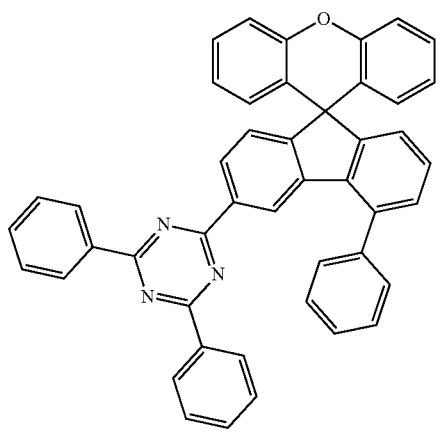

-continued
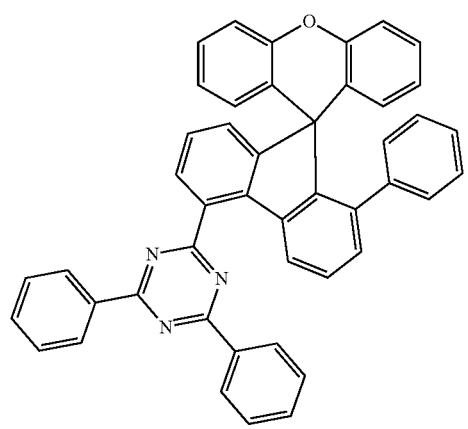
31
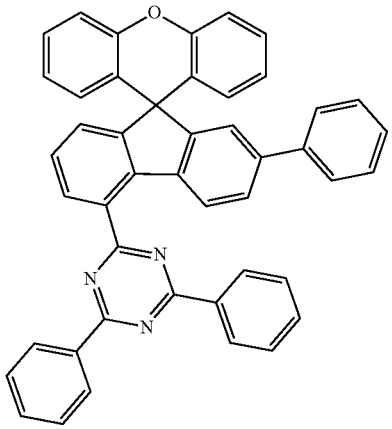
32
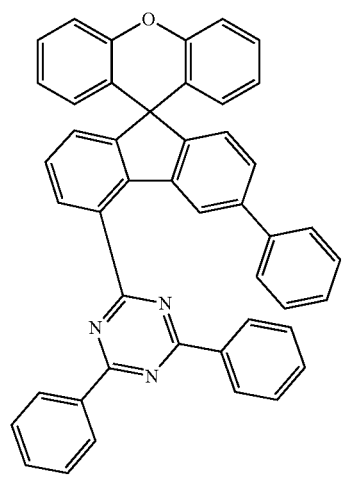
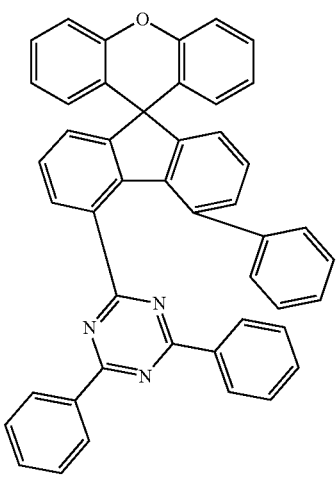
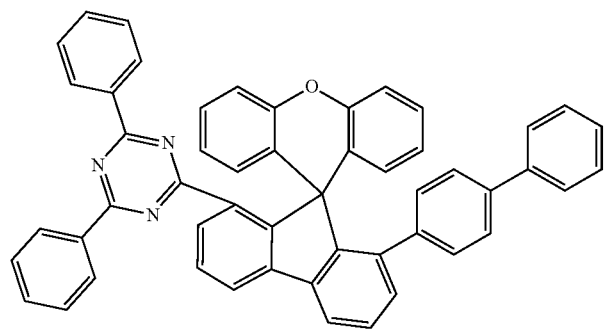
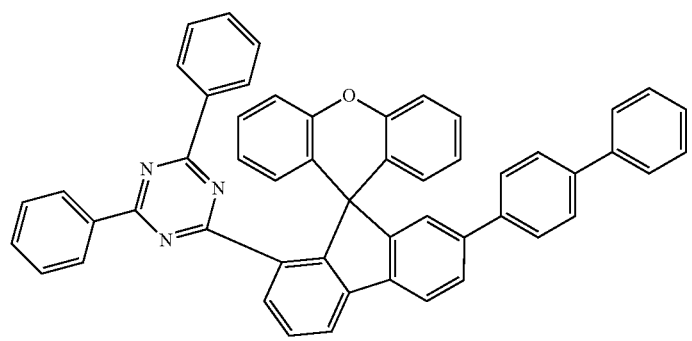

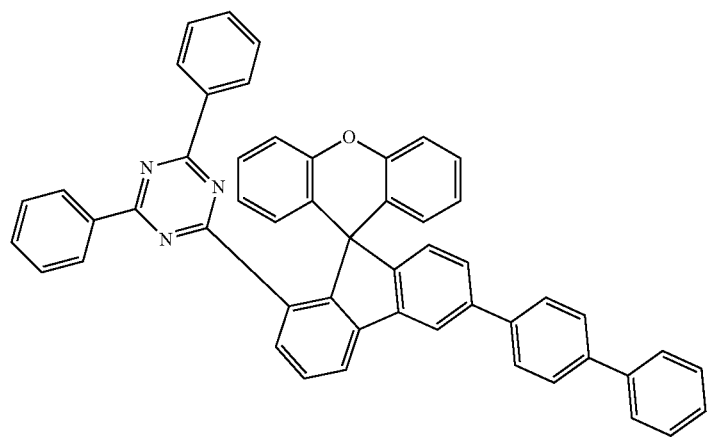
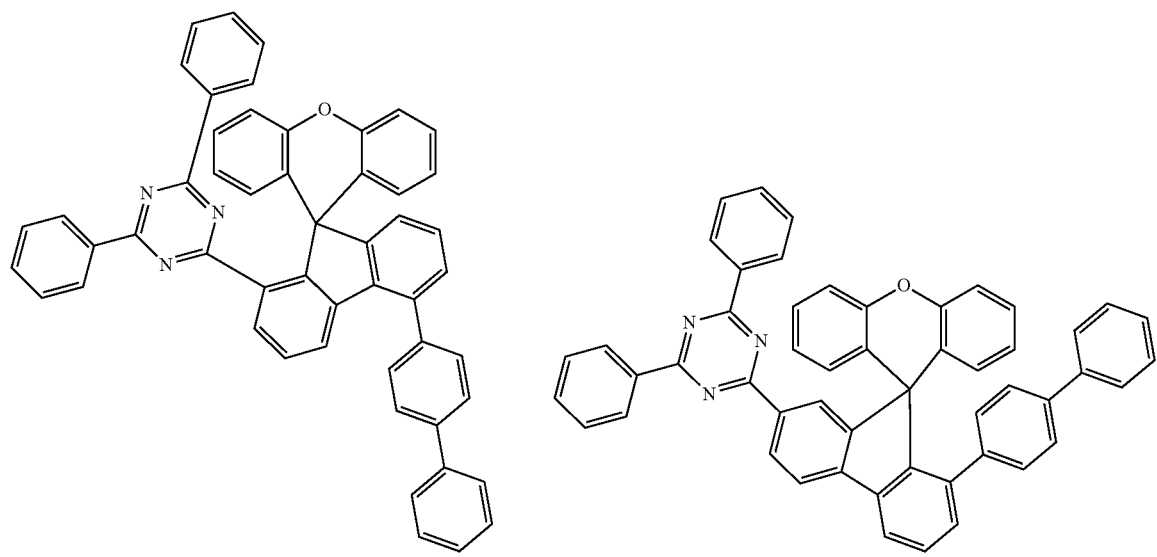
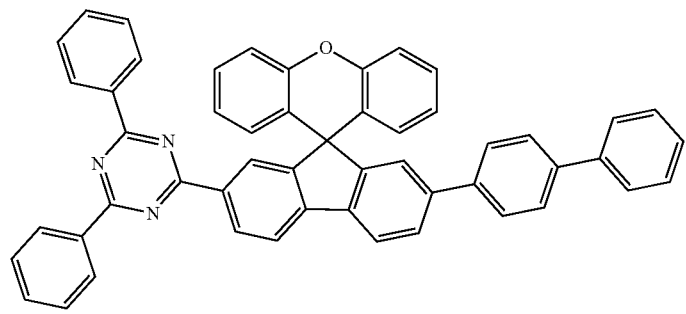

-continued
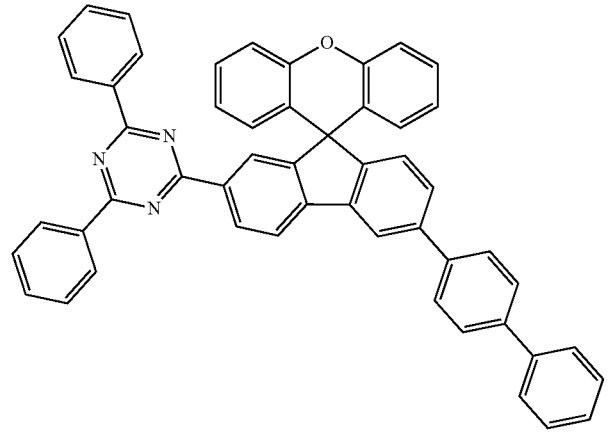
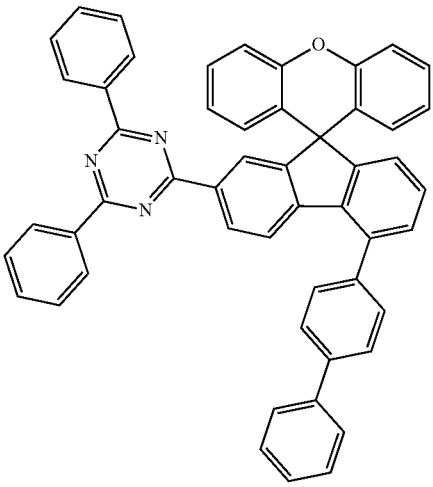
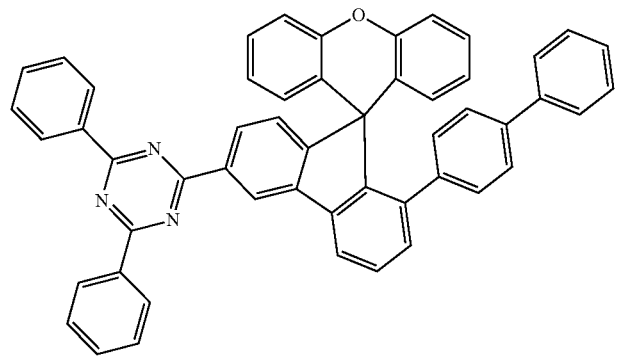
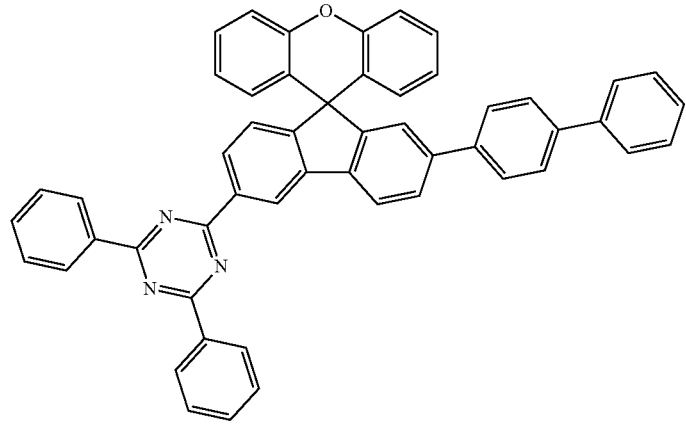
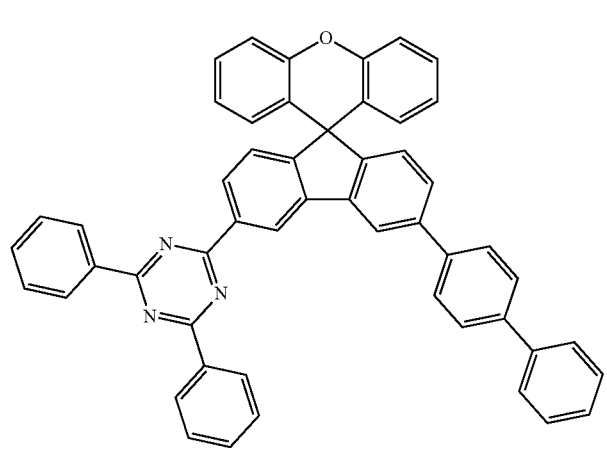
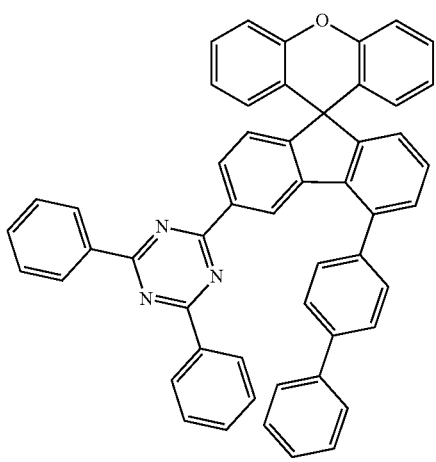

37
38
-continued
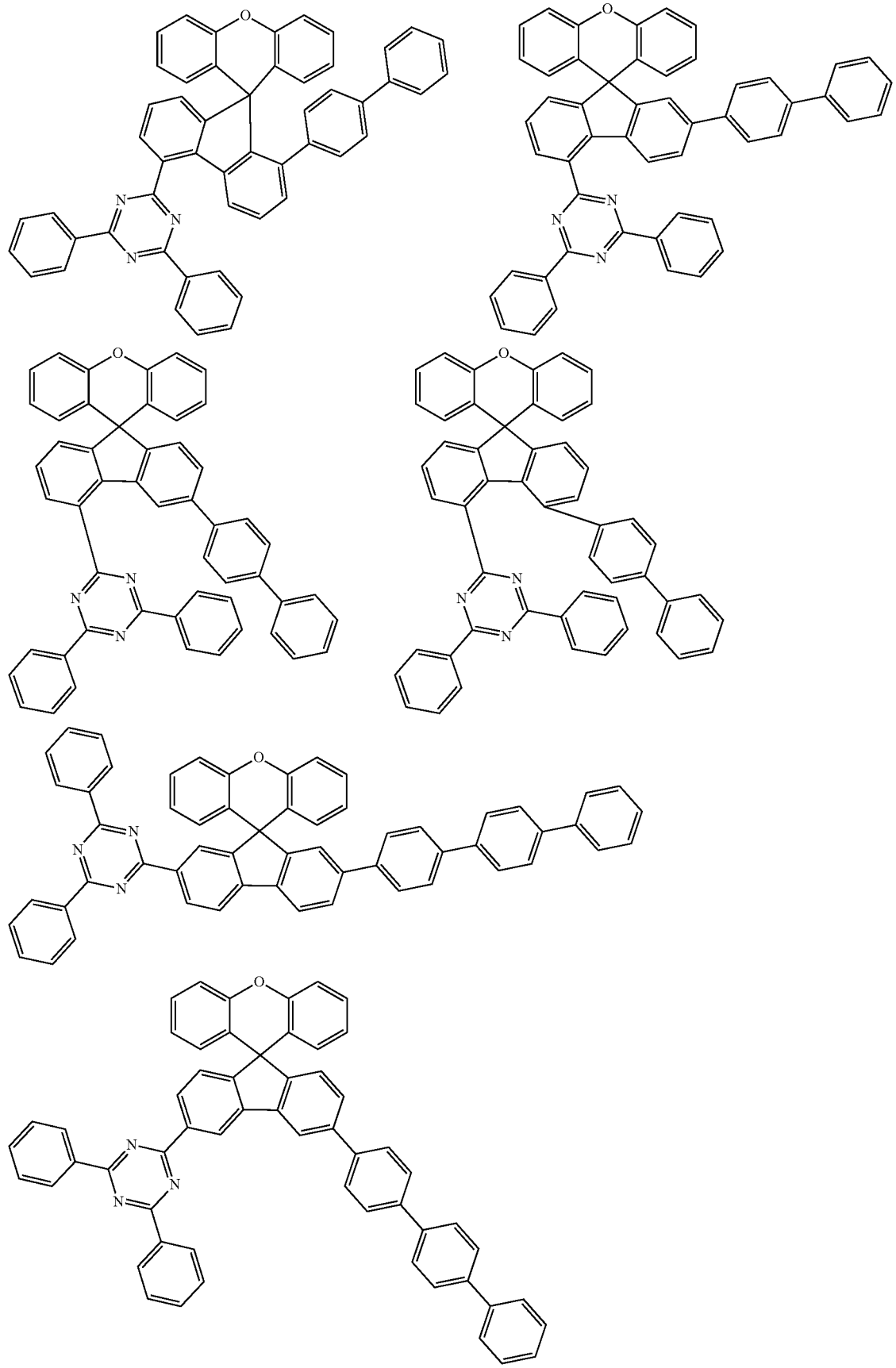

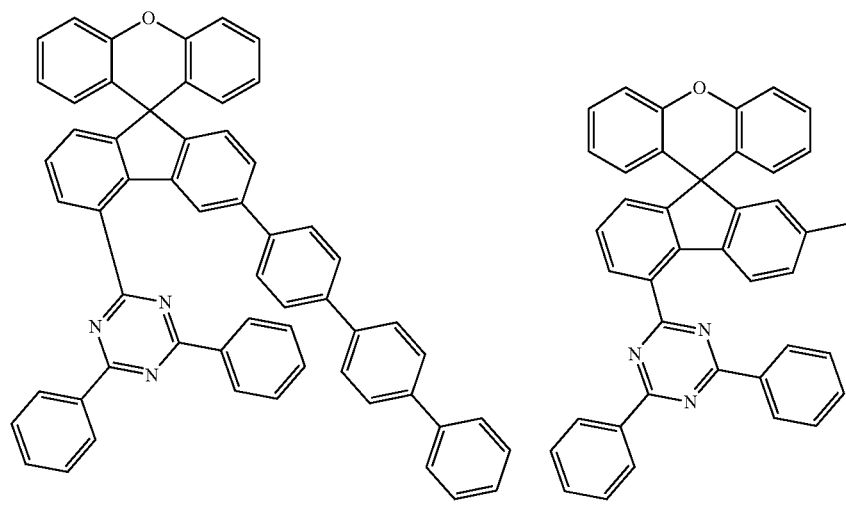
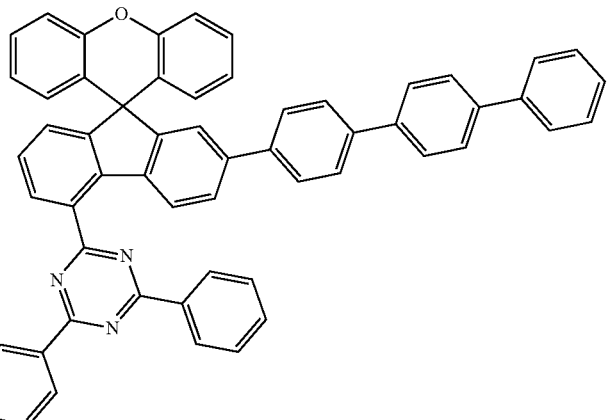
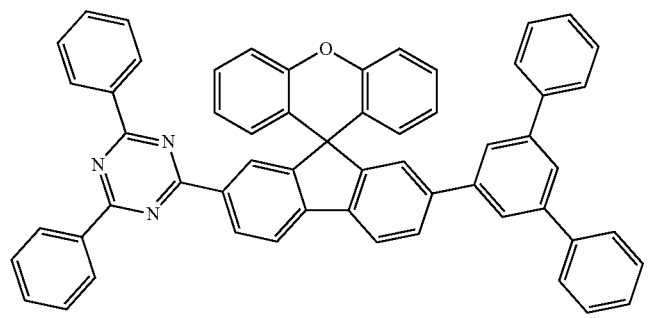
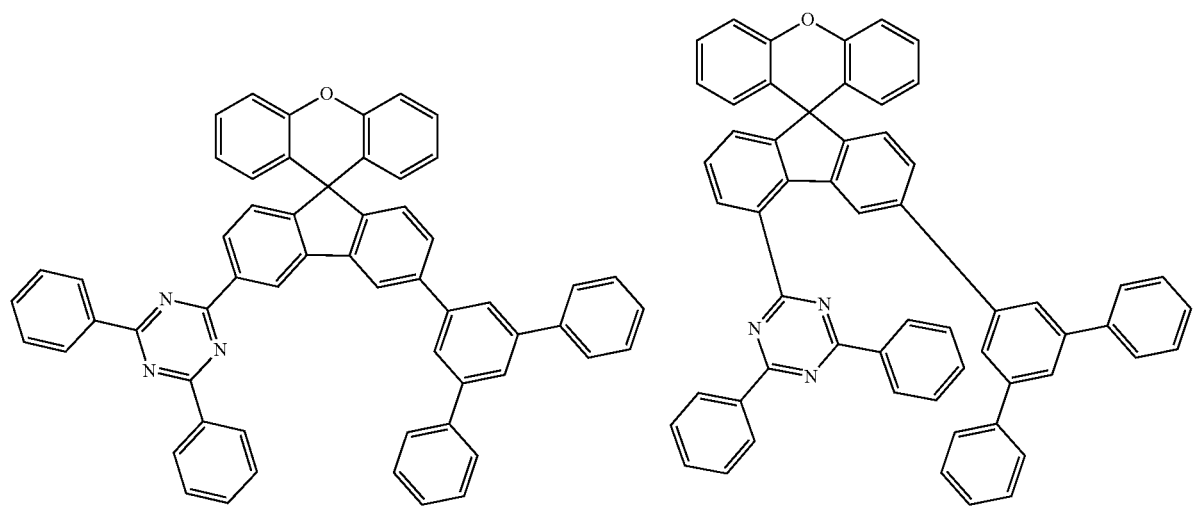

-continued
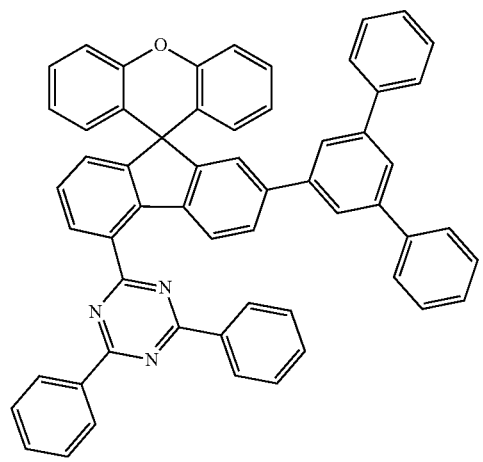 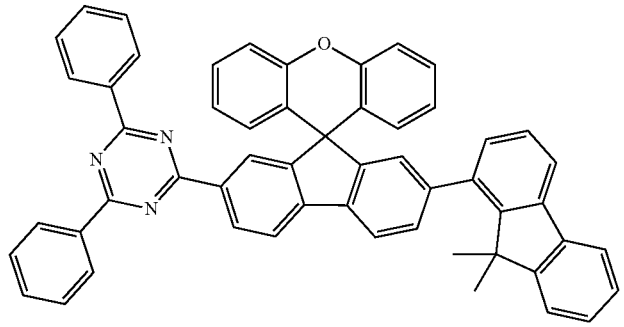
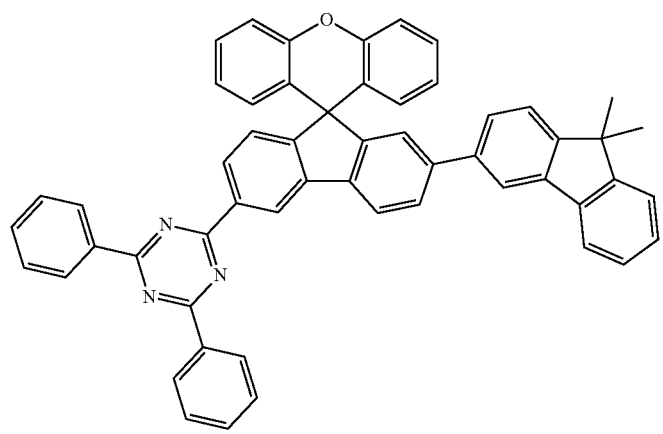 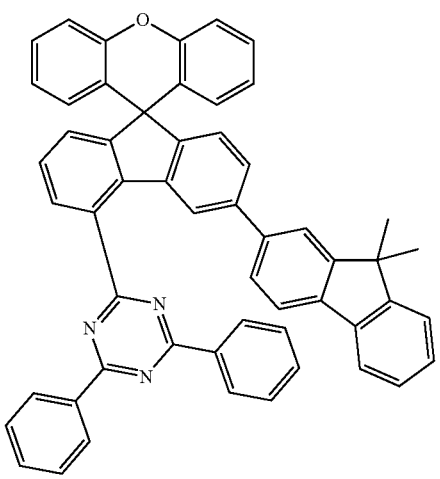
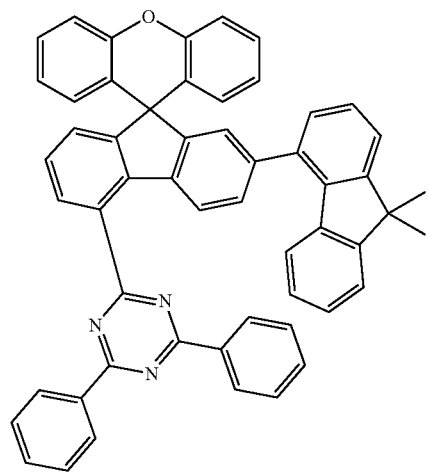 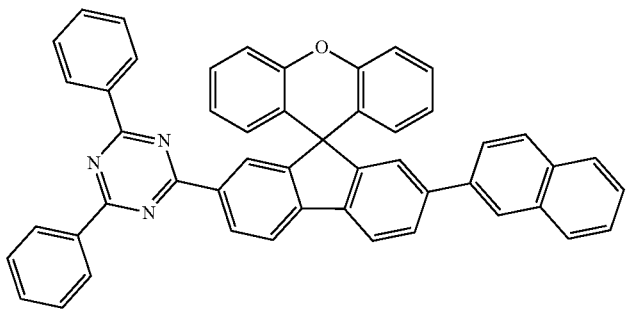

-continued
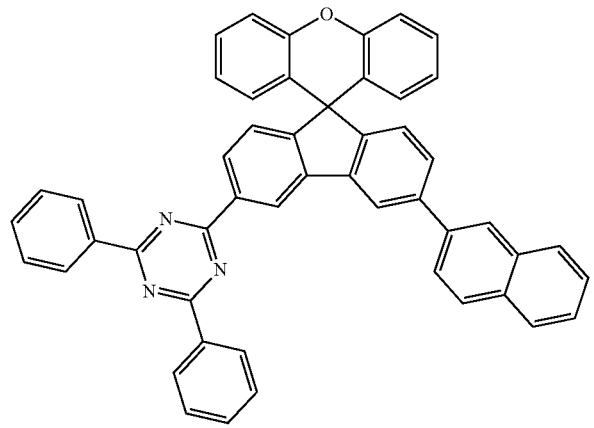
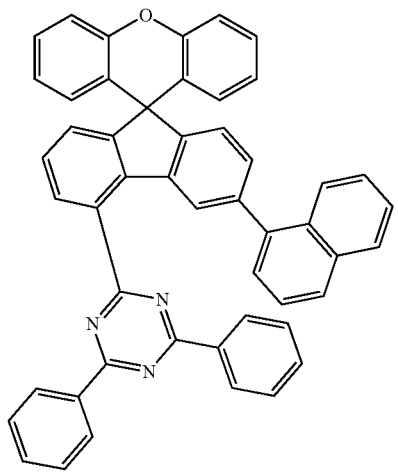
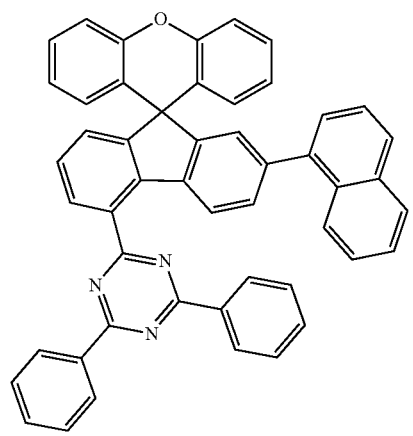
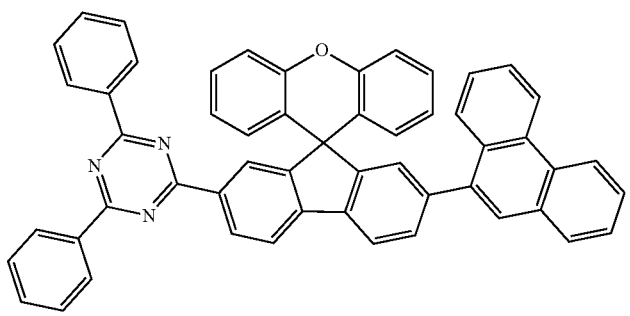
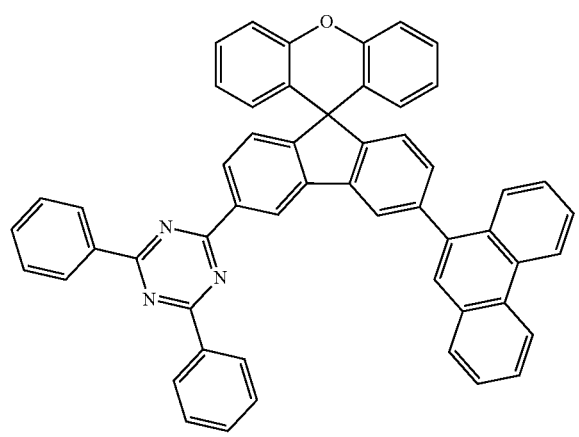
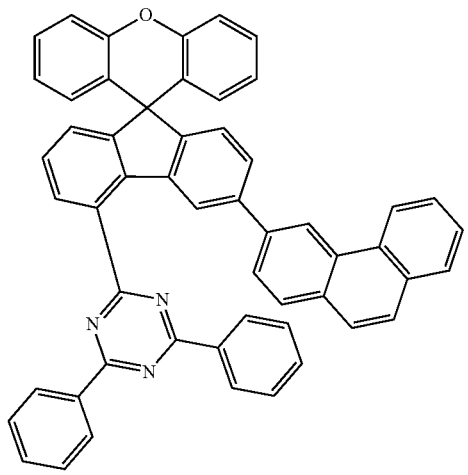

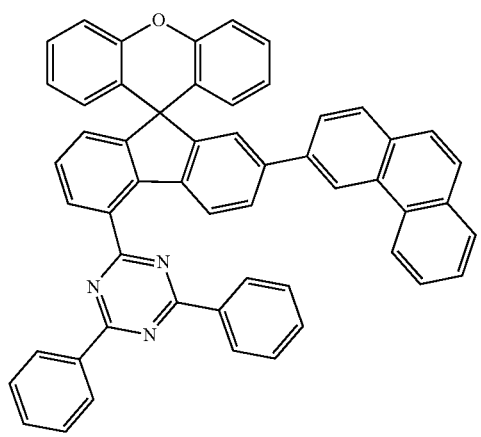
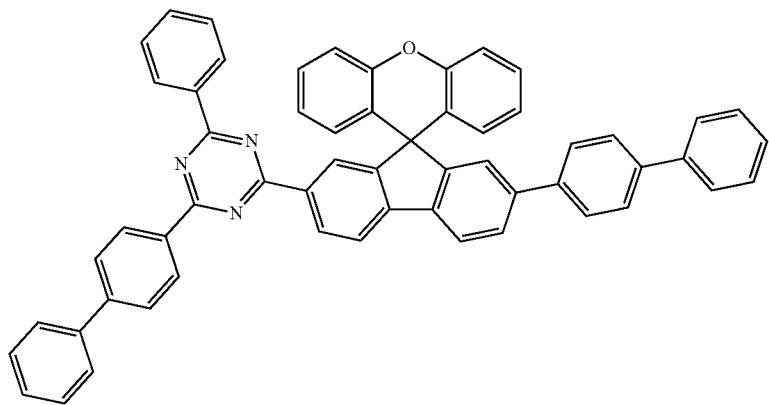
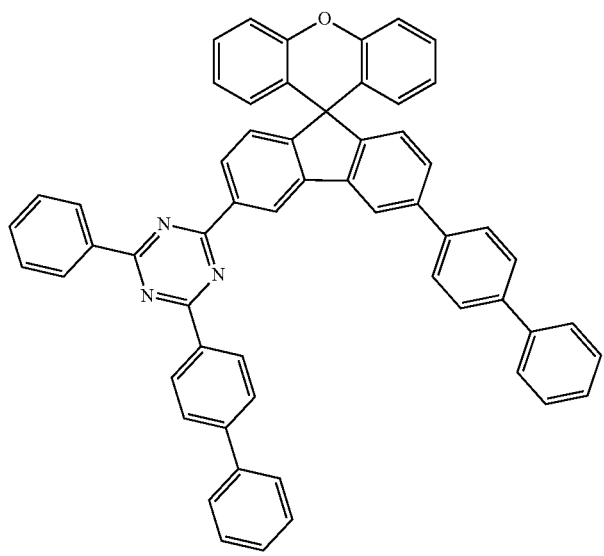
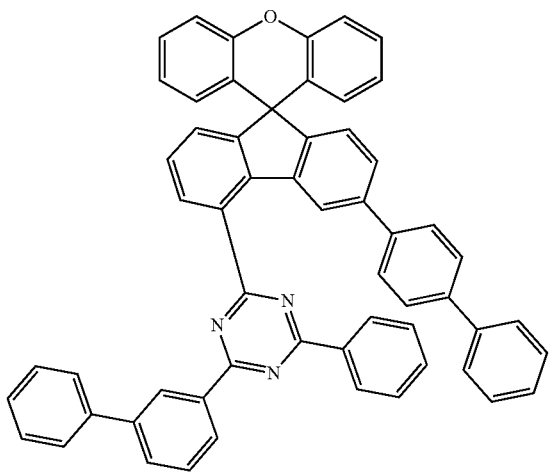

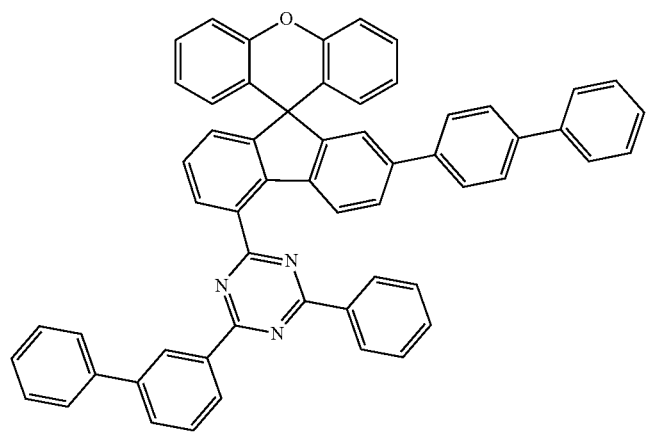
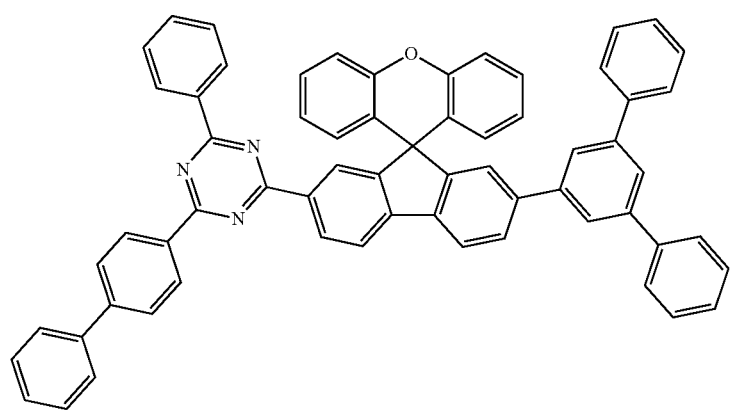
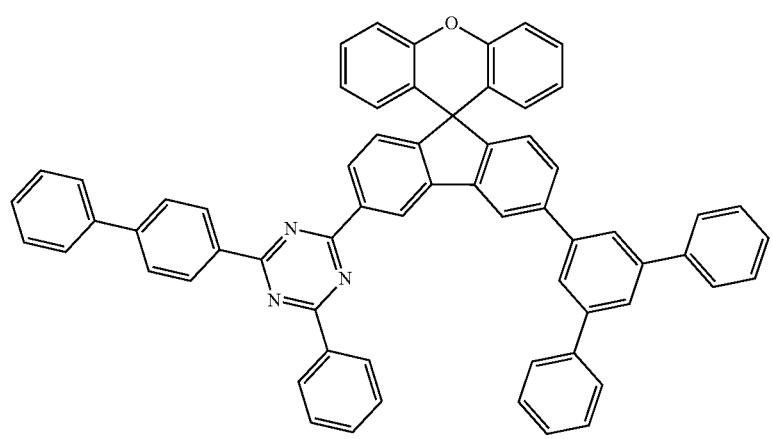

-continued
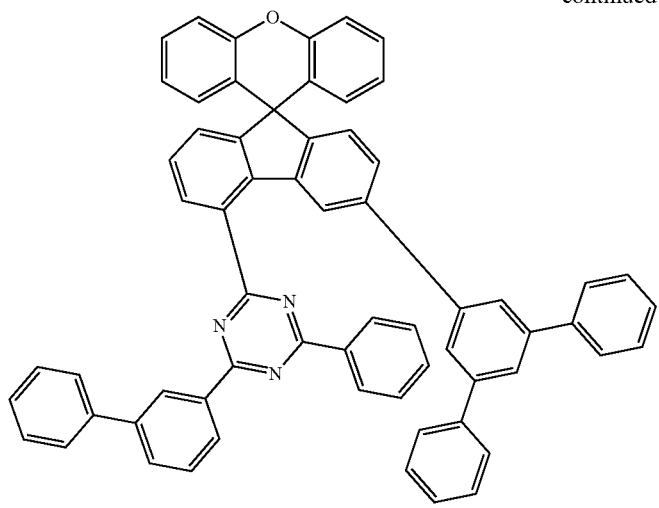
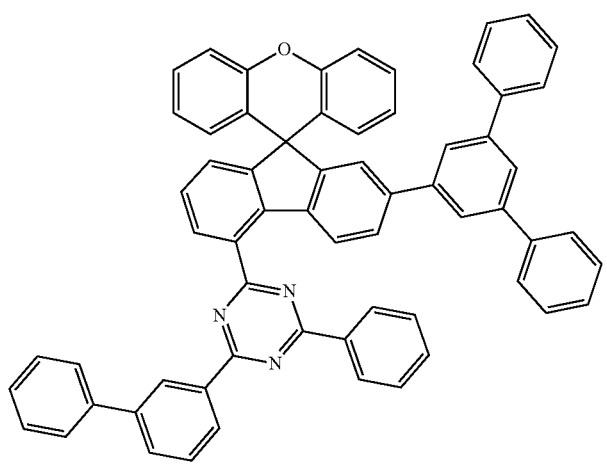
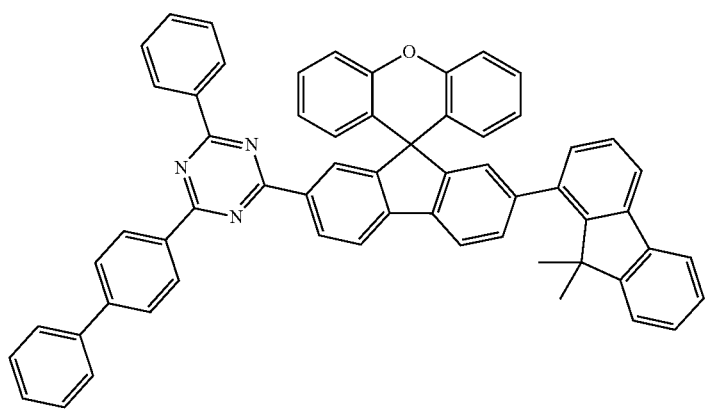

-continued
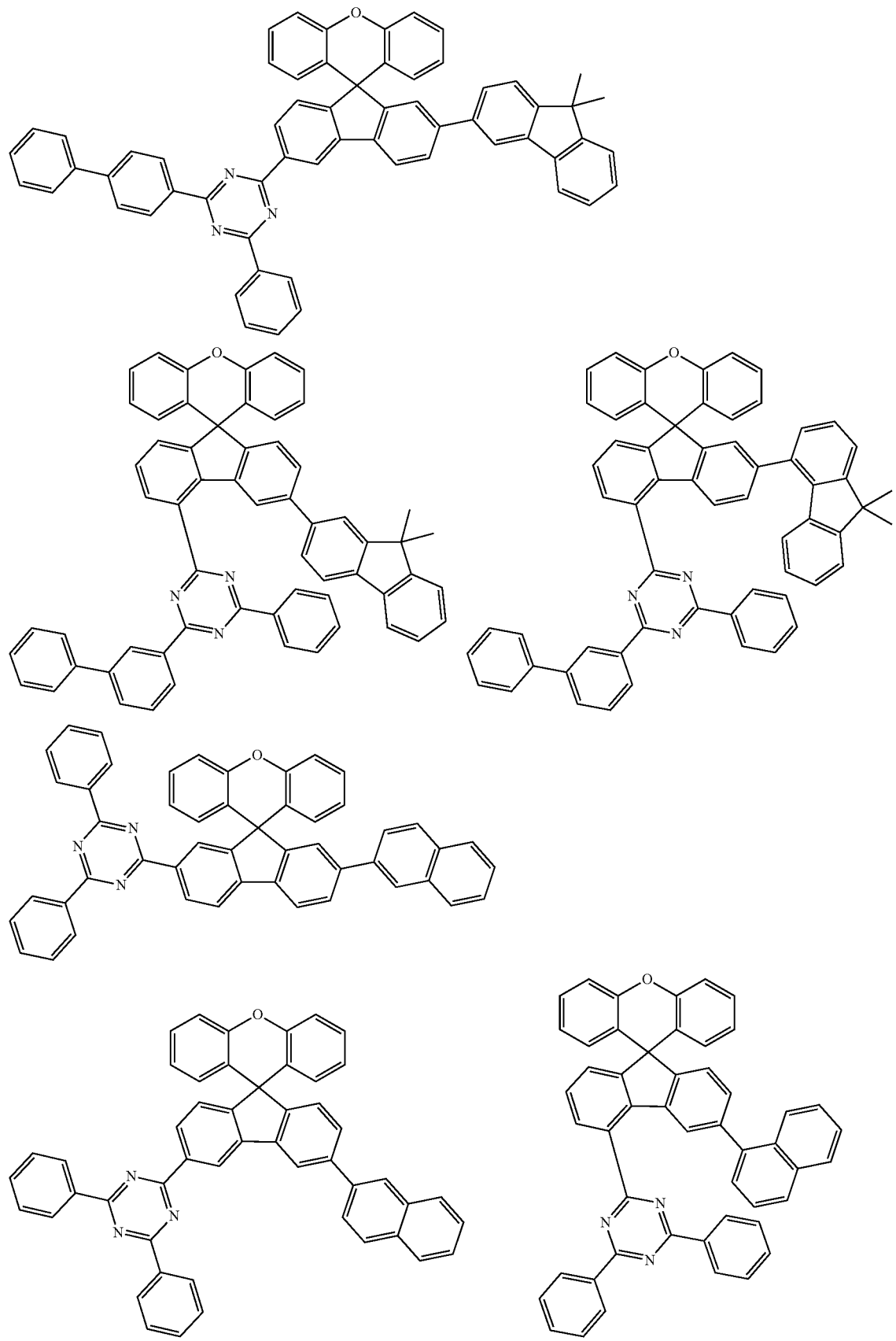

-continued
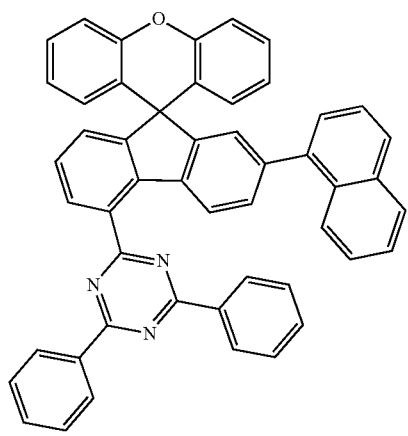
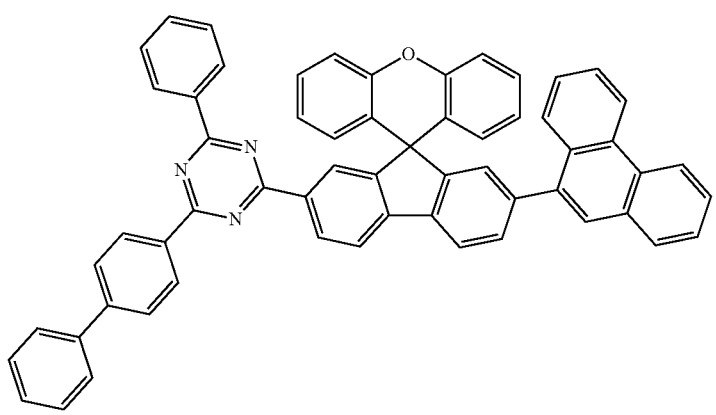
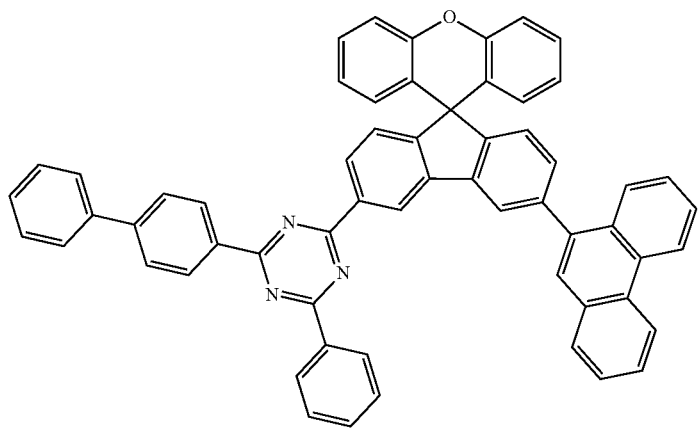
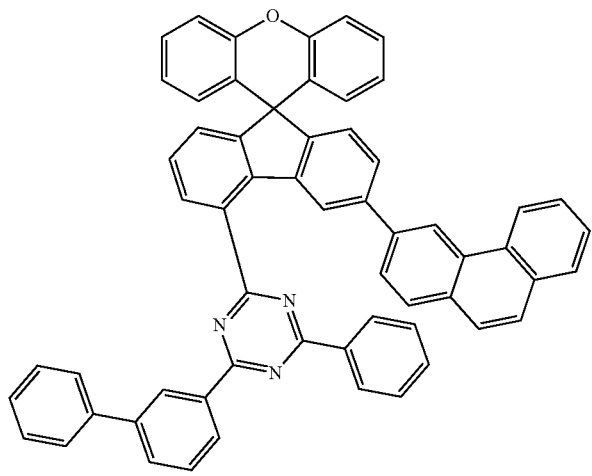
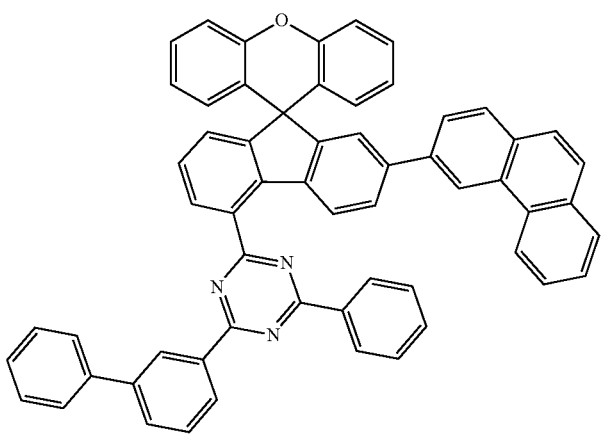
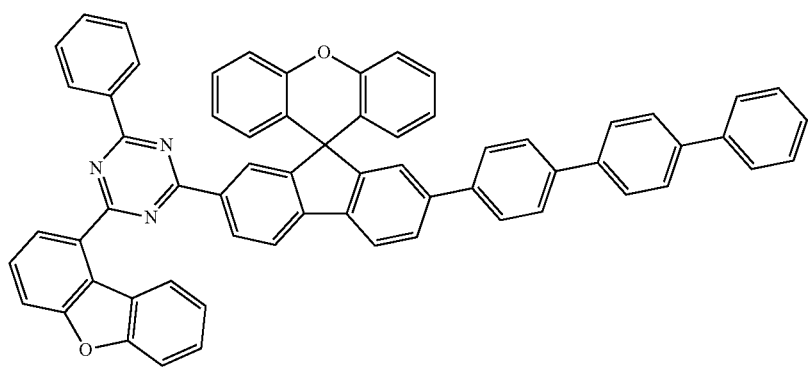

-continued
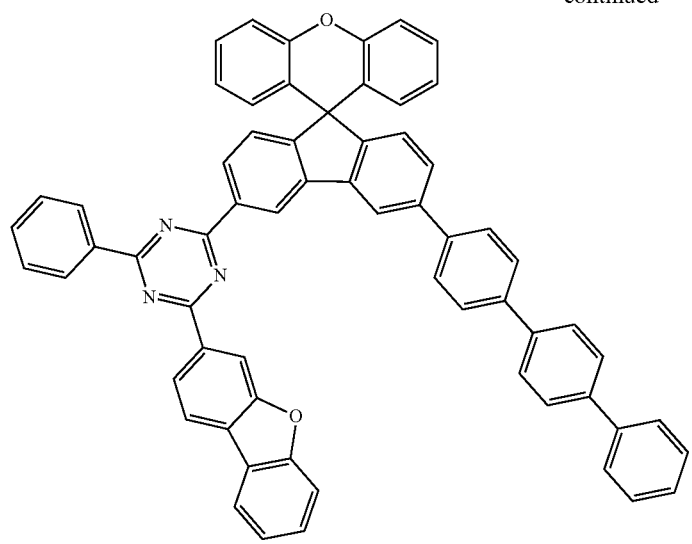
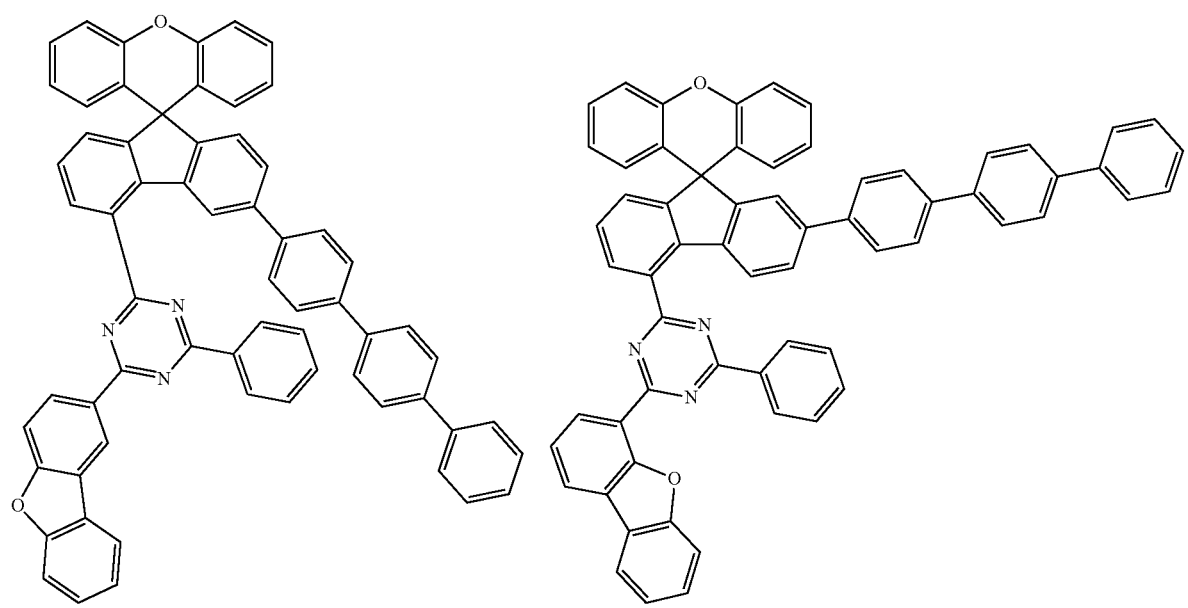
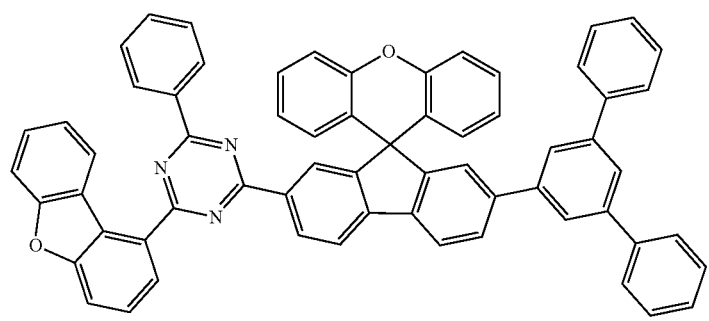

-continued
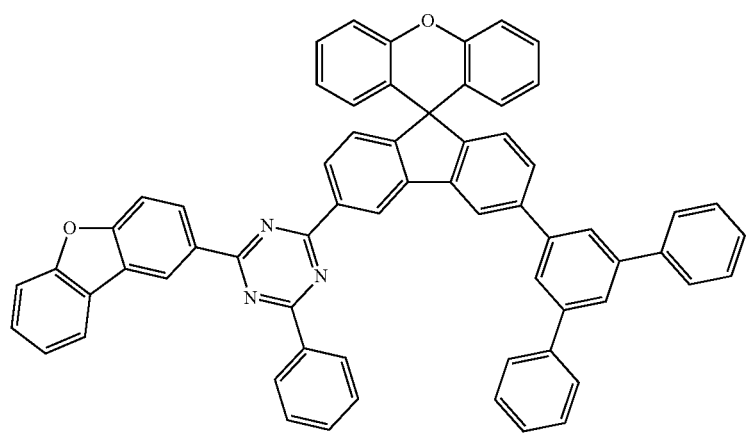
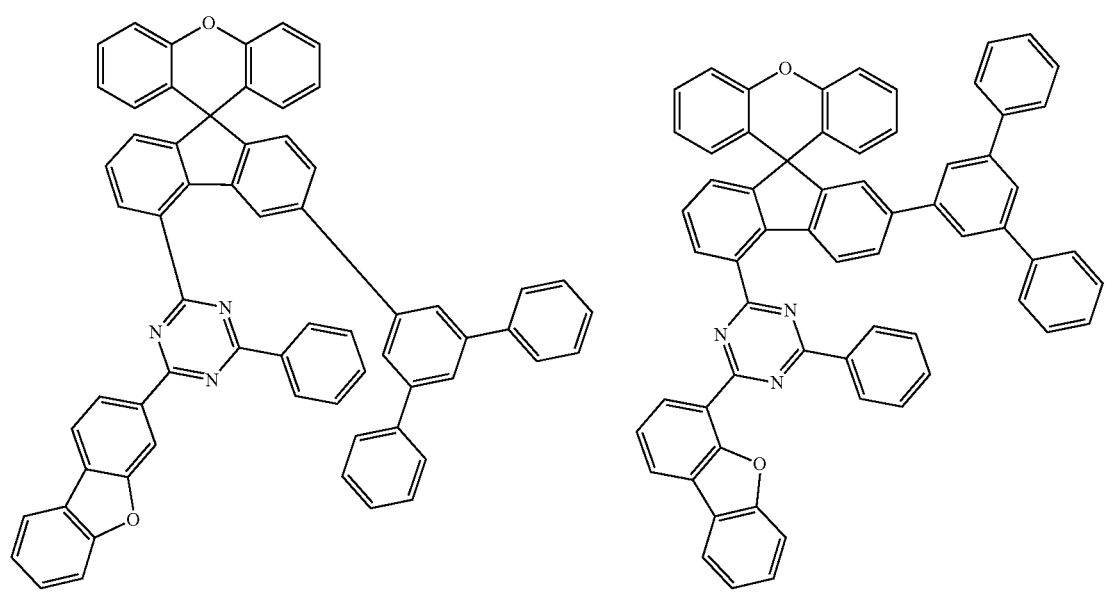
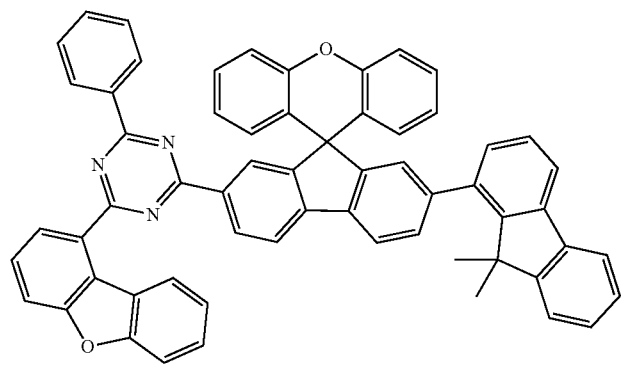

-continued
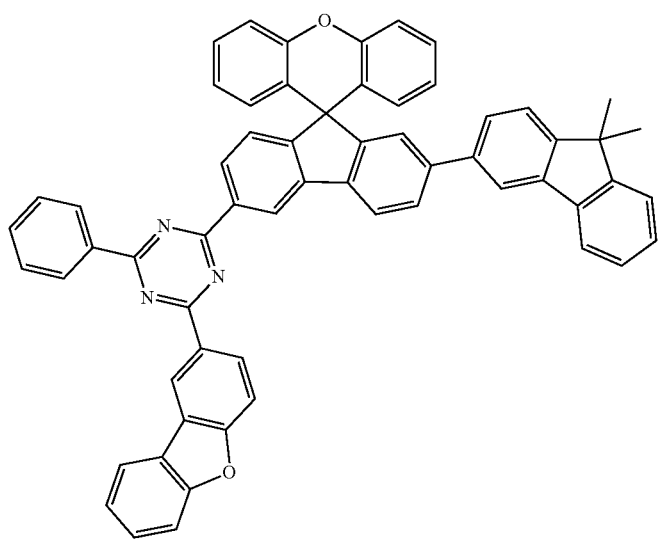
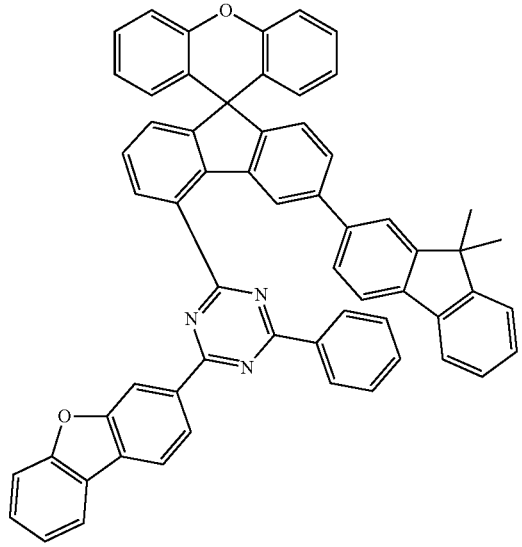
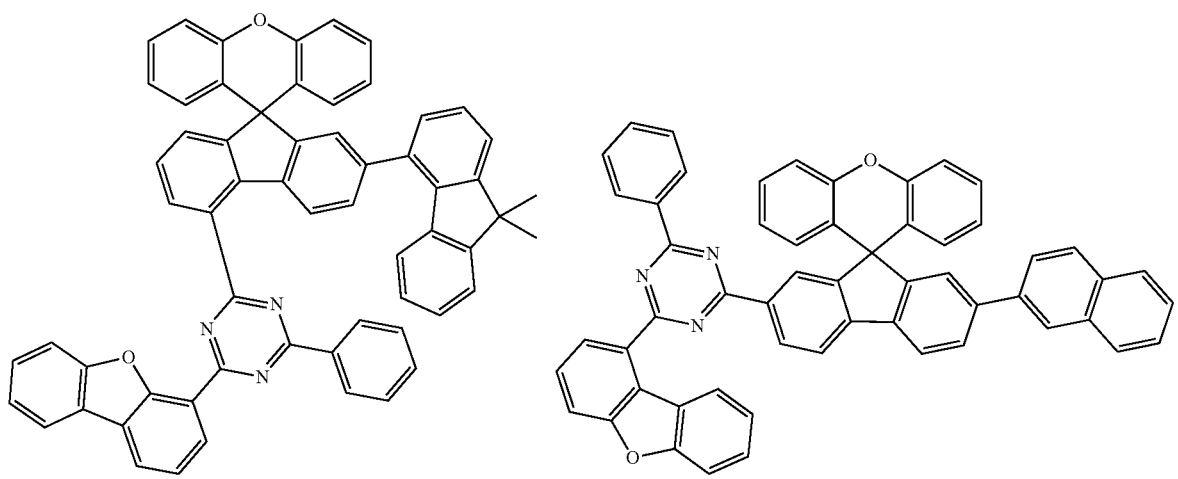
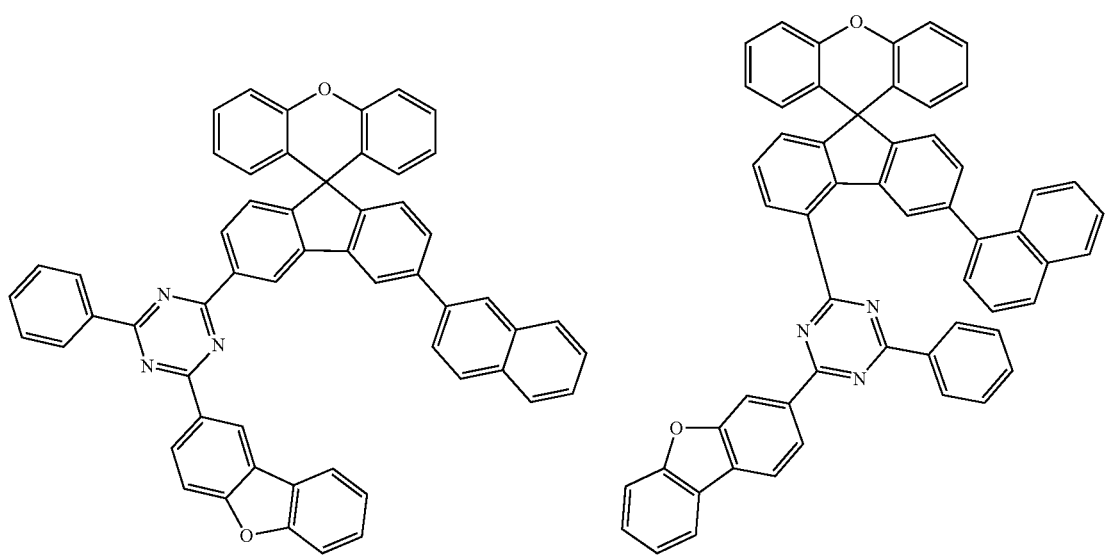

61
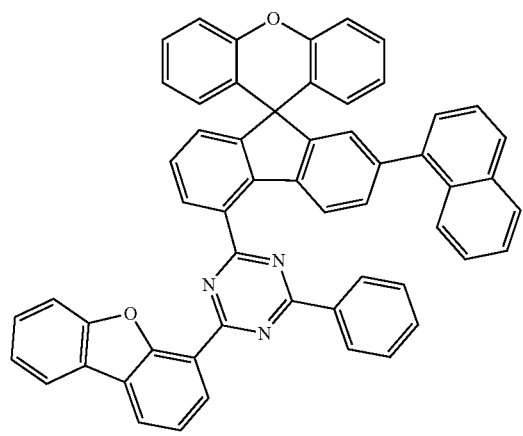
62
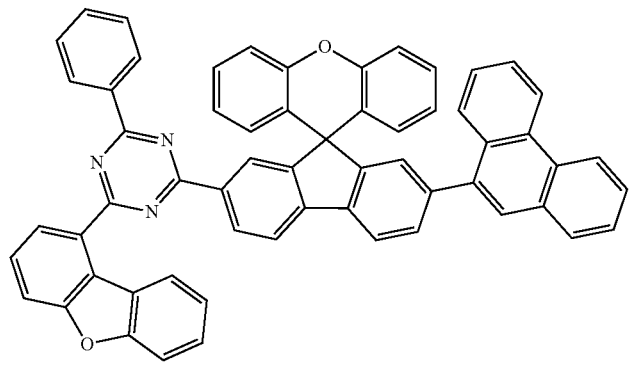
-continued
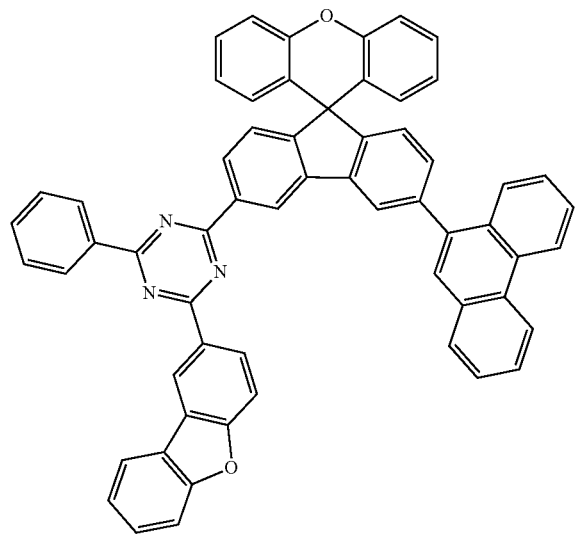
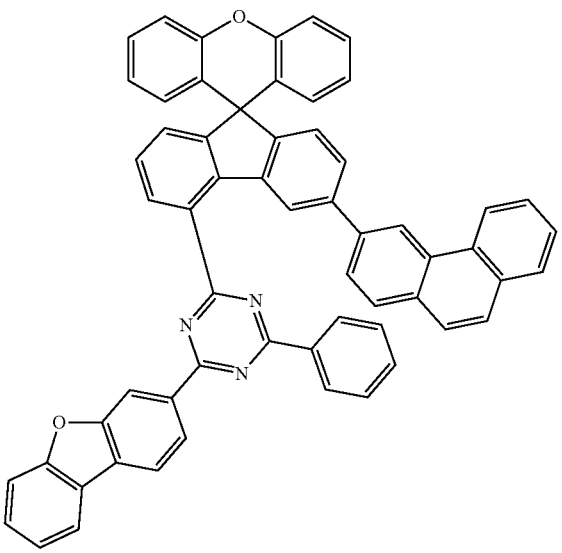
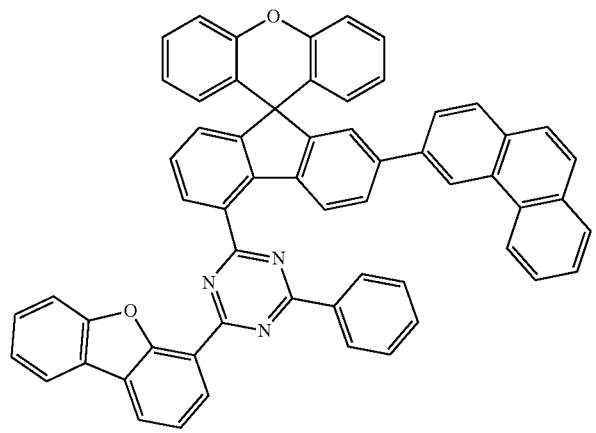

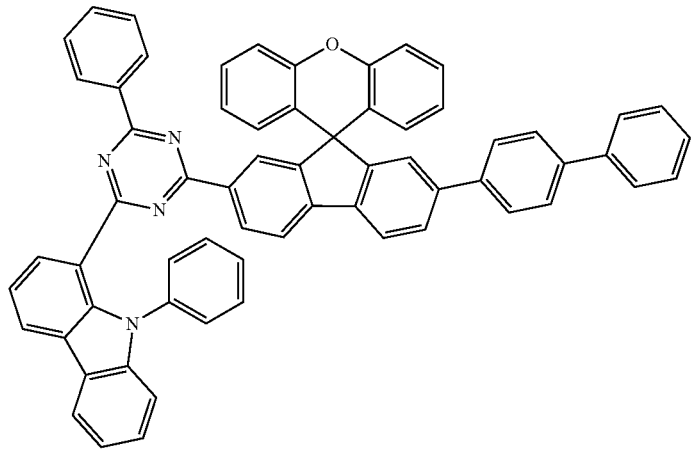
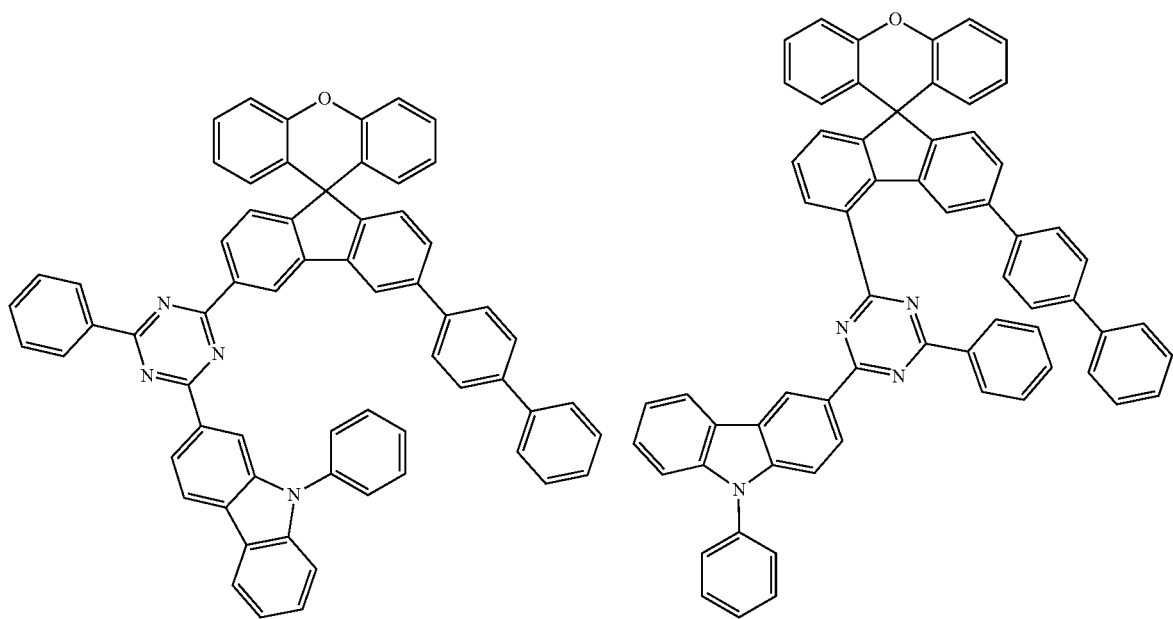
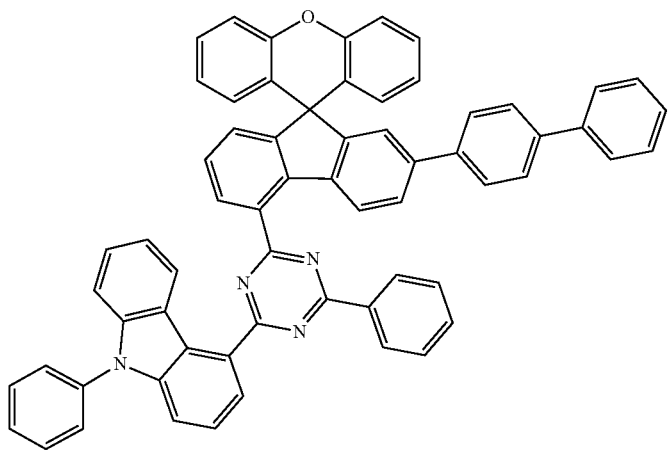

-continued
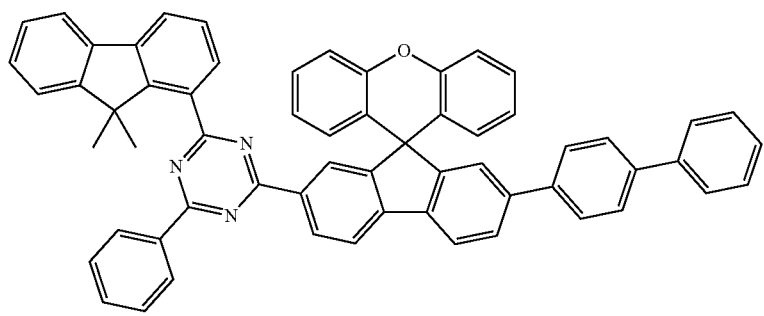
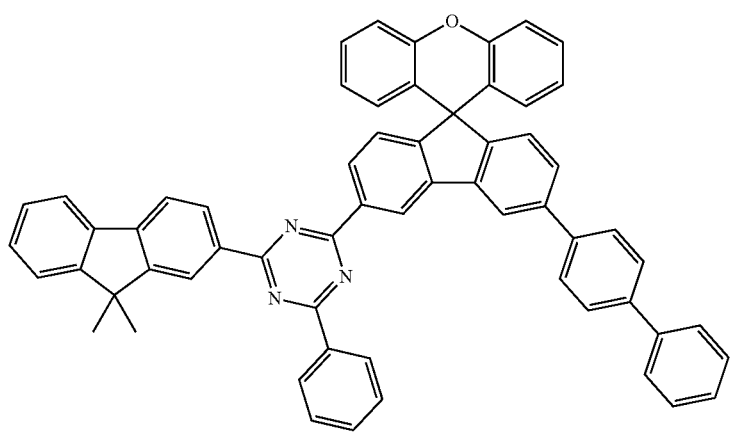
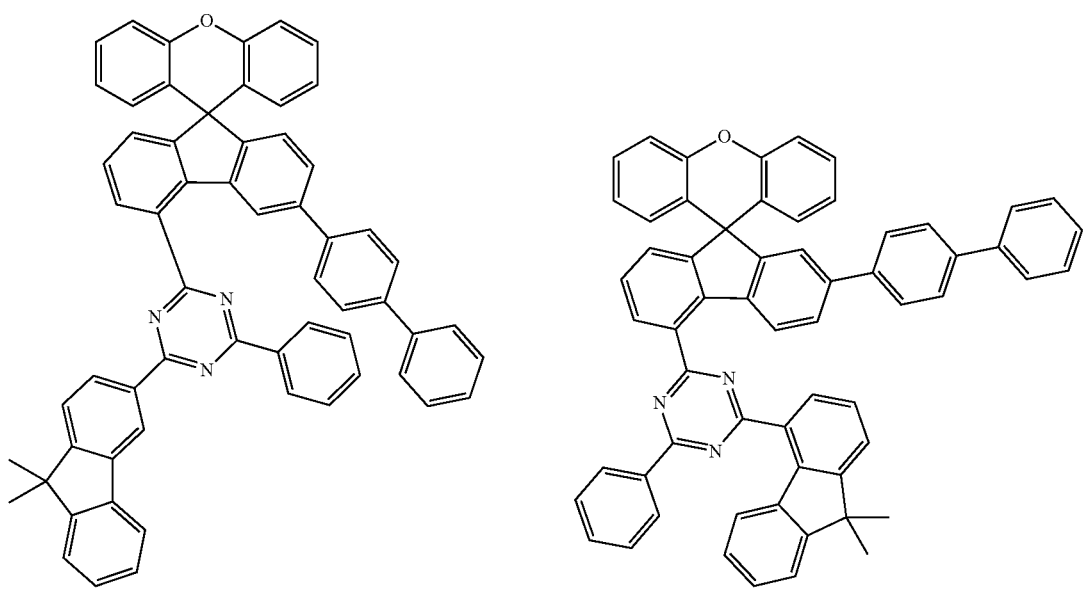

67
68
-continued
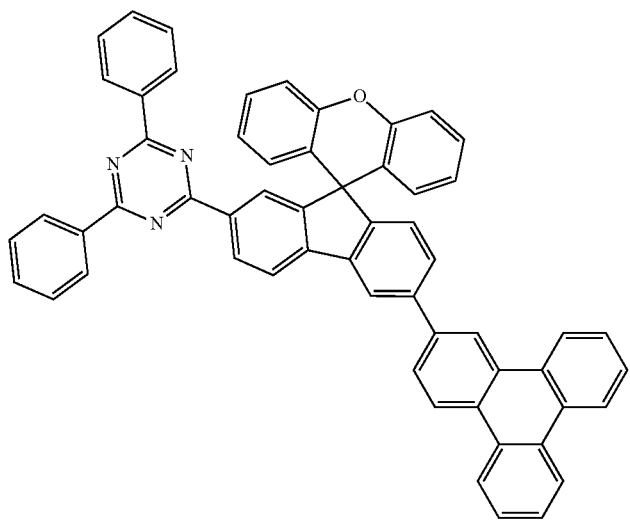
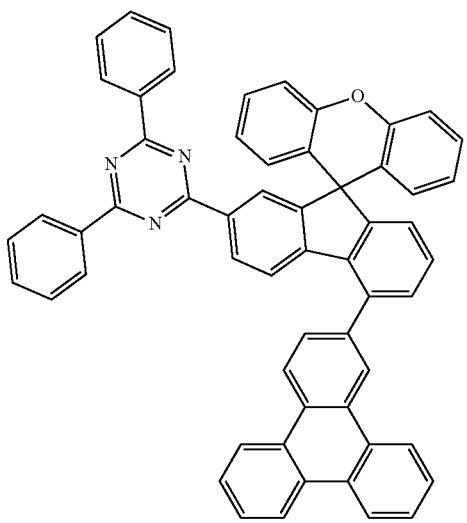
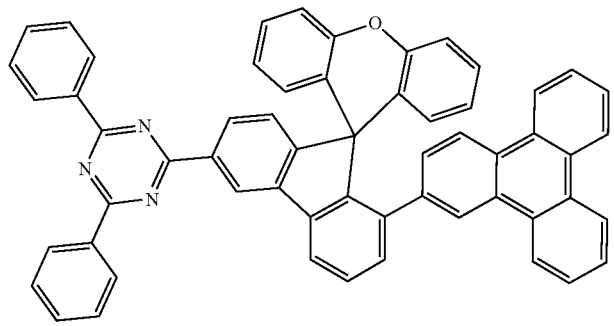
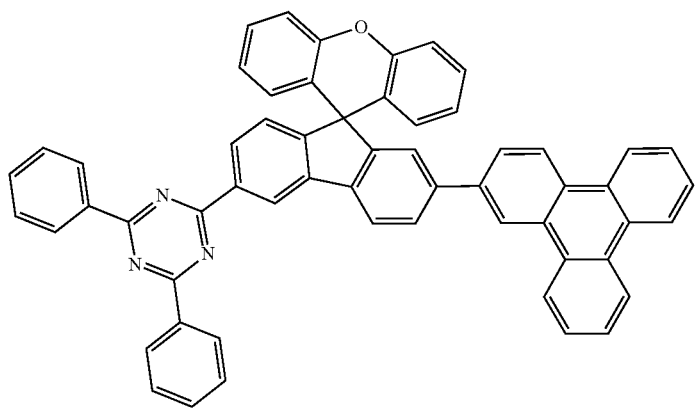
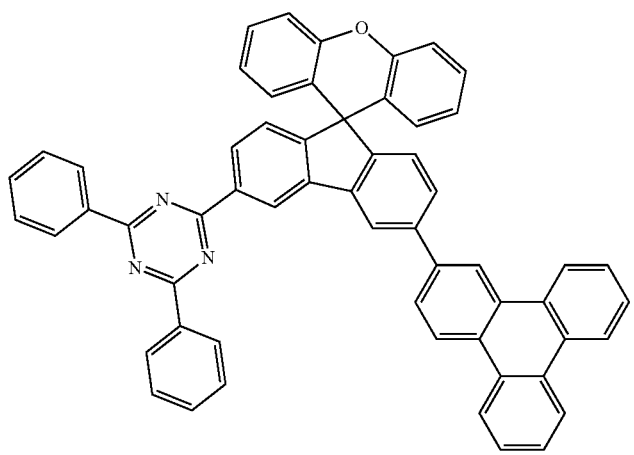

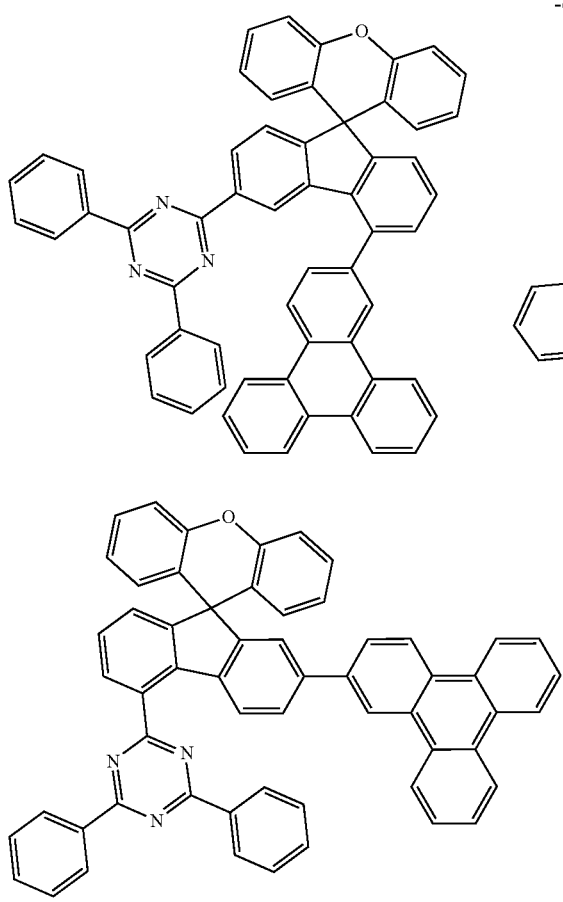

According to one embodiment of the present specification, the compound of Chemical Formula 1 is asymmetric. Being asymmetric refers to a structure in which, with respect to an imaginary baseline made by extending a line connecting X and a spiro bonding site of a core structure as in the following figure, the core structure is substituted with different substituents.

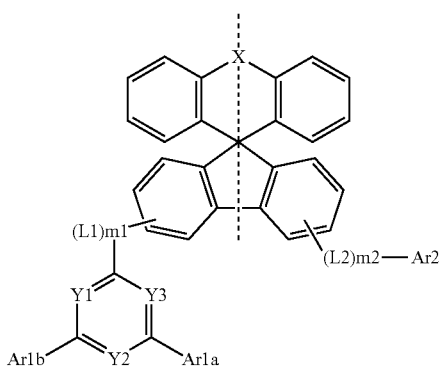

One embodiment of the present specification provides an organic light emitting device including a first electrode; a second electrode provided opposite to the first electrode; and one or more organic material layers provided between the first electrode and the second electrode, wherein one or more layers of the organic material layers include the heterocyclic compound described above.

According to one embodiment of the present specification, the organic material layer of the organic light emitting device of the present specification can be famed in a single layer structure, but can be formed in a multilayer structure in which two or more organic material layers are laminated. For example, the organic light emitting device of the present disclosure can have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include less or more numbers of organic material layers.

For example, the organic light emitting device of the present specification can have structures as illustrated in FIG. 1 and FIG. 2, however, the structure is not limited thereto.

FIG. 1 illustrates a structure of the organic light emitting device (10) in which a first electrode (30), a light emitting layer (40) and a second electrode (50) are consecutively laminated on a substrate (20). FIG. 1 is an exemplary structure of the organic light emitting device according to one embodiment of the present specification, and other organic material layers can be further included.

FIG. 2 illustrates a structure of the organic light emitting device (11) in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of the organic light emitting device according to an embodiment of the present specification, and other organic material layers can be further included.

According to one embodiment of the present specification, the organic material layer includes a light emitting layer, and the light emitting layer includes the heterocyclic compound of Chemical Formula 1.

According to one embodiment of the present specification, the light emitting layer can include additional light emitting layer materials in addition to the heterocyclic compound of Chemical Formula 1.

According to one embodiment of the present specification, the light emitting layer includes a host and a dopant.

According to one embodiment of the present specification, the light emitting layer includes a host of the following Chemical Formula A:

[Chemical Formula A]

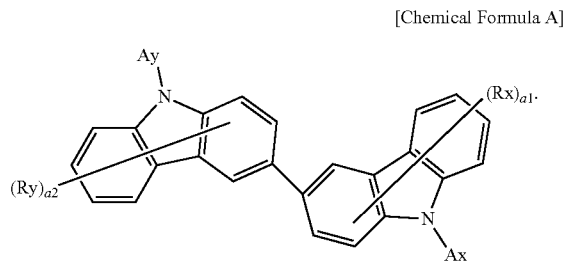

In Chemical Formula A:

Ax and Ay are the same as or different from each other, and each independently is a substituted or unsubstituted aryl group, or a substituted or unsubstituted heteroaryl group;

Rx and Ry are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and a1 and a2 are an integer of 0 to 7, and when a1 or a2 is a plural number, substituents in the parentheses are the same as or different from each other.

According to one embodiment of the present specification, the light emitting layer includes a dopant, and the dopant is a metal complex.

According to one embodiment of the present specification, the light emitting layer includes an iridium-based dopant.

According to one embodiment of the present specification, the light emitting layer includes the heterocyclic compound of Chemical Formula 1 and the host in a mass ratio of 1:10 to 10:1.

According to one embodiment of the present specification, the light emitting layer includes the host and the dopant in a mass ratio of 1:10 to 10:1.

According to one embodiment of the present specification, the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound of Chemical Formula 1.

In one embodiment of the present specification, when using the heterocyclic compound of Chemical Formula 1 in the organic material layer capable of carrying out electron injection and electron transfer at the same time, an n-type dopant used in the art can be mixed thereto and used.

In one embodiment of the present specification, when further including an n-type dopant in the electron transfer layer, the electron injection layer or the layer carrying out electron injection and electron transfer at the same time in addition to the compound of Chemical Formula 1, the compound of Chemical Formula 1 and the n-type dopant can have a weight ratio of 1:100 to 100:1. Specifically, the weight ratio can be from 1:10 to 10:1. More specifically, the weight ratio can be 1:1.

In one embodiment of the present specification, the n-type dopant can be a metal complex and the like, and an alkali metal such as Li, Na, K, Rb, Cs or Fr; an alkaline-earth metal such as Be, Mg, Ca, Sr, Ba or Ra; a rare-earth metal such as La, Ce, Pr, Nd, Sm, Eu, Tb, Th, Dy, Ho, Er, Em, Gd, Yb, Lu, Y or Mn; or a metal compound including one or more metals of the above-mentioned metals can be used, however, the n-type dopant is not limited thereto, and those known in the art can be used. According to one embodiment, the electron transfer layer, the electron injection layer, or the layer carrying out electron injection and electron transfer at the same time including the compound of Chemical Formula 1 can further include LiQ.

According to one embodiment of the present specification, the organic material layer includes a hole blocking layer, and the hole blocking layer includes the heterocyclic compound of Chemical Formula 1.

According to one embodiment of the present specification, the organic material layer includes an electron control layer, and the electron control layer includes the heterocyclic compound of Chemical Formula 1.

According to one embodiment of the present specification, the organic material layer can further include one or more layers selected from the group consisting of a hole injection layer, a hole transfer layer, a light emitting layer, an electron transfer layer and an electron injection layer.

The organic light emitting device of the present specification can be manufactured using materials and methods known in the art, except that one or more layers of the organic material layers include the heterocyclic compound of the present specification, that is, the heterocyclic compound of Chemical Formula 1.

When the organic light emitting device includes a plurality of organic material layers, the organic material layers can be formed with materials the same as or different from each other.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as sputtering or e-beam evaporation, and foiling an organic material layer including a hole injection layer, a hole transfer layer, a light emitting layer and an electron transfer layer thereon, and then depositing a material capable of being used as a second electrode thereon. In addition to such a method, the organic light emitting device can also be manufactured by consecutively depositing a second electrode material, an organic material layer and a first electrode material on a substrate. In addition, the heterocyclic compound of Chemical Formula 1 can be famed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof, and multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer receiving holes from a hole injection layer and transferring the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$), carbazole series compounds, dimerized styryl compounds, BAlq, 10-hydroxybenzoquinoline-metal compounds, benzoxazole, benzothiazole and benzimidazole series compounds, poly(p-phenylenevinylene) (PPV) series polymers, spiro compounds, polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be used, however, the metal complex is not limited thereto.

The electron transfer layer is a layer receiving electrons from an electron injection layer and transferring the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline, complexes including $Alq_3$, organic radical compounds, hydroxyflavon-metal complexes, and the like, but are not limited thereto. The electron transfer layer can be used together with any desired cathode material as used in the art. Particularly, examples of the suitable cathode material can include common materials having low work function and having an aluminum layer or a silver layer following. Specifically, cesium, barium, calcium, ytterbium and samarium are included, and in each case, an aluminum layer or a silver layer follows.

The electron injection layer is a layer injecting electrons from an electrode, and compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The hole blocking layer is layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxyquinolinato)-aluminum, tris(8-hydroxyquinolinato)gallium, bis(10-hydroxybenzo-[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)-gallium and the like, but is not limited thereto.

The organic light emitting device according to the present specification can be a top-emission type, a bottom-emission type or a dual-emission type depending on the materials used.

The compound according to one embodiment of the present specification can be prepared using preparation methods to describe below.

<Synthesis Example 1>Synthesis of Compound 1

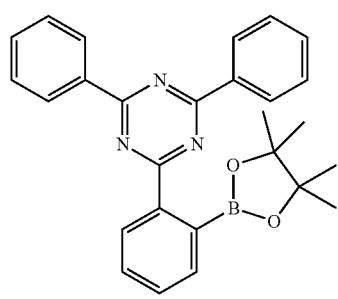

1a

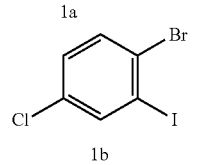

1b

TTP, K₂CO₃ / THF, H₂O →

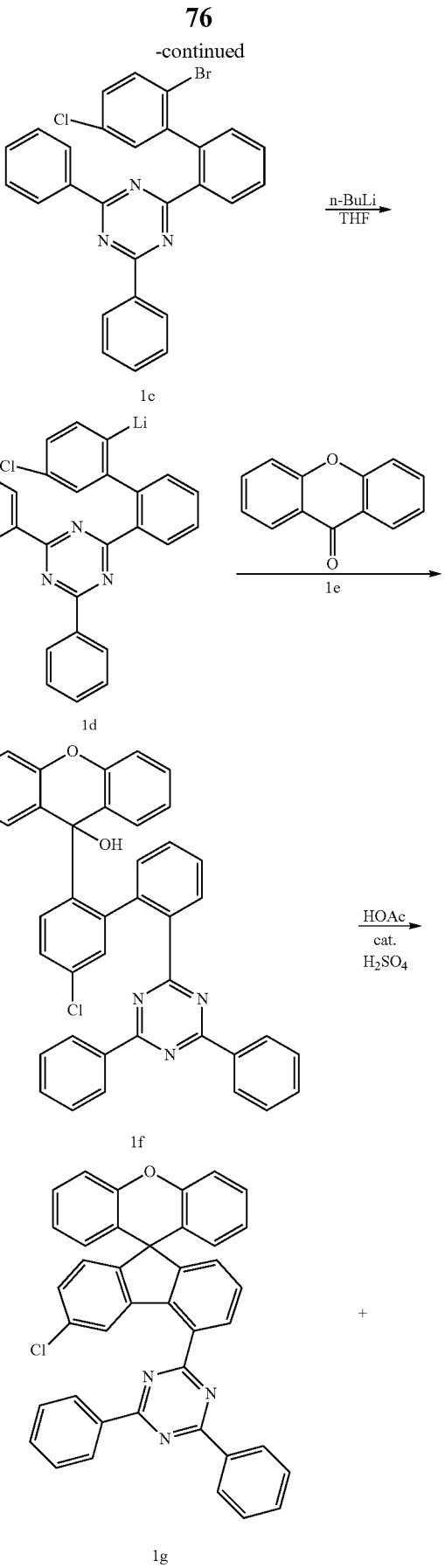

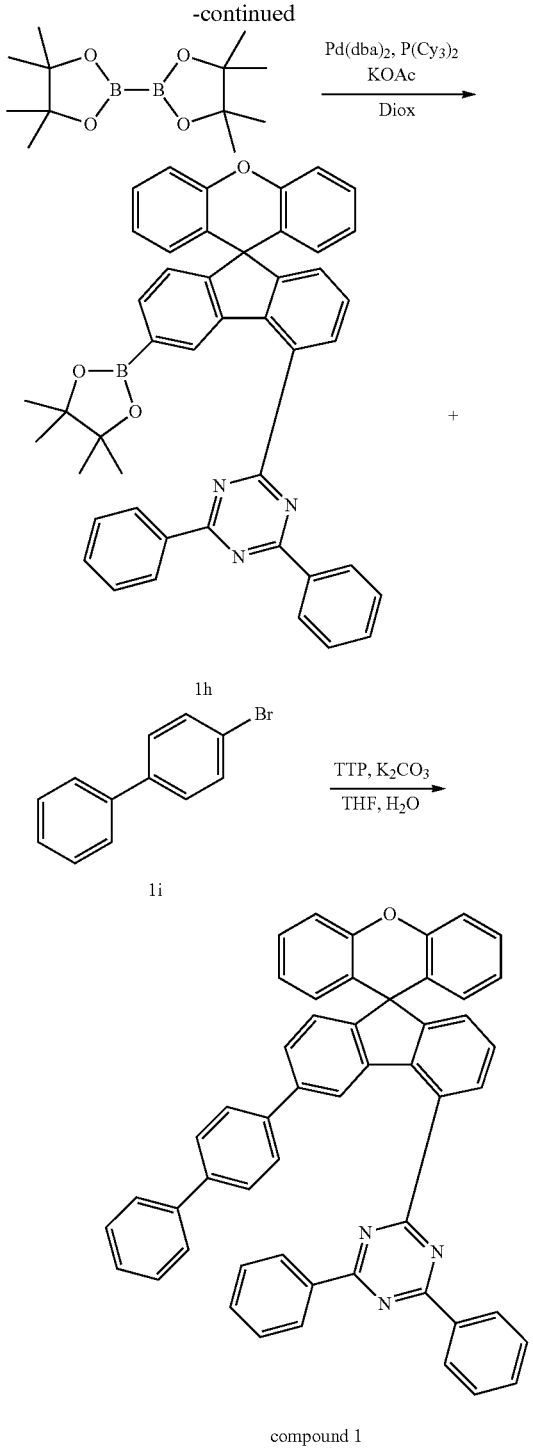

1) Preparation of Chemical Formula 1c

While adding Chemical Formula 1a (50 g, 115 mmol) and Chemical Formula 1b (36 g, 115 mmol) to tetrahydrofuran (300 ml) and stirring the result under nitrogen atmosphere, potassium carbonate (48 g, 345 mmol) dissolved in water was added thereto. After that, the result was heated, and tetrakis-(triphenylphosphine)palladium(0) (4 g, 3 mmol) was slowly added thereto under reflux. After that, the result was reacted for approximately 9 hours, and the reaction was terminated. After the reaction was terminated, the temperature was lowered to room temperature, and the organic layer was separated and then distilled. After that, the distillate was extracted twice with chloroform and water, then the organic layer was vacuum distilled again, and purified using column chromatography (chloroform:hexane) to prepare Chemical Formula 1c (44 g, 77%).

2) Preparation of Chemical Formula 1g

Chemical Formula 1c (30.0 g, 60 mmol) was introduced to anhydrous tetrahydrofuran (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature, and the result was reacted for 1 hour. After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereto, then the water layer and the organic layer were separated, and the organic layer was vacuum distilled to obtain Chemical Formula 1f. This was introduced to acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 1 g (21 g, 57%).

3) Preparation of Chemical Formula 1h

Chemical Formula 1g (20 g, 33 mmol), bis(pinacolato) diboron (9.4 g, 37 mmol) and potassium acetate (10 g, 100 mmol) were mixed under nitrogen atmosphere, dioxane (200 ml) was added thereto, and the result was heated while stirring. Under reflux, bis(dibenzylidineacetone)palladium (1.2 g, 2 mmol) and tricyclohexylphosphine (1.1 g, 4 mmol) were introduced thereto, and the result was heated and stirred for 13 hours. After the reaction was terminated, the temperature was lowered to room temperature, and the result was filtered. Water was poured to the filtrate, the result was extracted with chloroform, and the organic layer was dried using anhydrous magnesium sulfate. The result was vacuum distilled and recrystallized with ethanol to prepare Chemical Formula 1h (16 g, 69%).

4) Preparation of Compound 1

Chemical Formula 1h (10 g, 15 mmol) and Chemical Formula 1i (3.4 g, 15 mmol) were introduced to tetrahydrofuran (100 ml) under nitrogen atmosphere, and the result was stirred and refluxed. After that, potassium carbonate (6 g, 44 mmol) dissolved in water (20 ml) was introduced thereto, and after sufficiently stirring the result, tetrakistriphenyl-phosphinopalladium (0.5 g, 0.4 mmol) was introduced thereto. The result was reacted for 8 hours, and then, after lowering the temperature to room temperature, filtered. The filtered material was extracted with chloroform and water, and the organic layer was dried using magnesium sulfate. After that, the organic layer was vacuum distilled and recrystallized using ethyl acetate. The produced solids were filtered and then dried to prepare Compound 1 (5.1 g, 49%).

MS: [M+H]+=716

<Synthesis Example 2>Synthesis of Compound 2
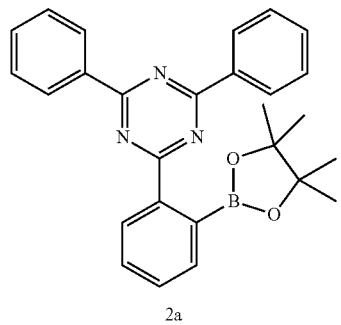
2a
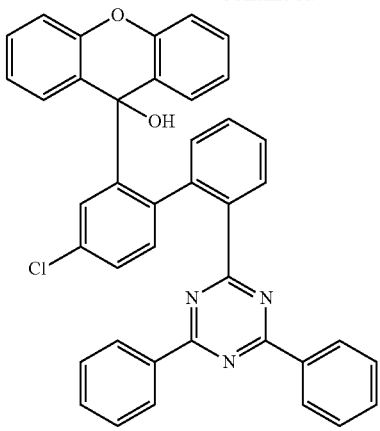
2f
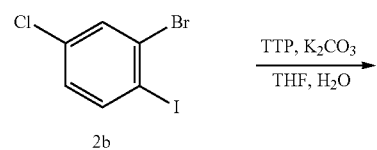
2b
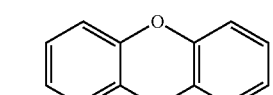
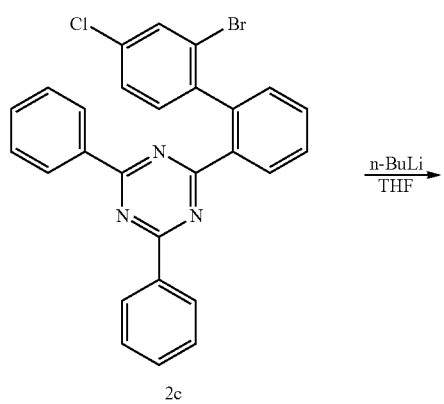
2c
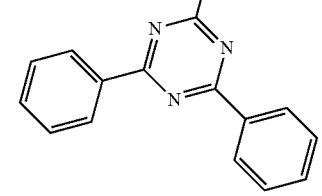
2g
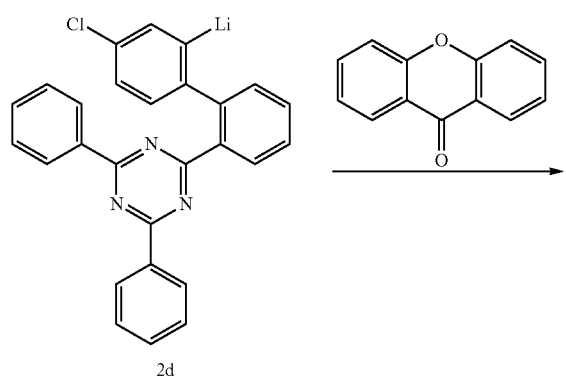
2d
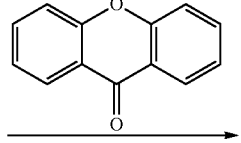
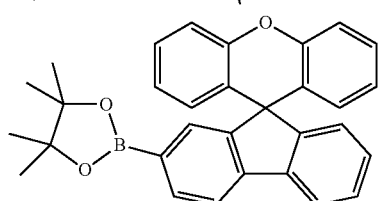
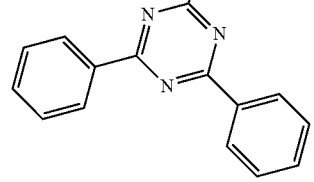
2h

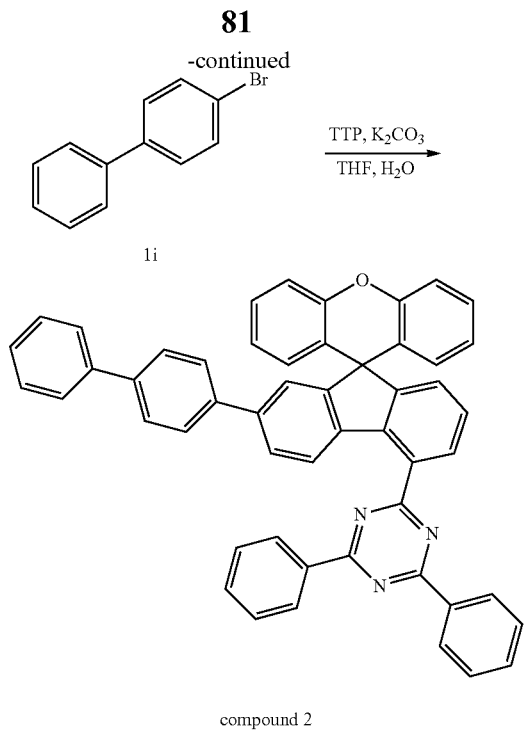

compound 2

1) Preparation of Chemical Formula 2C

While adding Chemical Formula 2a (50 g, 115 mmol) and Chemical Formula 2B (36 g, 115 mmol) to tetrahydrofuran (300 ml) and stirring the result under nitrogen atmosphere, potassium carbonate (48 g, 345 mmol) dissolved in water was added thereto. After that, the result was heated, and tetrakis-(triphenylphosphine)palladium(0) (4 g, 3 mmol) was slowly added thereto under reflux. After that, the result was reacted for approximately 9 hours, and the reaction was terminated. After the reaction was terminated, the temperature was lowered to room temperature, and the organic layer was separated and then distilled. After that, the distillate was extracted twice with chloroform and water, then the organic layer was vacuum distilled again, and purified using column chromatography (chloroform:hexane) to prepare Chemical Formula 2C (58 g, 84%).

2) Preparation of Chemical Formula 2g

Chemical Formula 2c (30.0 g, 60 mmol) was introduced to anhydrous tetrahydrofuran (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature, and the result was reacted for 1 hour. After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereto, then the water layer and the organic layer were separated, and the organic layer was vacuum distilled to obtain Chemical Formula 2f. This was introduced to acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 2g (24 g, 66%).

3) Preparation of Chemical Formula 2h

Chemical Formula 2g (20 g, 33 mmol), bis(pinacolato)diboron (9.4 g, 37 mmol) and potassium acetate (10 g, 100 mmol) were mixed under nitrogen atmosphere, dioxane (200 ml) was added thereto, and the result was heated while stirring. Under reflux, bis(dibenzylidineacetone)palladium (1.2 g, 2 mmol) and tricyclohexylphosphine (1.1 g, 4 mmol) were introduced thereto, and the result was heated and stirred for 13 hours. After the reaction was terminated, the temperature was lowered to room temperature, and the result was filtered. Water was poured to the filtrate, the result was extracted with chloroform, and the organic layer was dried using anhydrous magnesium sulfate. The result was vacuum distilled and recrystallized with ethanol to prepare Chemical Formula 2h (19 g, 81%).

4) Preparation of Compound 2

Chemical Formula 2h (10 g, 15 mmol) and Chemical Formula 1i (3.4 g, 15 mmol) were introduced to tetrahydrofuran (100 ml) under nitrogen atmosphere, and the result was stirred and refluxed. After that, potassium carbonate (6 g, 44 mmol) dissolved in water (20 ml) was introduced thereto, and after sufficiently stirring the result, tetrakistriphenyl-phosphinopalladium (0.5 g, 0.4 mmol) was introduced thereto. The result was reacted for 8 hours, and then, after lowering the temperature to room temperature, filtered. The filtered material was extracted with chloroform and water, and the organic layer was dried using magnesium sulfate. After that, the organic layer was vacuum distilled and recrystallized using ethyl acetate. The produced solids were filtered and then dried to prepare Compound 2 (6.2 g, 60%).

MS: [M+H]+=716

<Synthesis Example 3> Synthesis of Compound 3

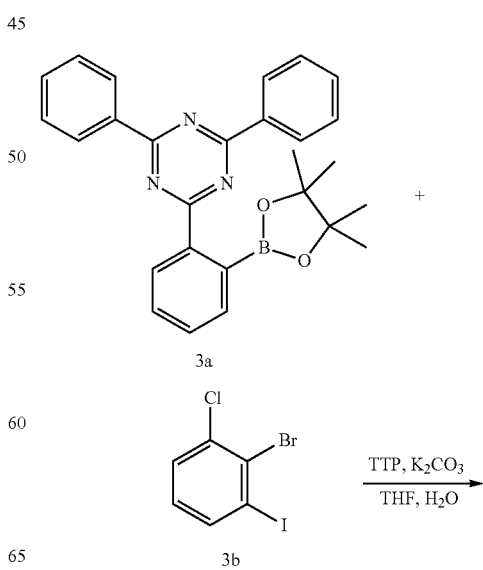

83
-continued
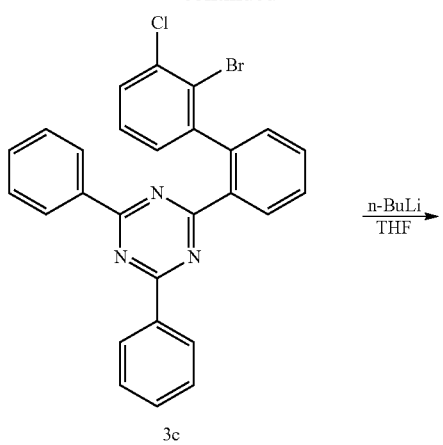
3c
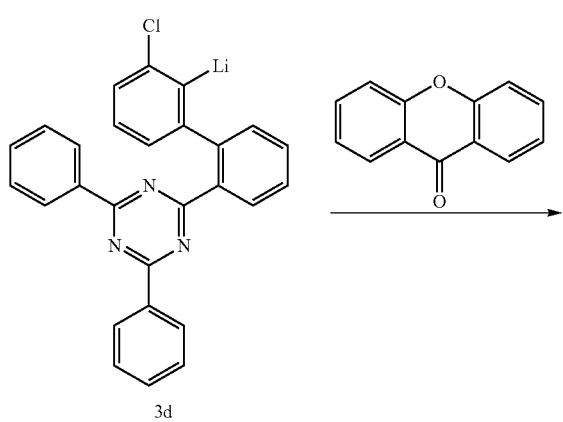
3d
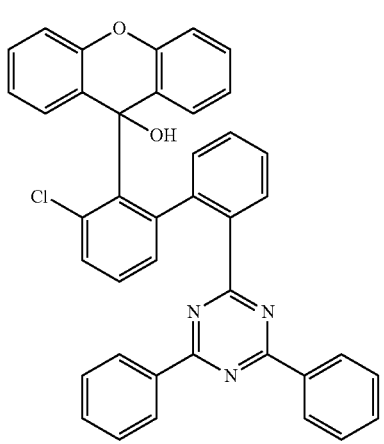
3f
84
-continued
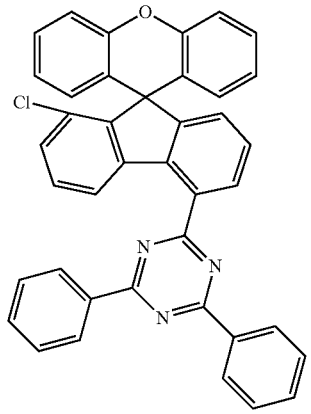
3g
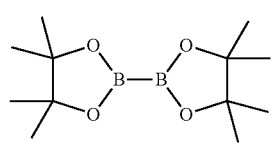
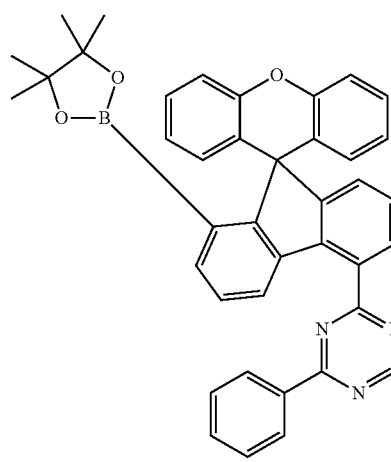
3h
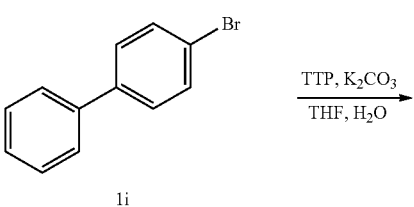
1i

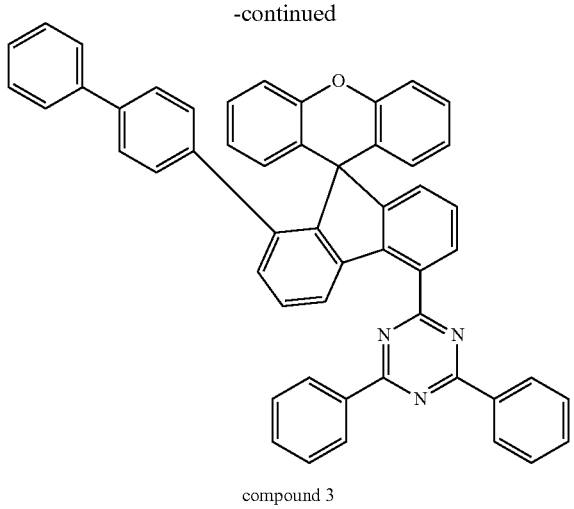

compound 3

1) Preparation of Chemical Formula 3C

While adding Chemical Formula 3a (50 g, 115 mmol) and Chemical Formula 3B (36 g, 115 mmol) to tetrahydrofuran (300 ml) and stirring the result under nitrogen atmosphere, potassium carbonate (48 g, 345 mmol) dissolved in water was added thereto. After that, the result was heated, and tetrakis(triphenyl-phosphine)palladium(0) (4 g, 3 mmol) was slowly added thereto under reflux. After that, the result was reacted for approximately 9 hours, and the reaction was terminated. After the reaction was terminated, the temperature was lowered to room temperature, and the organic layer was separated and then distilled. After that, the distillate was extracted twice with chloroform and water, then the organic layer was vacuum distilled again, and purified using column chromatography (chloroform:hexane) to prepare Chemical Formula 3C (48 g, 70%).

2) Preparation of Chemical Formula 3g

Chemical Formula 3c (30.0 g, 60 mmol) was introduced to anhydrous tetrahydrofuran (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature, and the result was reacted for 1 hour. After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereto, then the water layer and the organic layer were separated, and the organic layer was vacuum distilled to obtain Chemical Formula 3f. This was introduced to acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 3g (21 g, 57%).

3) Preparation of Chemical Formula 3h

Chemical Formula 3g (20 g, 33 mmol), bis(pinacolato)diboron (9.4 g, 37 mmol) and potassium acetate (10 g, 100 mmol) were mixed under nitrogen atmosphere, dioxane (200 ml) was added thereto, and the result was heated while stirring. Under reflux, bis(dibenzylidineacetone)palladium (1.2 g, 2 mmol) and tricyclohexylphosphine (1.1 g, 4 mmol) were introduced thereto, and the result was heated and stirred for 13 hours. After the reaction was terminated, the temperature was lowered to room temperature, and the result was filtered. Water was poured to the filtrate, the result was extracted with chloroform, and the organic layer was dried using anhydrous magnesium sulfate. The result was vacuum distilled and recrystallized with ethanol to prepare Chemical Formula 3h (14 g, 60%).

4) Preparation of Compound 3

Chemical Formula 3h (10 g, 15 mmol) and Chemical Formula 1i (3.4 g, 15 mmol) were introduced to tetrahydrofuran (100 ml) under nitrogen atmosphere, and the result was stirred and refluxed. After that, potassium carbonate (6 g, 44 mmol) dissolved in water (20 ml) was introduced thereto, and after sufficiently stirring the result, tetrakistriphenyl-phosphinopalladium (0.5 g, 0.4 mmol) was introduced thereto. The result was reacted for 8 hours, and then, after lowering the temperature to room temperature, filtered. The filtered material was extracted with chloroform and water, and the organic layer was dried using magnesium sulfate. After that, the organic layer was vacuum distilled and recrystallized using ethyl acetate. The produced solids were filtered and then dried to prepare Compound 3 (4.2 g, 40%).

MS: [M+H]+=716

Hereinafter, the present specification will be described in detail with reference to examples. However, examples according to the present specification can be modified to various other forms, and the scope of the present specification is not to be construed as being limited to the examples described below. Examples of the present specification are provided in order to more fully describe the present specification to those having average knowledge in the art.

EXPERIMENTAL EXAMPLES

Experimental Example 1

A glass substrate on which indium tin oxide (ITO) was coated as a thin film to a thickness of 1,300 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was foiled by thermal vacuum depositing the following HI-1 compound to a thickness of 50 Å. A hole transfer layer was formed on the hole injection layer by thermal vacuum depositing the following HT-1 compound to a thickness of 250 Å, and on the HT-1 deposited film, an electron blocking layer was formed by vacuum depositing the following HT-2 compound to a thickness of 50 Å. On the HT-2 deposited film, a light emitting layer was famed to a thickness of 400 Å by co-depositing Compound 1 prepared above in Example 1, the following YGH-1 compound and phosphorescent dopant YGD-1 in a weight ratio of 44:44:12 as the light emitting layer. An electron transfer layer was formed on the light emitting layer by vacuum depositing the following ET-1 compound to a thickness of 250 Å, and on the electron transfer layer, an electron injection layer having a thickness of 100 Å was formed by vacuum depositing the following ET-2 compound and Li in a weight ratio of 98:2. A cathode was formed on the electron injection layer by depositing aluminum to a thickness of 1000 Å.

HI-1

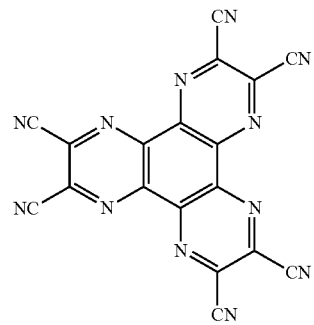

HT-1

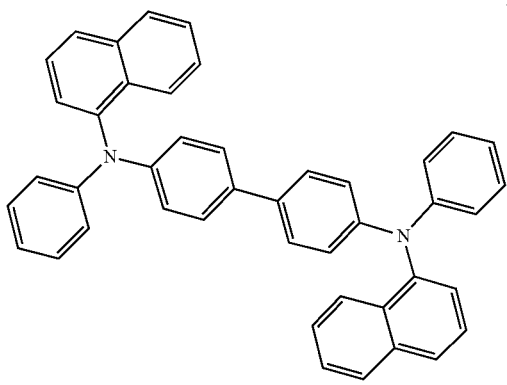

HT-2

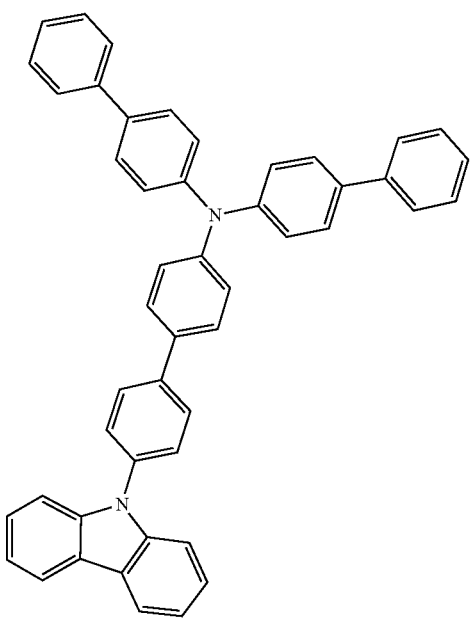

-continued

YGH-1

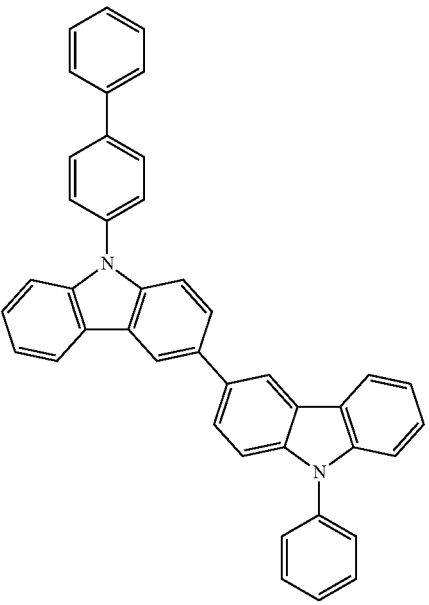

YGD-1

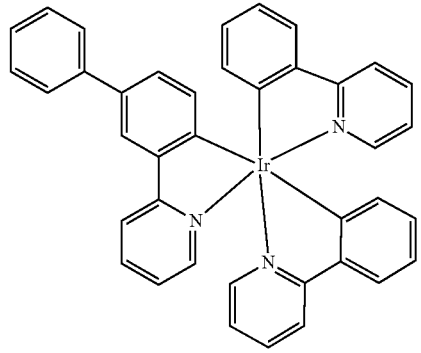

ET-1

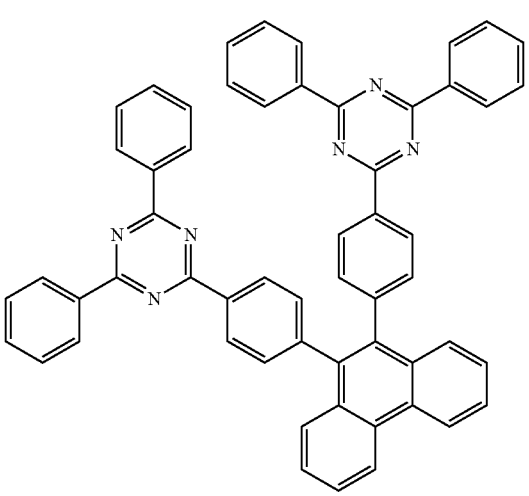

ET-2

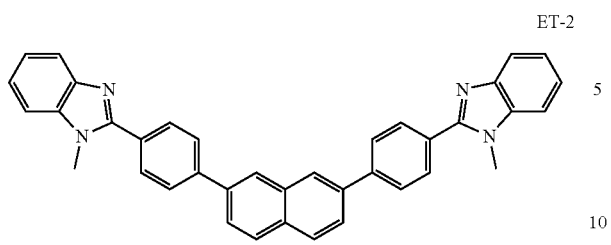

In the above-mentioned processes, the deposition rates of the organic materials were maintained at 0.4 Å/sec to 0.7 Å/sec, the deposition rate of the aluminum was maintained at 2 Å/sec, and the degree of vacuum during the deposition was maintained at $1 \times 10^{-7}$ torr to $5 \times 10^{-8}$ torr.

Experimental Examples 2 and 3

Organic light emitting devices were manufactured in the same manner as in Experimental Example 1 except that compounds described in the following Table 1 were each used instead of Compound 1 of Example 1 in Experimental Example 1.

Comparative Experimental Examples 1 to 5

Organic light emitting devices were manufactured in the same manner as in Experimental Example 1 except that compounds described in the following Table 1 were each used instead of Compound 1 of Example 1 in Experimental Example 1. Compounds of CE1 to CE5 of the following Table 1 are as follows.

CE1

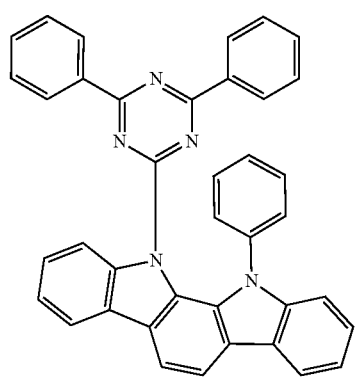

CE2

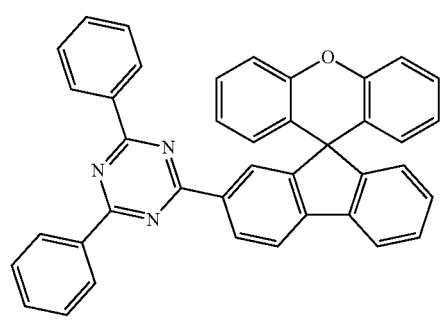

CE3

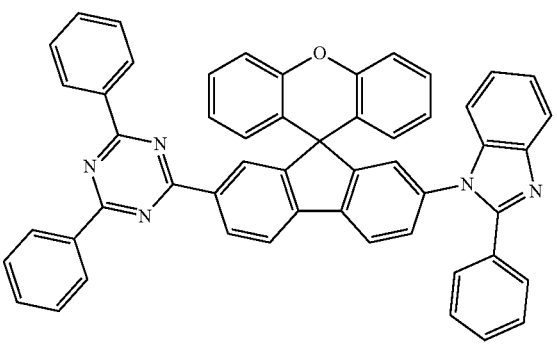

CE4

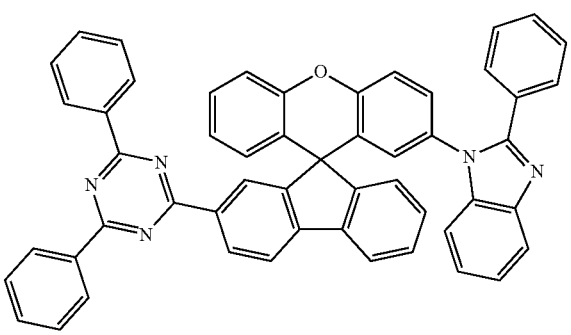

CE5

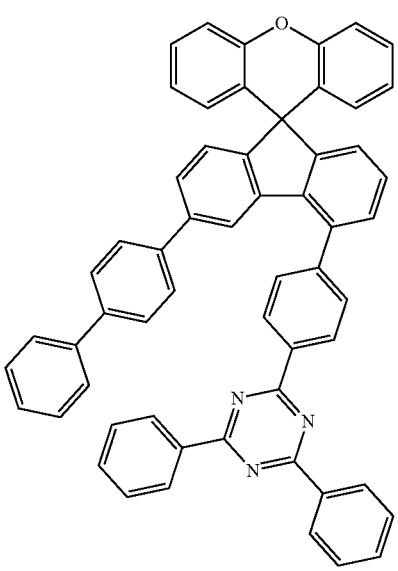

For the organic light emitting devices of the experimental examples and the comparative experimental examples, a voltage and efficiency were measured at current density of 10 mA/cm², and a lifetime was measured at current density of 50 mA/cm², and the results are shown in the following Table 1. Herein, LT95 means times taken to be 95% with respect to initial luminance.

TABLE 1

| Compound | Voltage (V) (@ 10 mA/cm$^2$) | Efficiency (Cd/A) (@ 10 mA/cm$^2$) | Color Coordinate (x, y) | Lifetime (h) (LT$_{95}$ at 50 mA/cm$^2$) |
|---|---|---|---|---|
| Experimental Example 1-1 | Compound 1 | 4.0 | 75 | 0.46, 0.54 | 150 |
| Experimental Example 1-2 | Compound 2 | 3.9 | 74 | 0.46, 0.54 | 140 |
| Experimental Example 1-3 | Compound 3 | 3.9 | 79 | 0.46, 0.53 | 120 |
| Comparative Experimental Example 1 | CE1 | 4.0 | 70 | 0.46, 0.53 | 90 |
| Comparative Experimental Example 2 | CE2 | 4.2 | 75 | 0.44, 0.55 | 30 |
| Comparative Experimental Example 3 | CE3 | 4.3 | 71 | 0.46, 0.52 | 70 |
| Comparative Experimental Example 4 | CE4 | 4.3 | 71 | 0.46, 0.53 | 5 |
| Comparative Experimental Example 5 | CE5 | 3.8 | 72 | 0.45, 0.52 | 100 |

As shown in Table 1, it was identified that, when using the compound of the present disclosure as a light emitting layer material, excellent properties were obtained in terms of efficiency and lifetime compared to the comparative experimental examples.

The compound of the present disclosure includes a spirofluorene xanthene core. As a result, an electron control ability was enhanced, and long lifetime properties were obtained in the organic light emitting device.

In addition, it was seen that, when a substituent of the spirofluorene xanthene core is an aryl group (Ar2) besides triazine, advantageous properties were obtained compared to when it is an electron withdrawing group. This is due to the fact that electron mobility increases when using an aryl group compared to when using an electron withdrawing group.

REFERENCE NUMERALS 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer

The invention claimed is:

1. A heterocyclic compound of Chemical Formula 1:

[Chemical Formula 1]

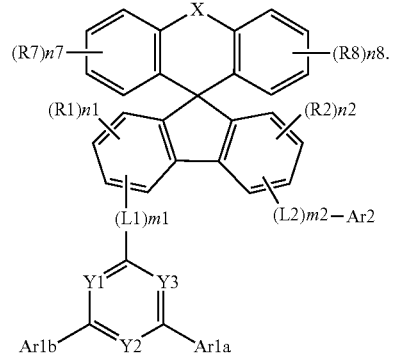

wherein, in Chemical Formula 1:
X is O or S;
Y1 to Y3 are the same as or different from each other, and each independently is N or CR, and at least two of Y1 to Y3 are N;
Ar1a and Ar1b are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;
Ar2 is an aryl group that is selected from among a phenyl group that is unsubstituted or substituted with an alkyl group or a deuterium, a biphenyl group that is unsubstituted or substituted with an alkyl group or a deuterium, a terphenyl group that is unsubstituted or substituted with an alkyl group or a deuterium, a quaterphenyl group that is unsubstituted or substituted with an alkyl group or a deuterium, a fluorenyl group that is unsubstituted or substituted with an alkyl group or a deuterium, a substituted or unsubstituted naphthyl group, a substituted or unsubstituted triphenylene group, a substituted or unsubstituted phenanthrene group, a substituted or unsubstituted chrysene group, a substituted or unsubstituted fluoranthene group, a substituted or unsubstituted pyrene group, a substituted or unsubstituted perylene group, a substituted or unsubstituted benzophenanthrene group, a substituted or unsubstituted benzotetraphene group, or a substituted or unsubstituted tetraphene group;
L1 is a direct bond;

L2 is a direct bond or a substituted or unsubstituted arylene group;

R, R1, R2, R7 and R8 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and n1 and n2 are each independently an integer of 0 to 3, n7 and n8 are each independently an integer of 0 to 4, m1 is 1, and m2 is an integer of 1 or 2, and when n1, n2, n7 and n8 are each an integer of 2 or greater, substituents in the parentheses are the same as or different from each other, and when m2 is an integer of 2, substituents in the parentheses are the same as or different from each other.

2. The heterocyclic compound of claim 1, wherein Ar1a and Ar1b are the same as or different from each other, and each independently is one selected from among the following structural formulae:

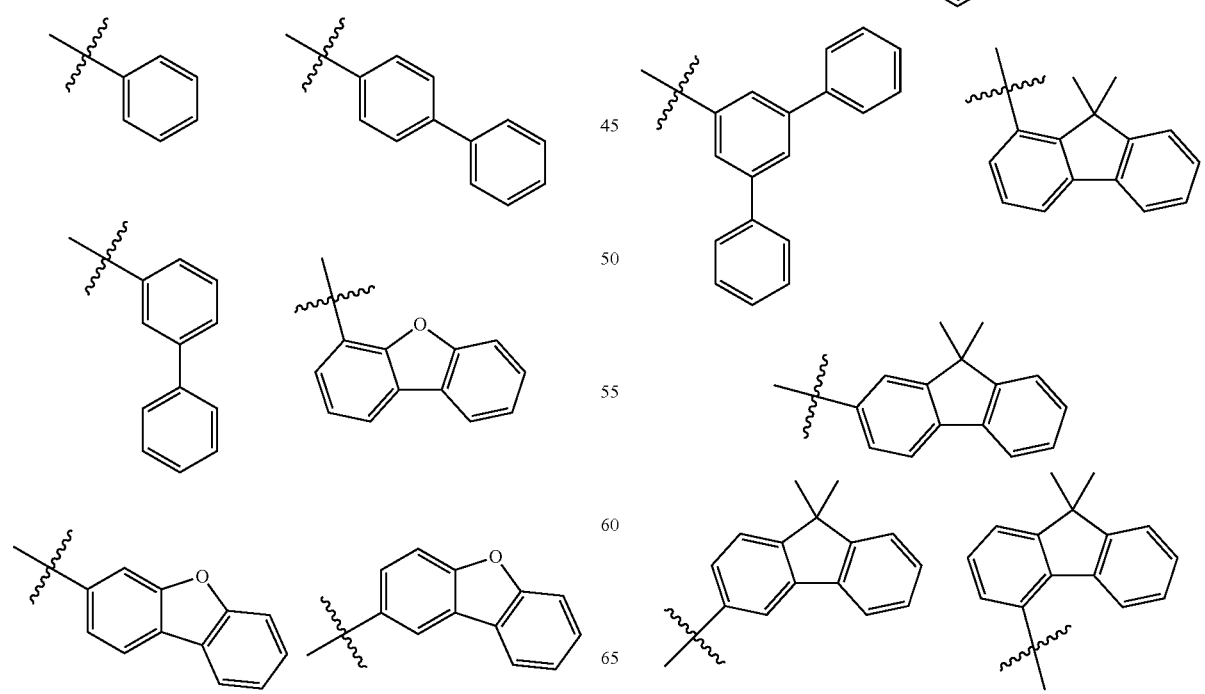

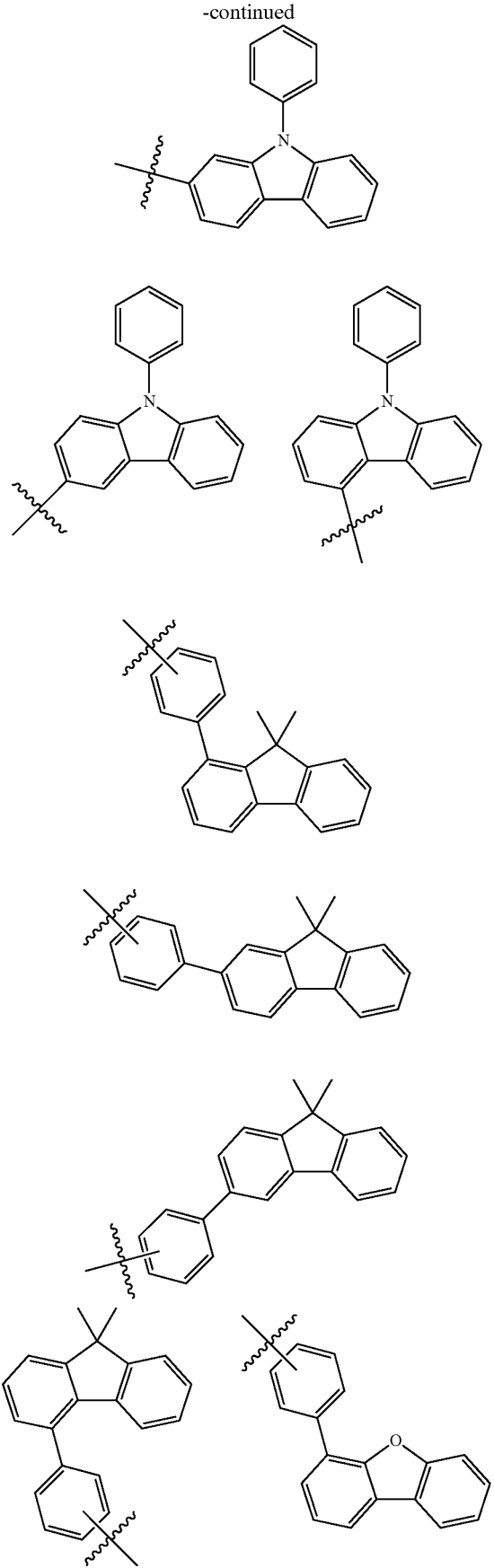
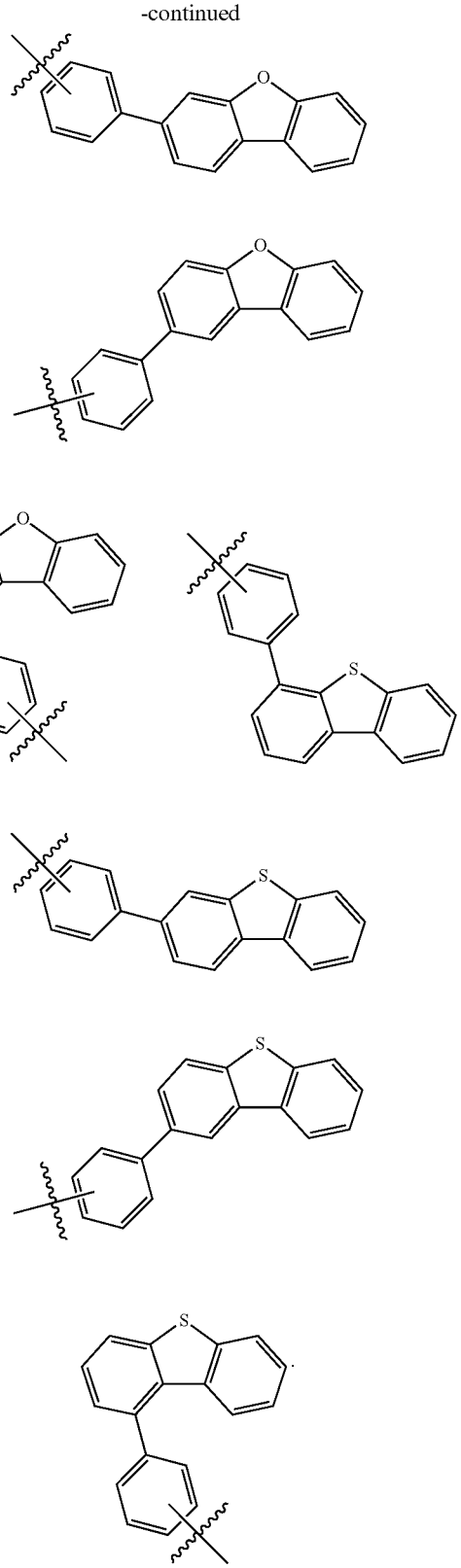
3. The heterocyclic compound of claim 1, wherein Chemical Formula 1 is one selected from among the following Chemical Formulae 1-1 to 1-16:

[Chemical Formula 1-1]
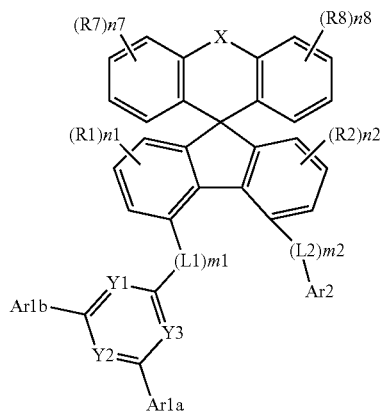
[Chemical Formula 1-2]
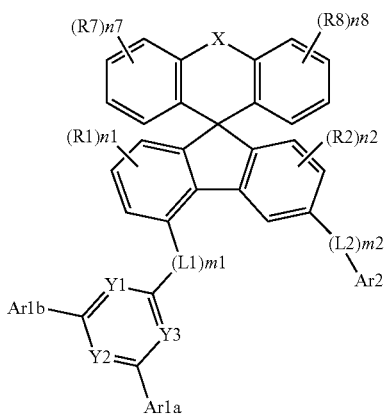
[Chemical Formula 1-3]
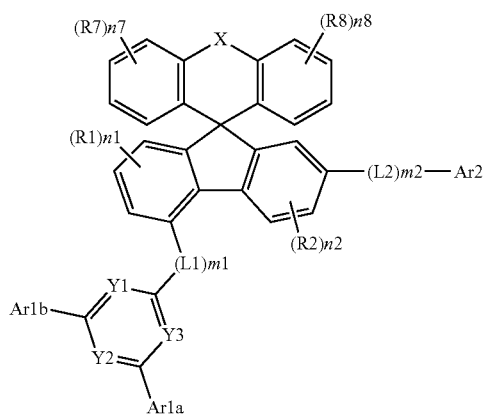
-continued
[Chemical Formula 1-4]
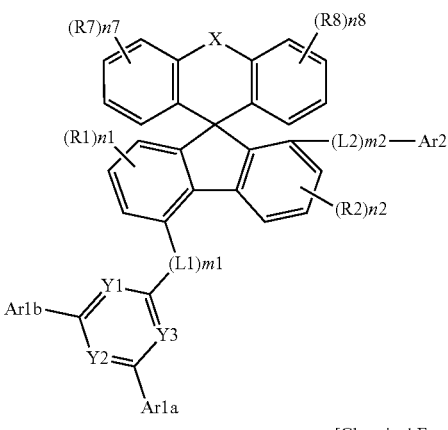
[Chemical Formula 1-5]
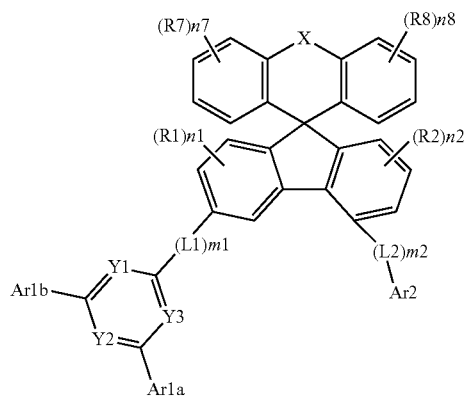
[Chemical Formula 1-6]
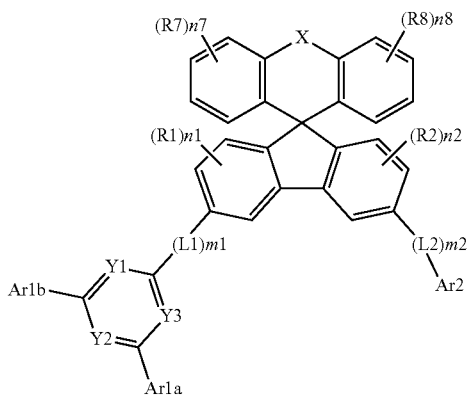
[Chemical Formula 1-7]
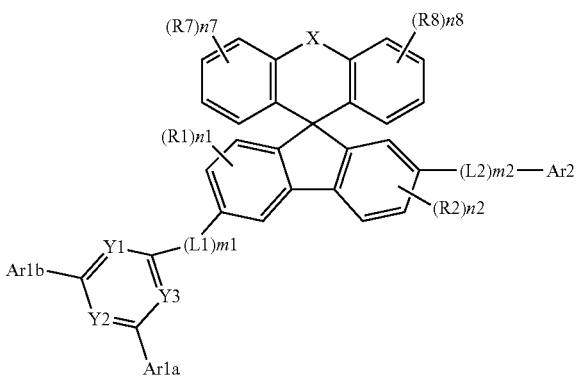

[Chemical Formula 1-8]
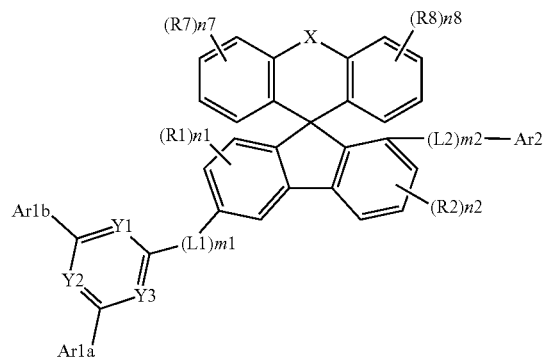
[Chemical Formula 1-9]
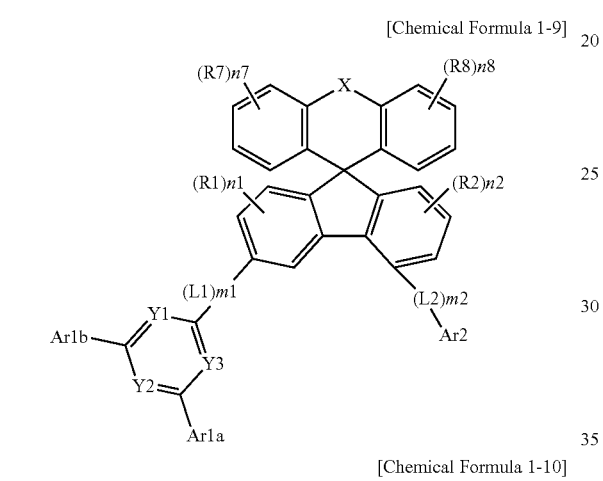
[Chemical Formula 1-10]
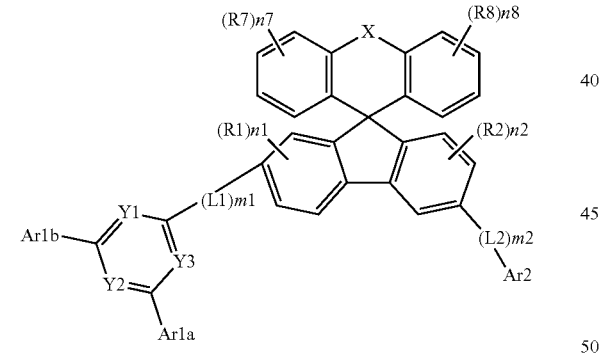
[Chemical Formula 1-11]
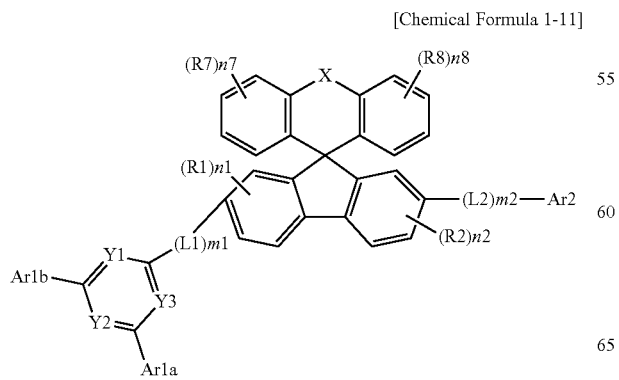
[Chemical Formula 1-12]
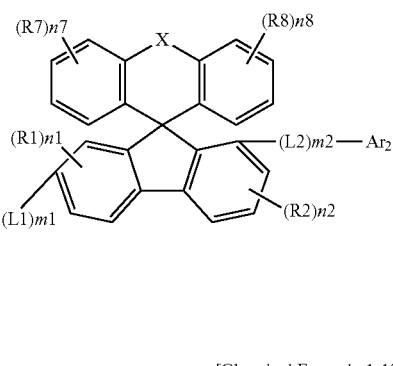
[Chemical Formula 1-13]
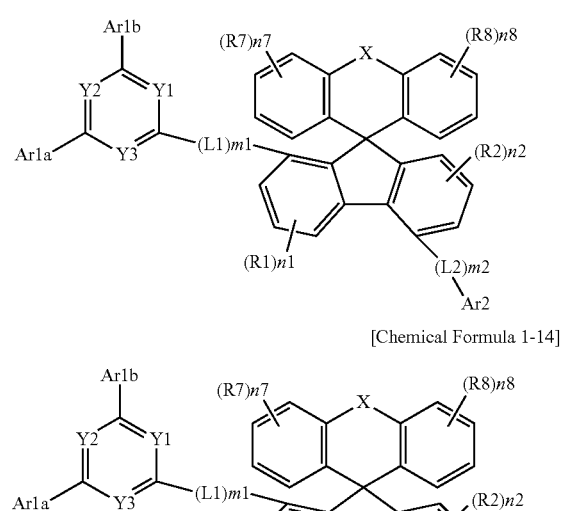
[Chemical Formula 1-14]
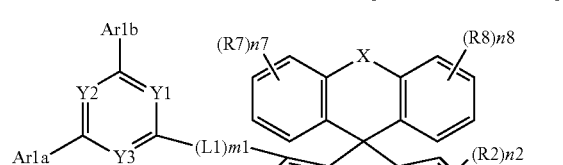
[Chemical Formula 1-15]
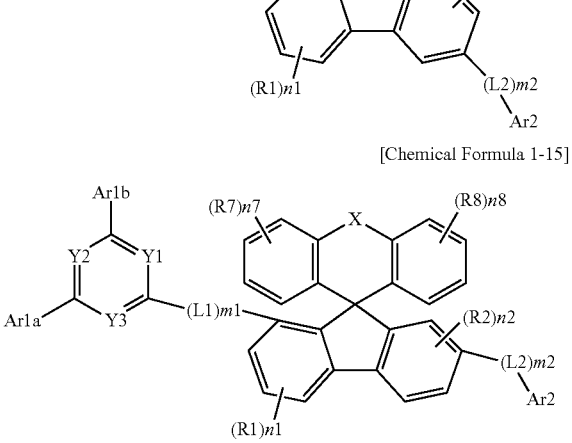
[Chemical Formula 1-16]
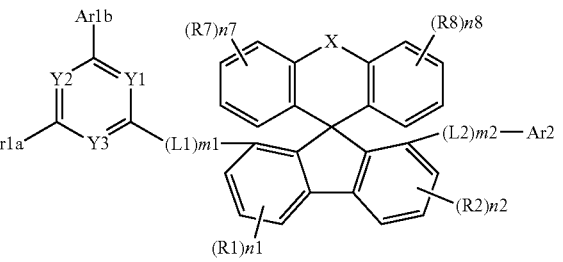

wherein in Chemical Formulae 1-1 to 1-16, the substituents have the same definitions as in Chemical Formula 1.

4. The heterocyclic compound of claim 1, wherein Chemical Formula 1 is one selected from among the following Chemical Formulae 1-17 to 1-32:

[Chemical Formula 1-17]

[Chemical Formula 1-18]

[Chemical Formula 1-19]

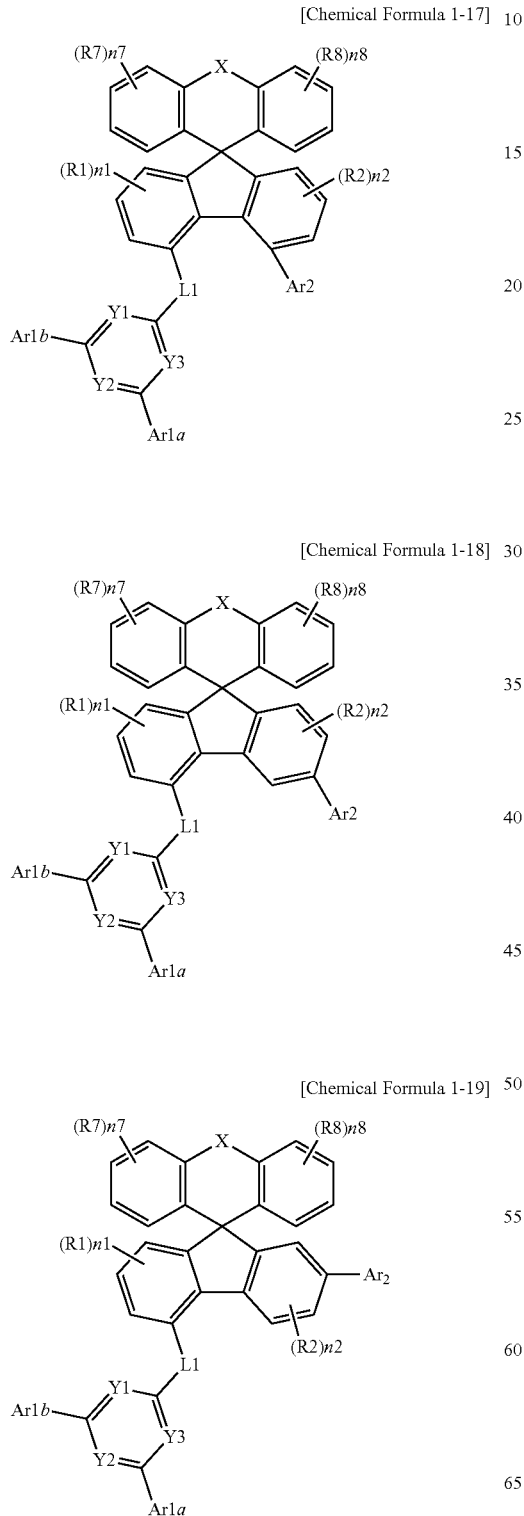

-continued

[Chemical Formula 1-20]

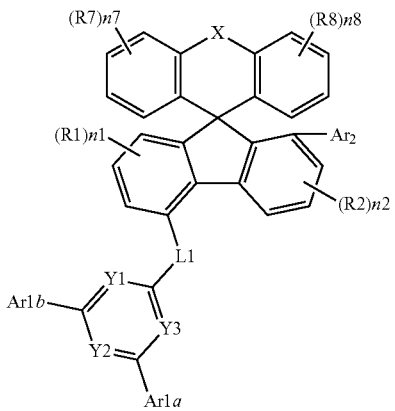

[Chemical Formula 1-21]

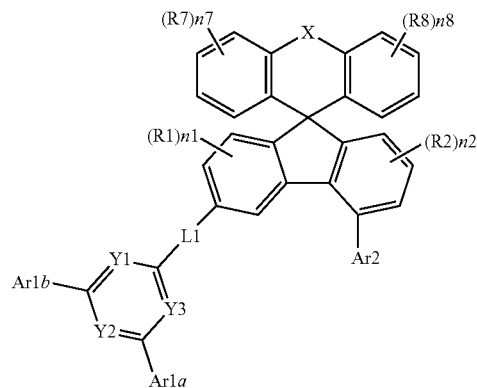

[Chemical Formula 1-22]

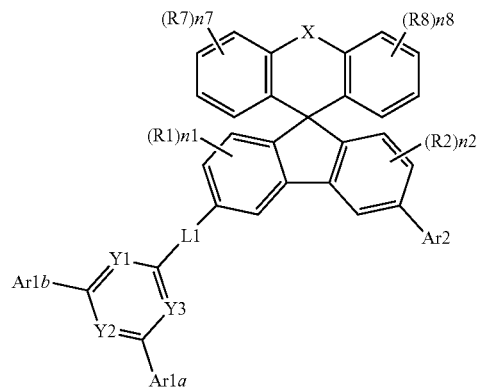

[Chemical Formula 1-23]

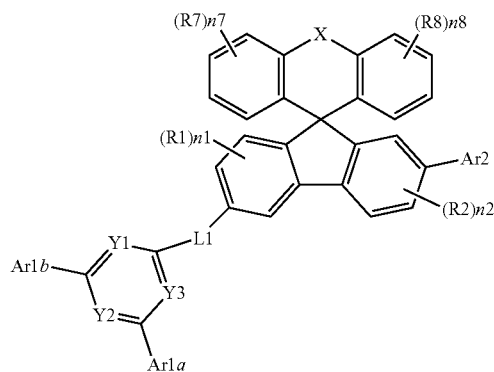

[Chemical Formula 1-24]
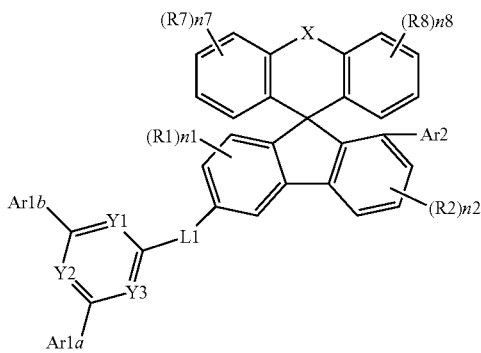
[Chemical Formula 1-25]
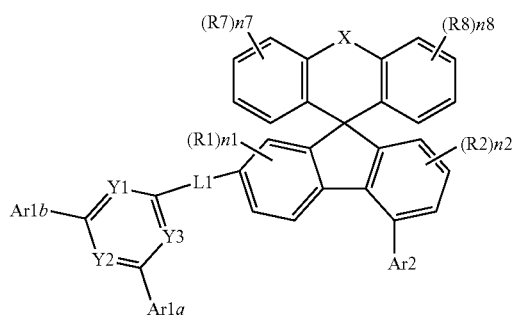
[Chemical Formula 1-26]
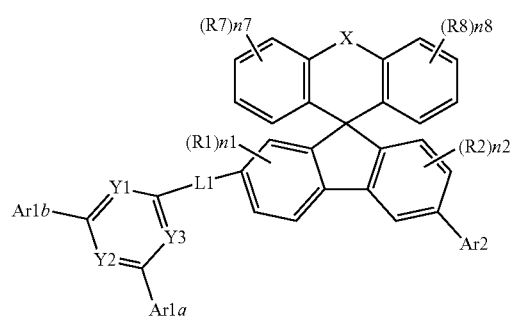
[Chemical Formula 1-27]
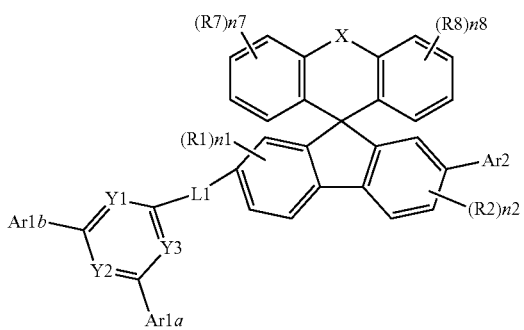
[Chemical Formula 1-28]
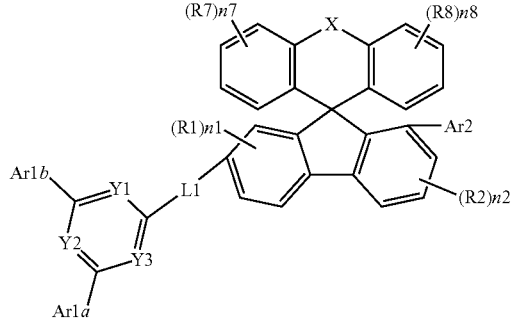
[Chemical Formula 1-29]
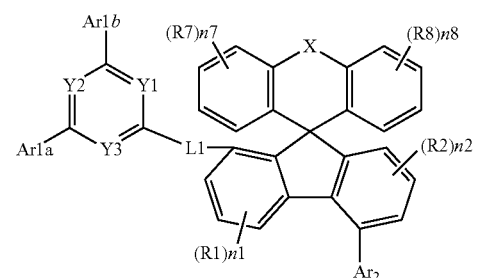
[Chemical Formula 1-30]
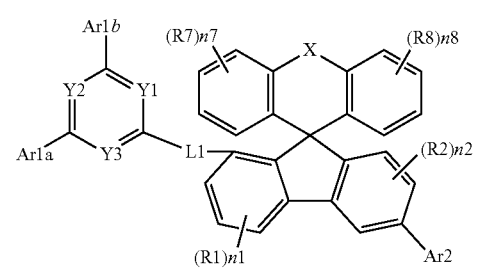
[Chemical Formula 1-31]
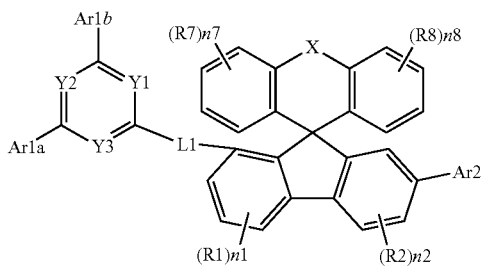
[Chemical Formula 1-32]
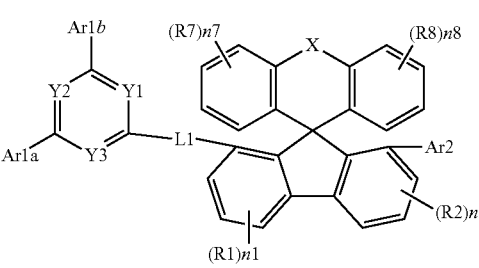
wherein in Chemical Formulae 1-17 to 1-32, the substituents have the same definitions as in Chemical Formula 1.
5. The heterocyclic compound of claim 1, wherein Y1 to Y3 are each N.

6. The heterocyclic compound of claim 1, wherein R1, R2, R7 and R8 are each hydrogen.
7. The heterocyclic compound of claim 1, wherein Chemical Formula 1 is one selected from among the following compounds:
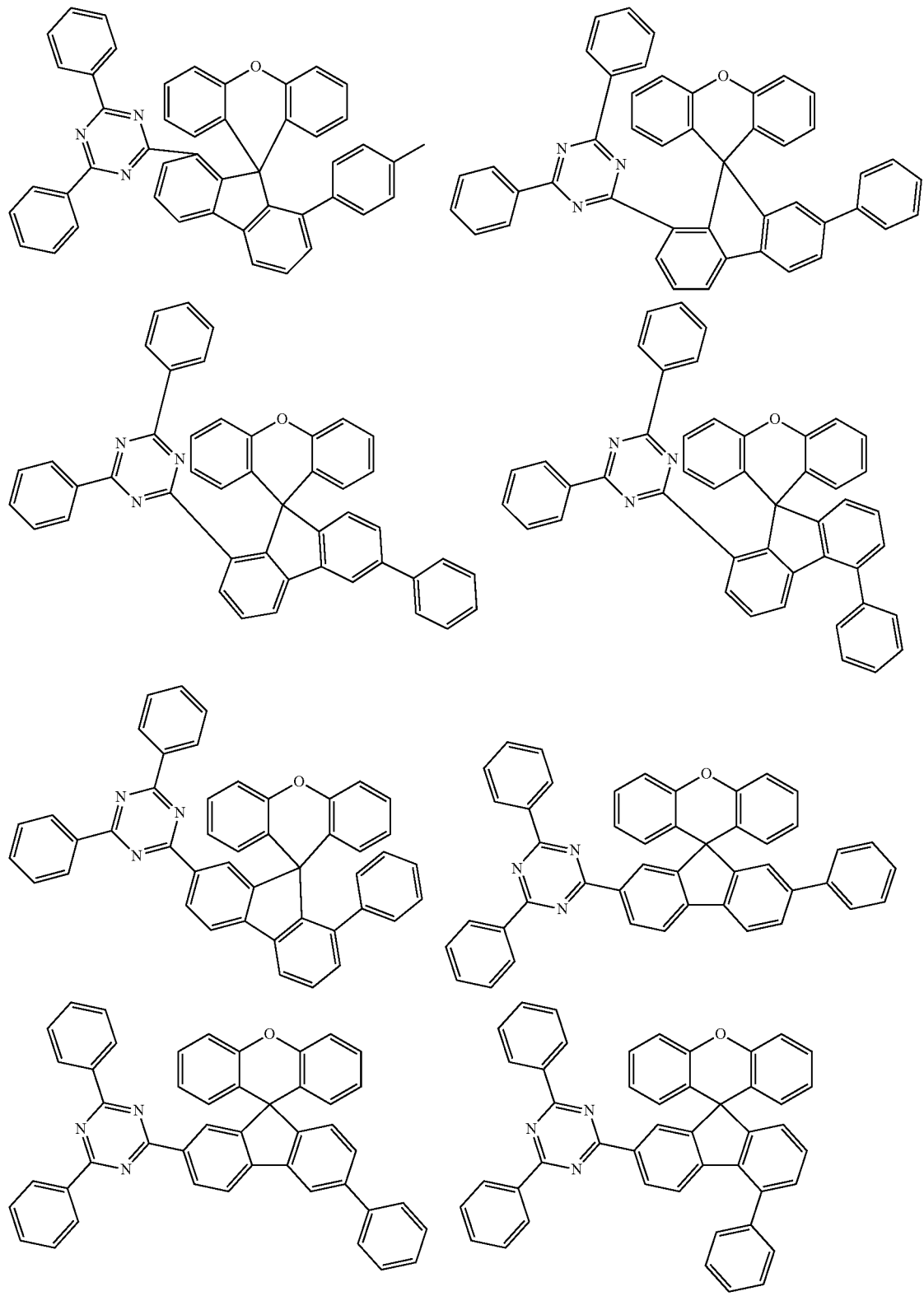

-continued
107
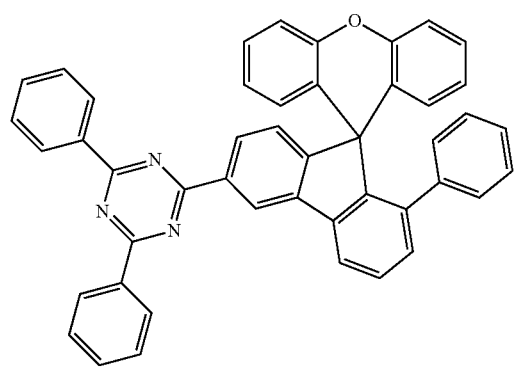
108
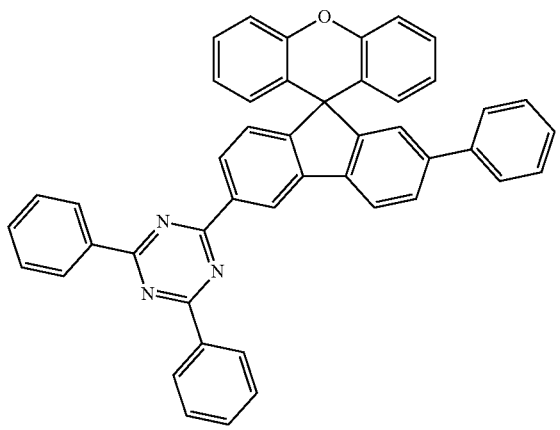
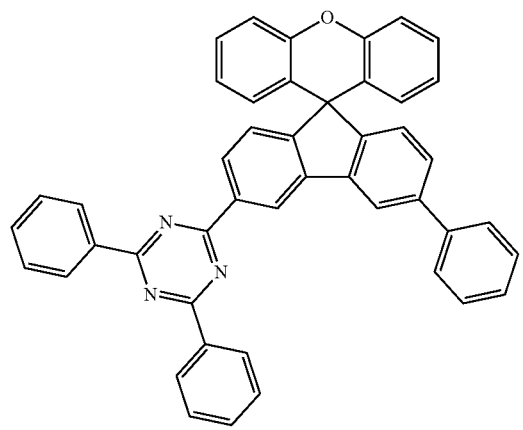
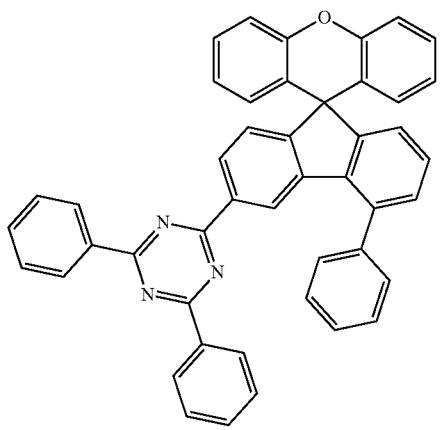
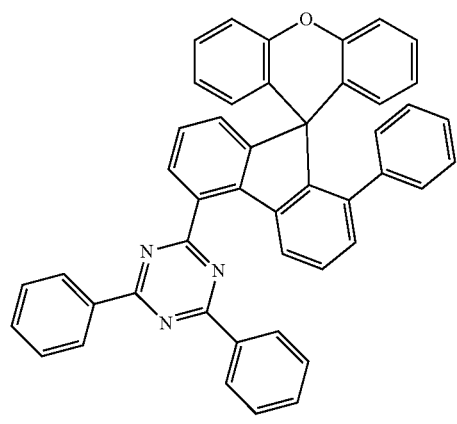
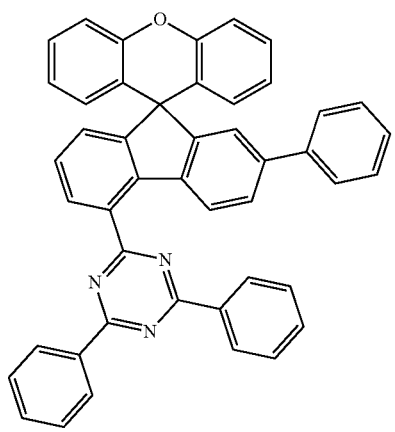
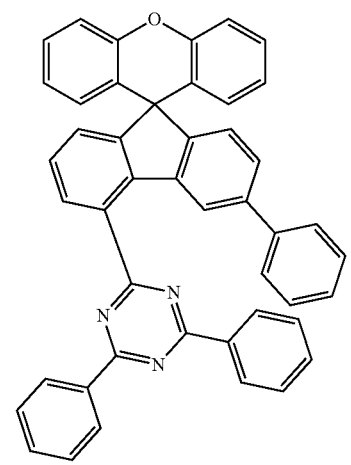

-continued
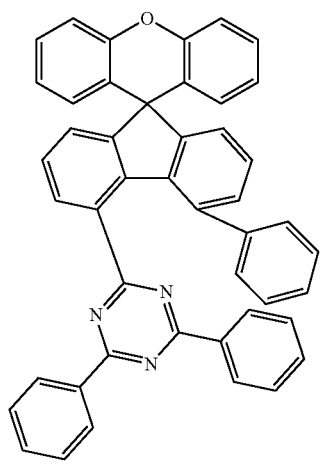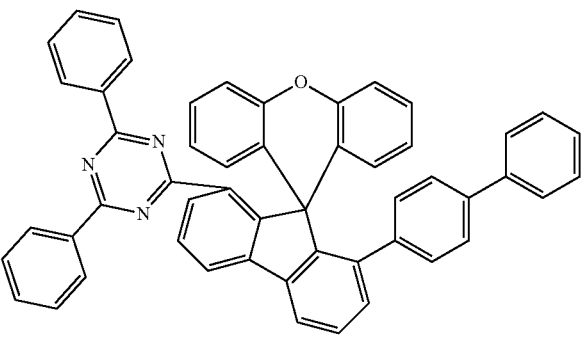
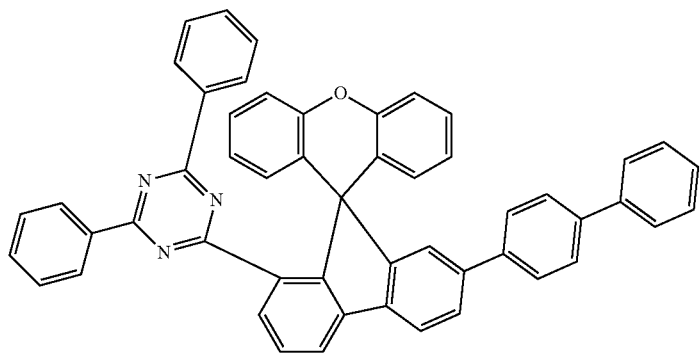
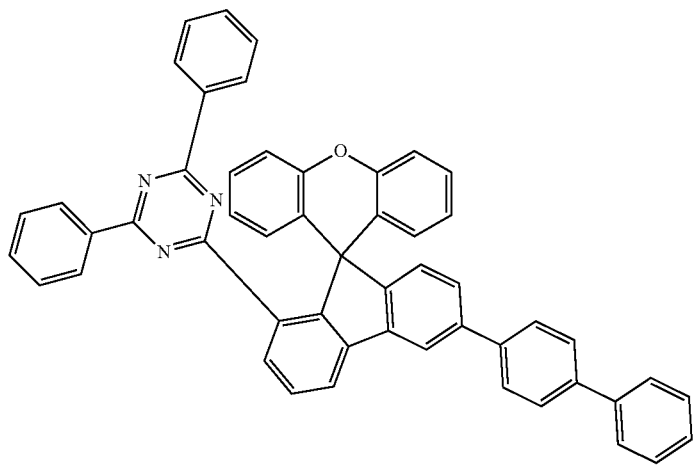

111 112
-continued
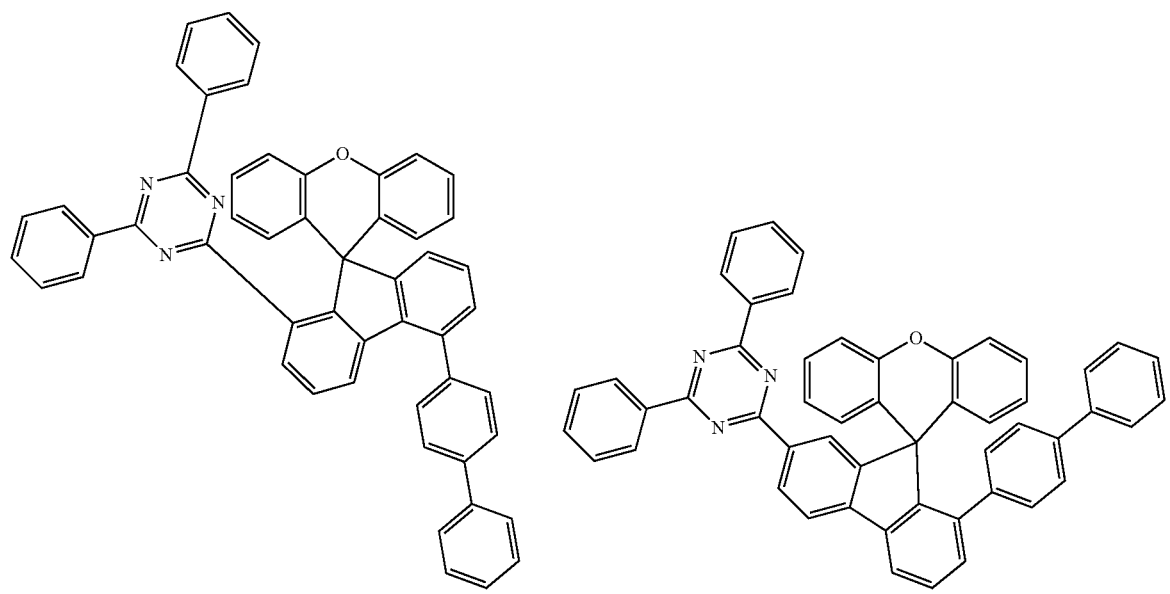
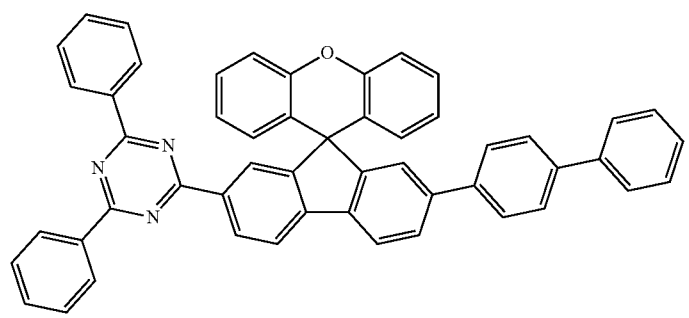
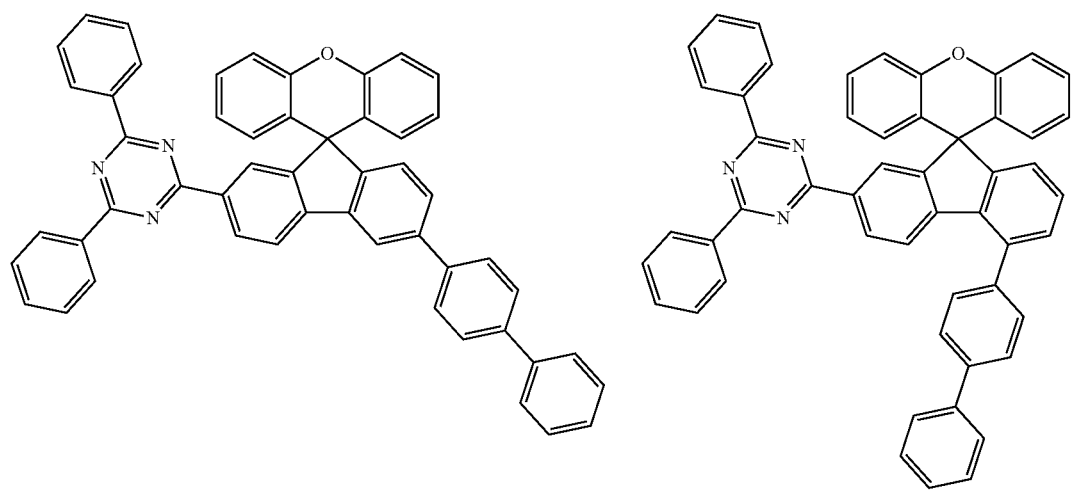

-continued
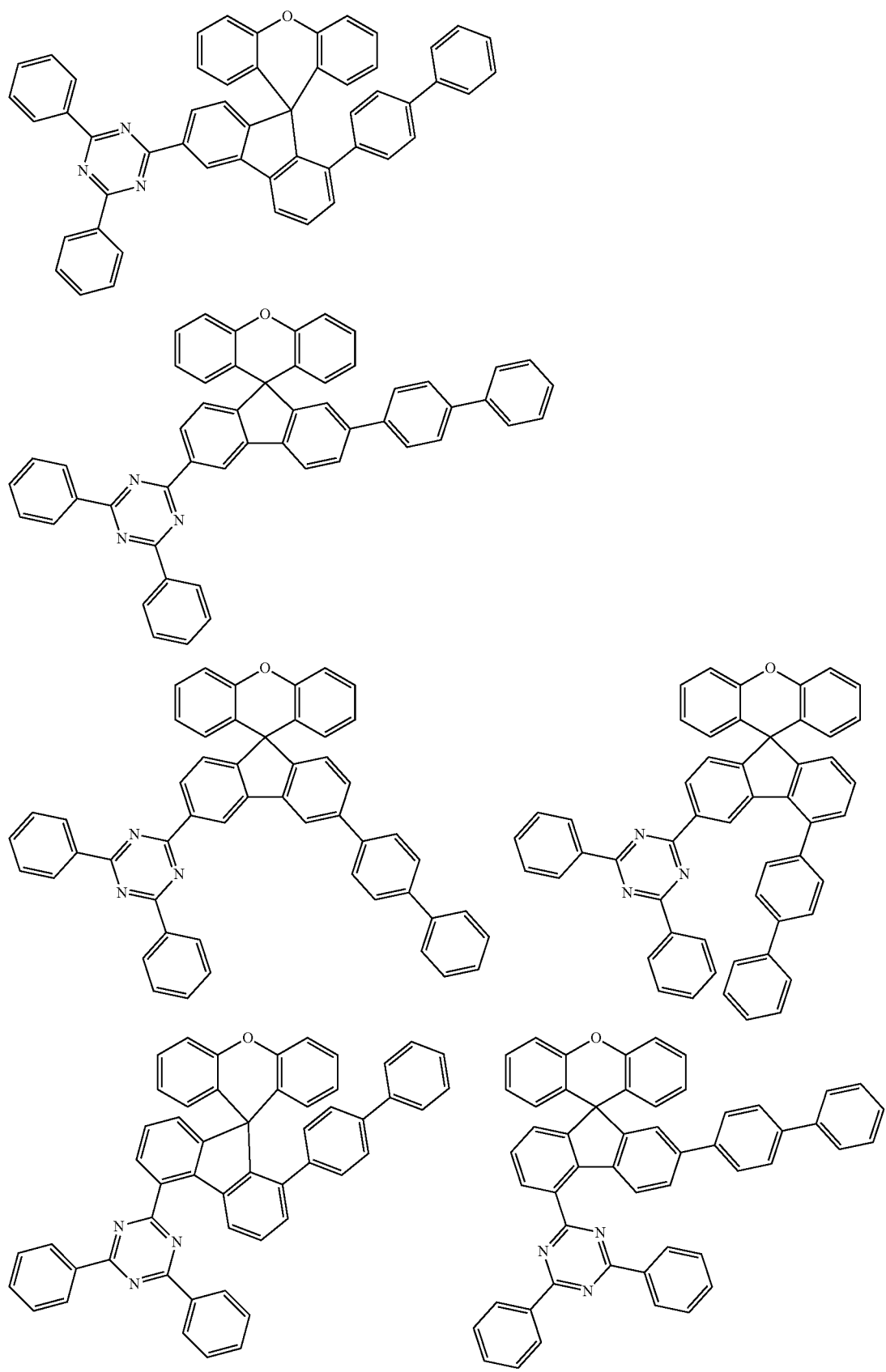

-continued
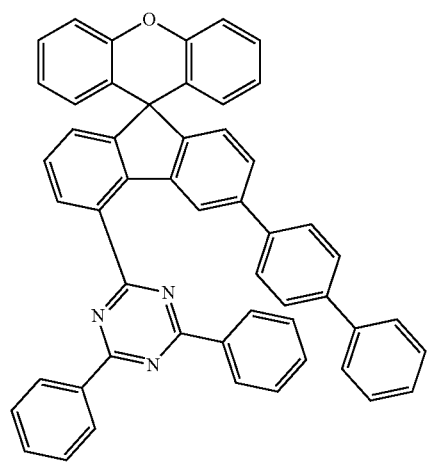 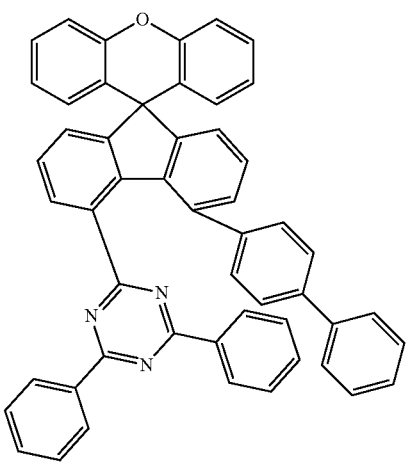
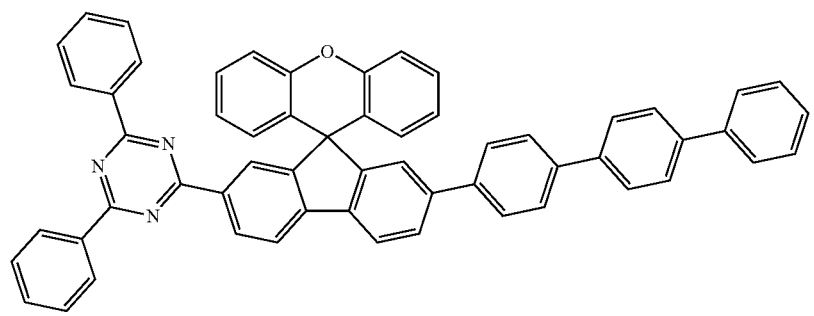
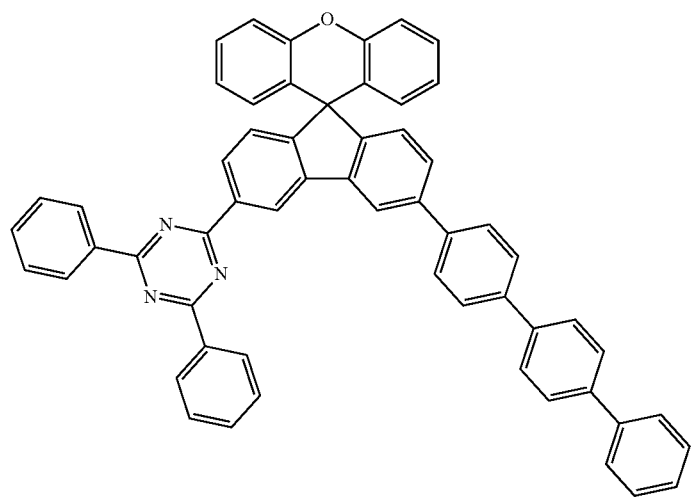

-continued
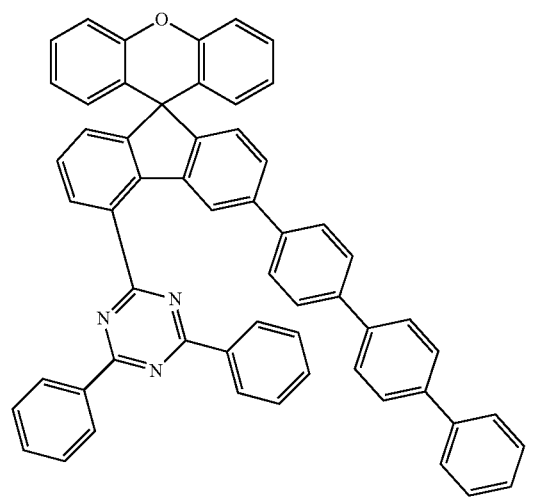
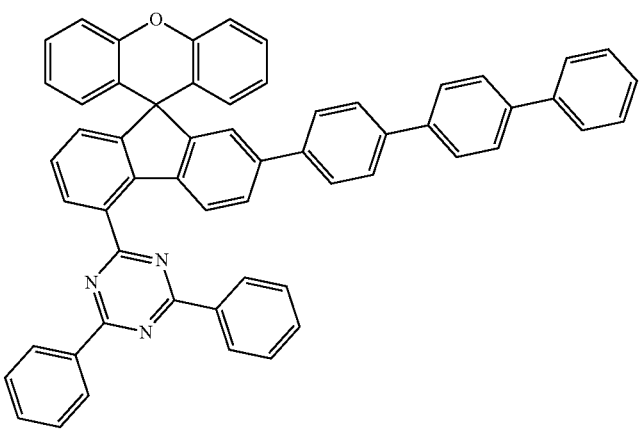
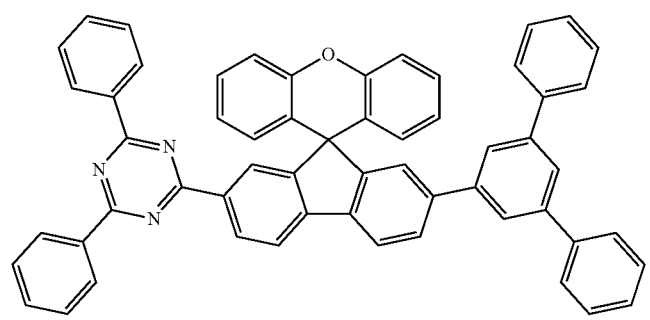
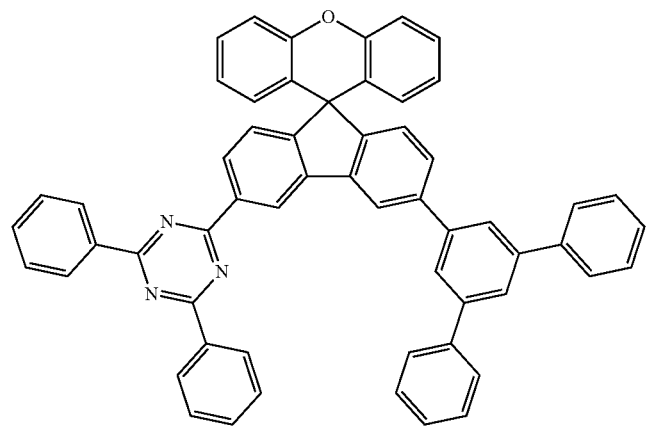
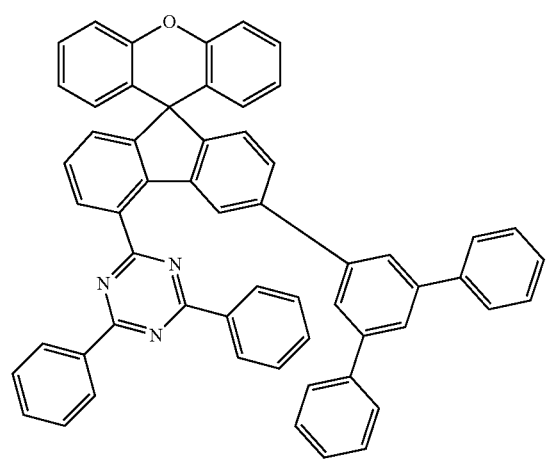
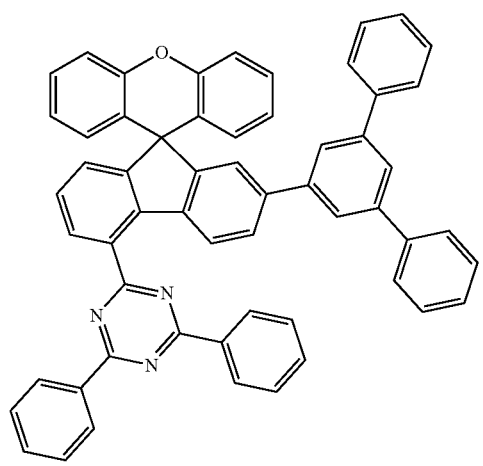

-continued
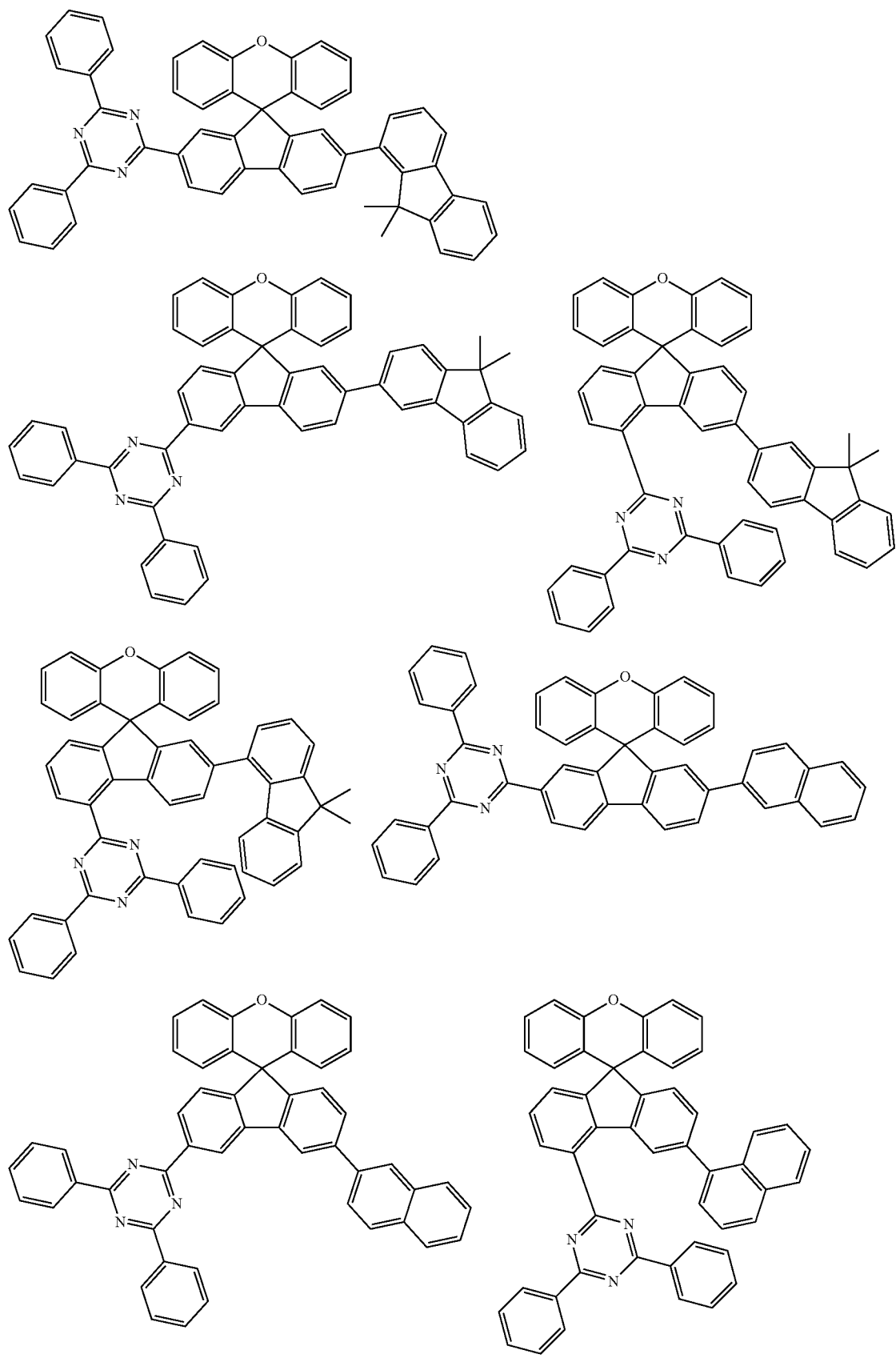

-continued
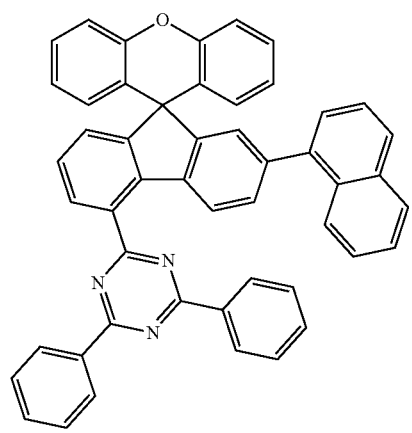
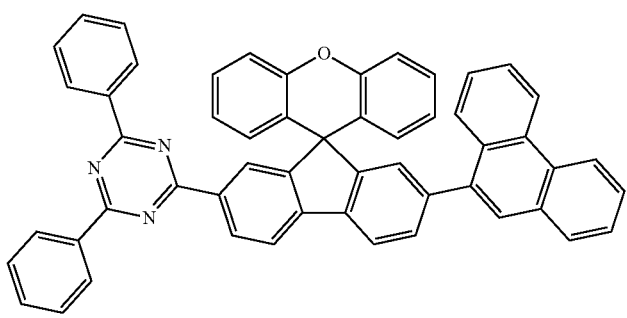
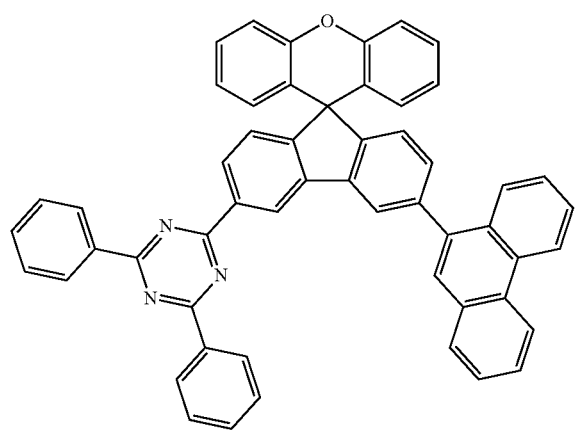
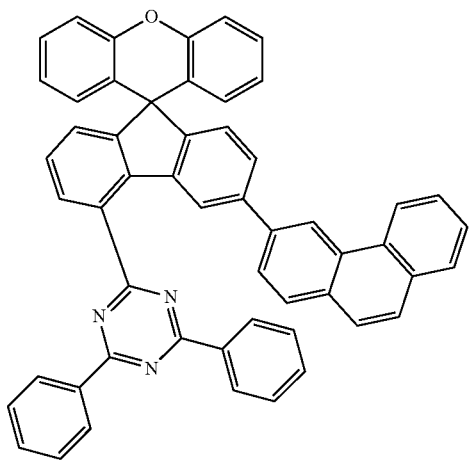
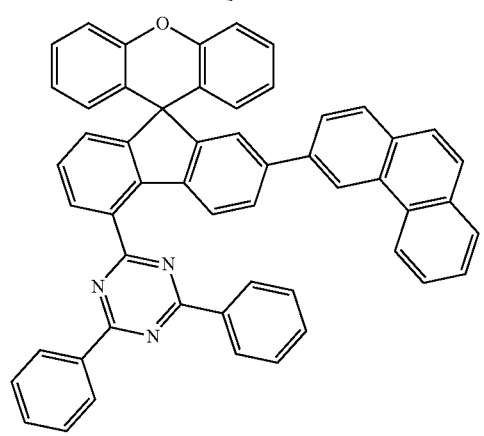
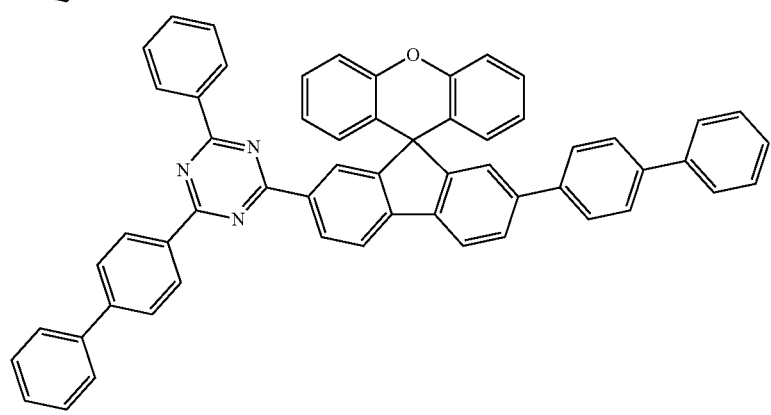

-continued
123 124
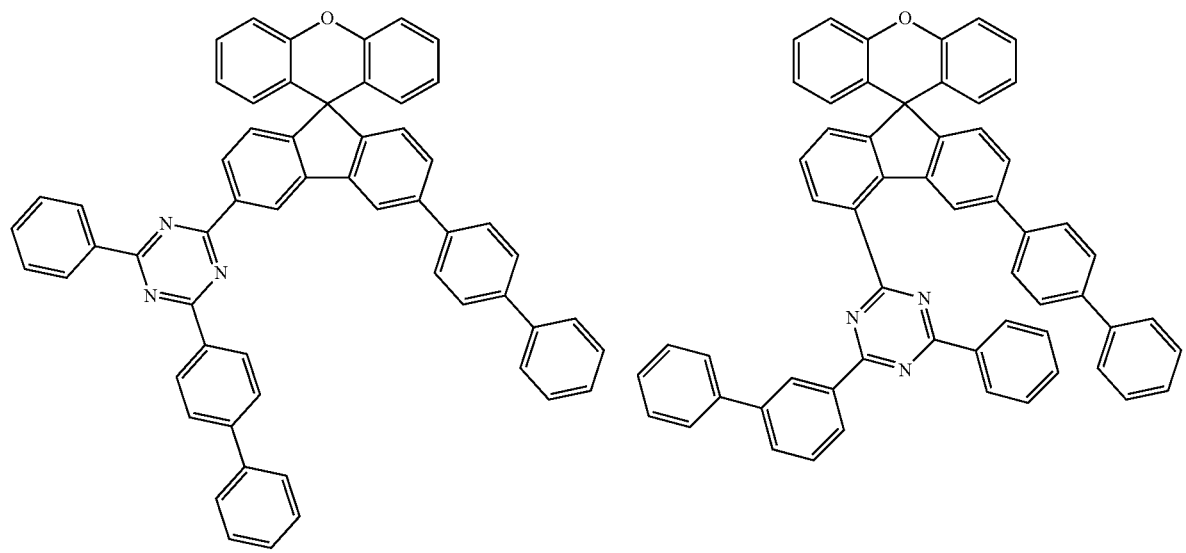
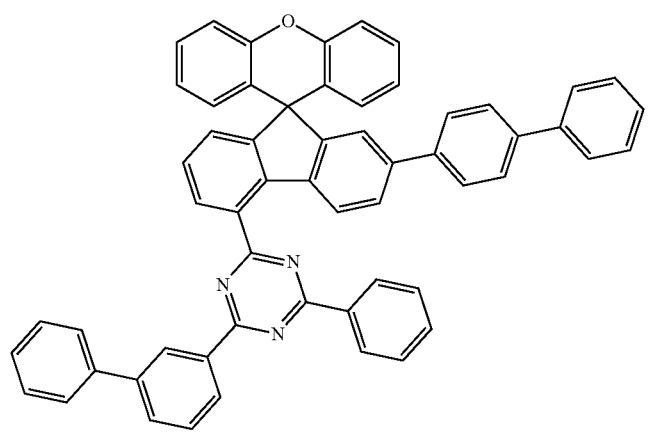
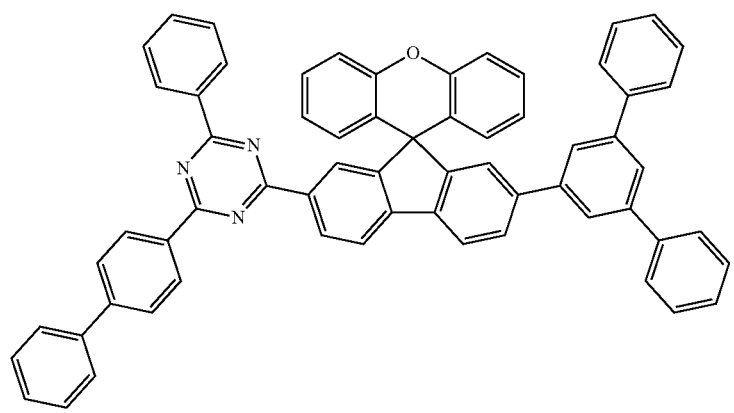

-continued
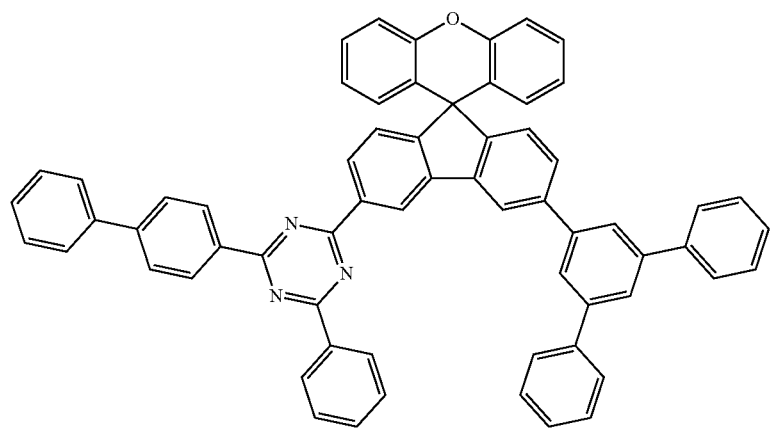
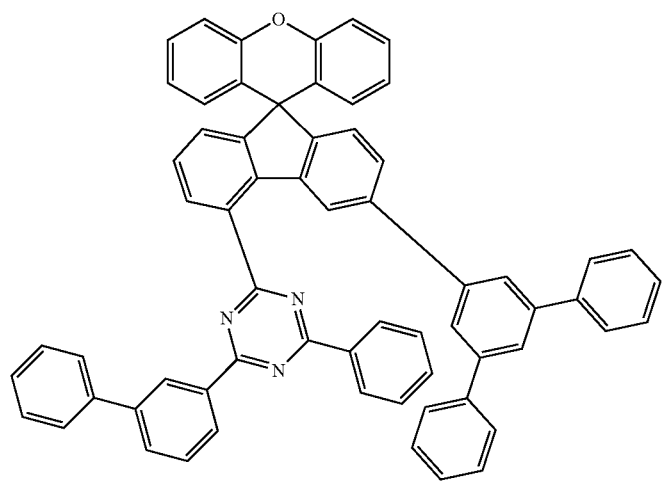
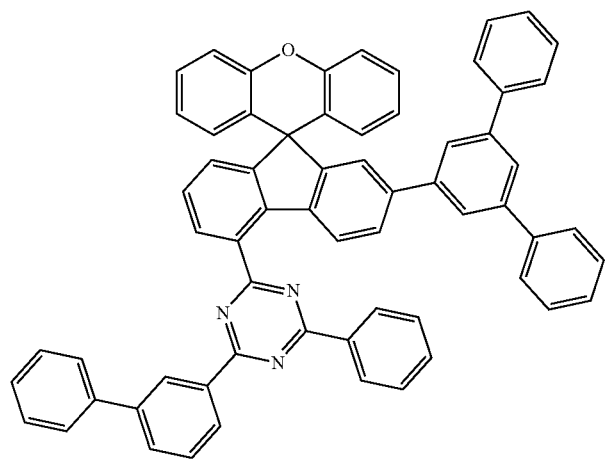

-continued
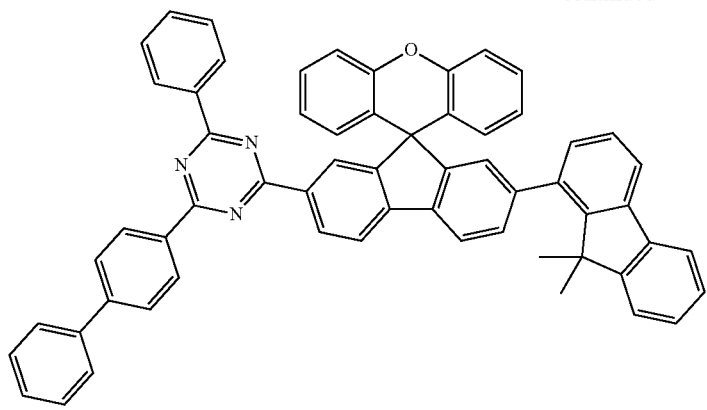
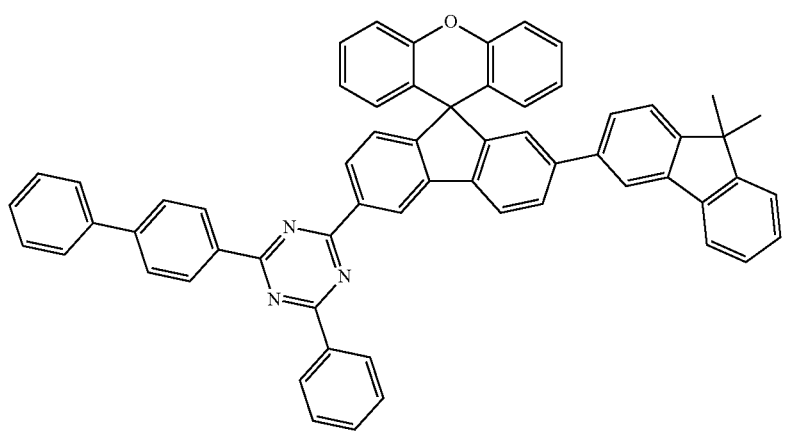
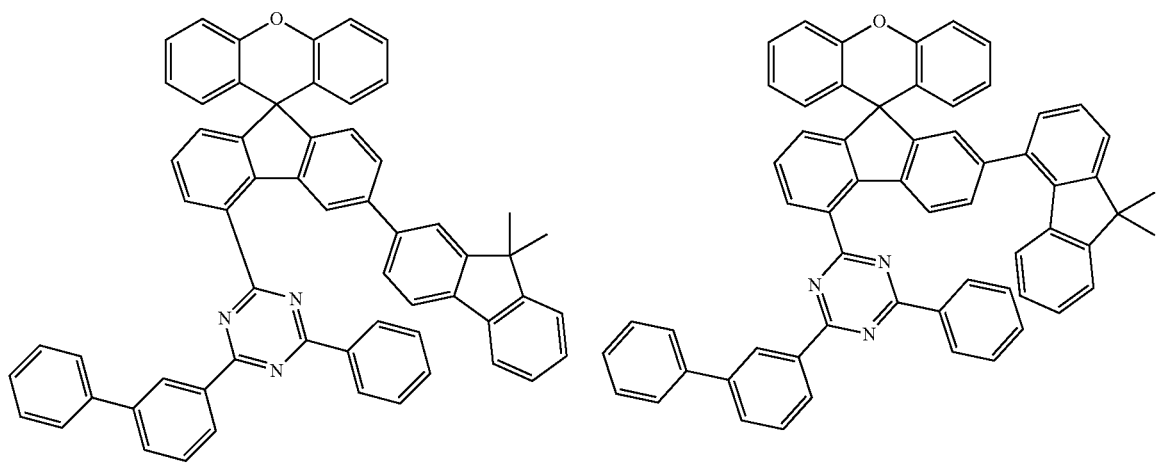
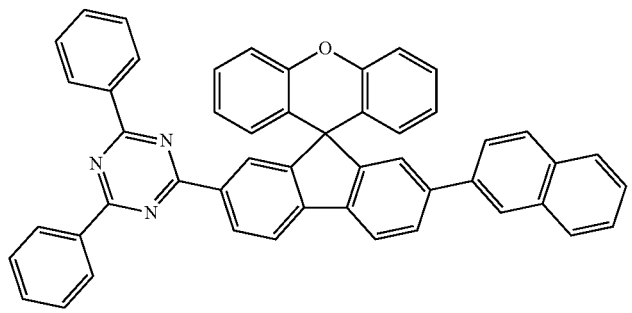

129
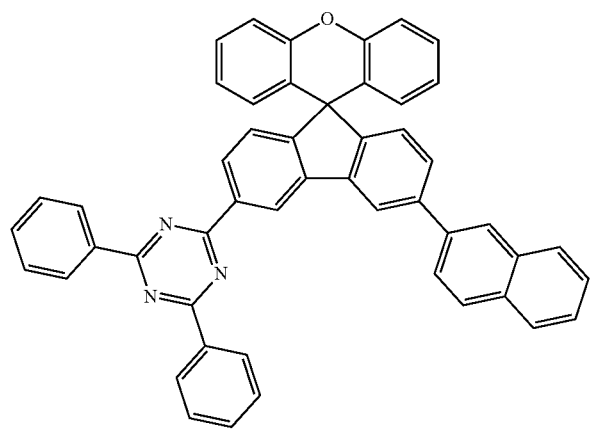
130
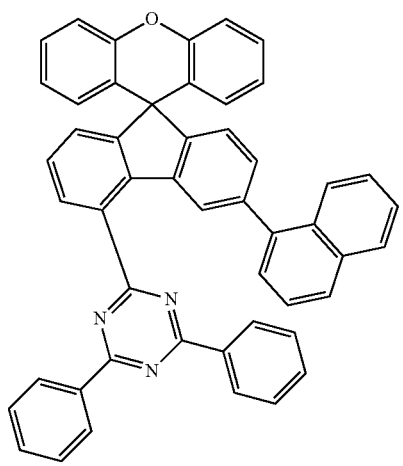
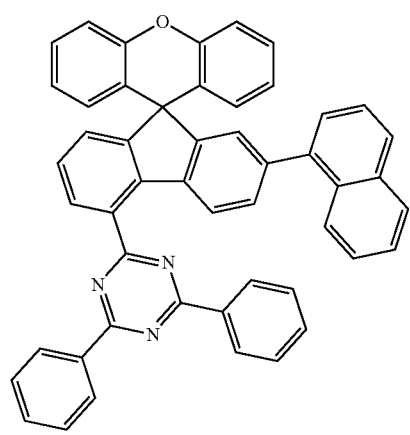
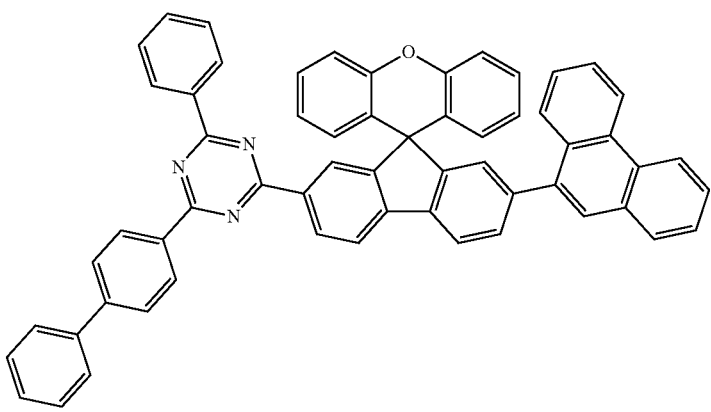
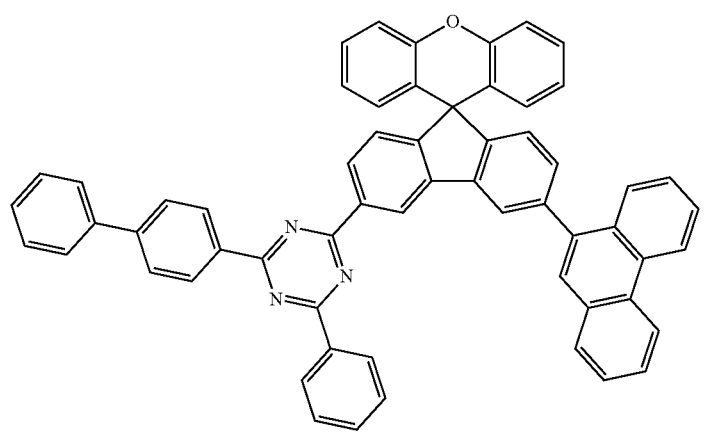

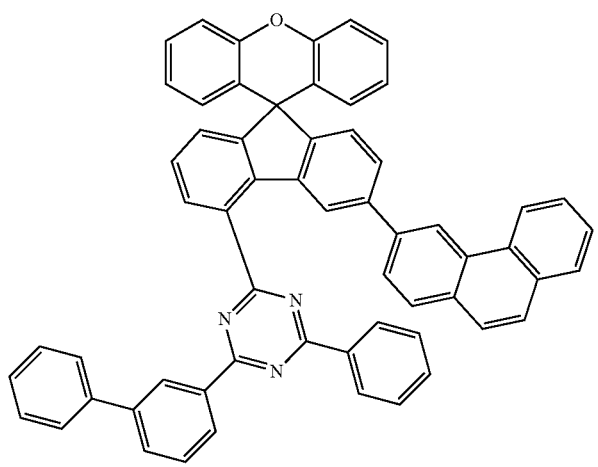

133
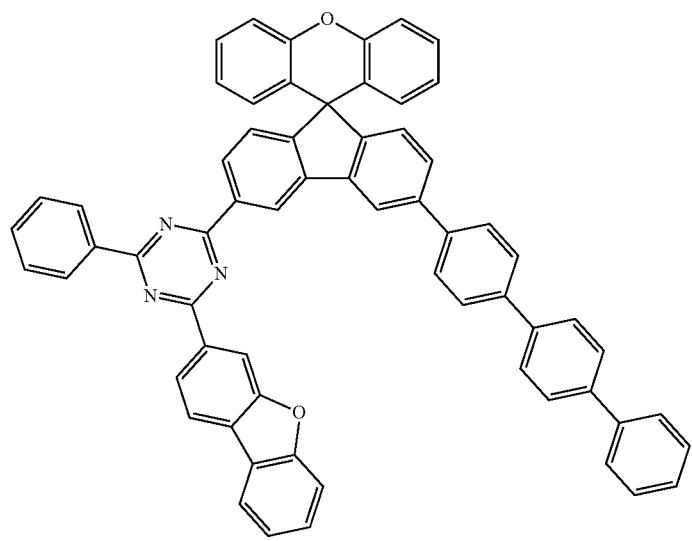
134
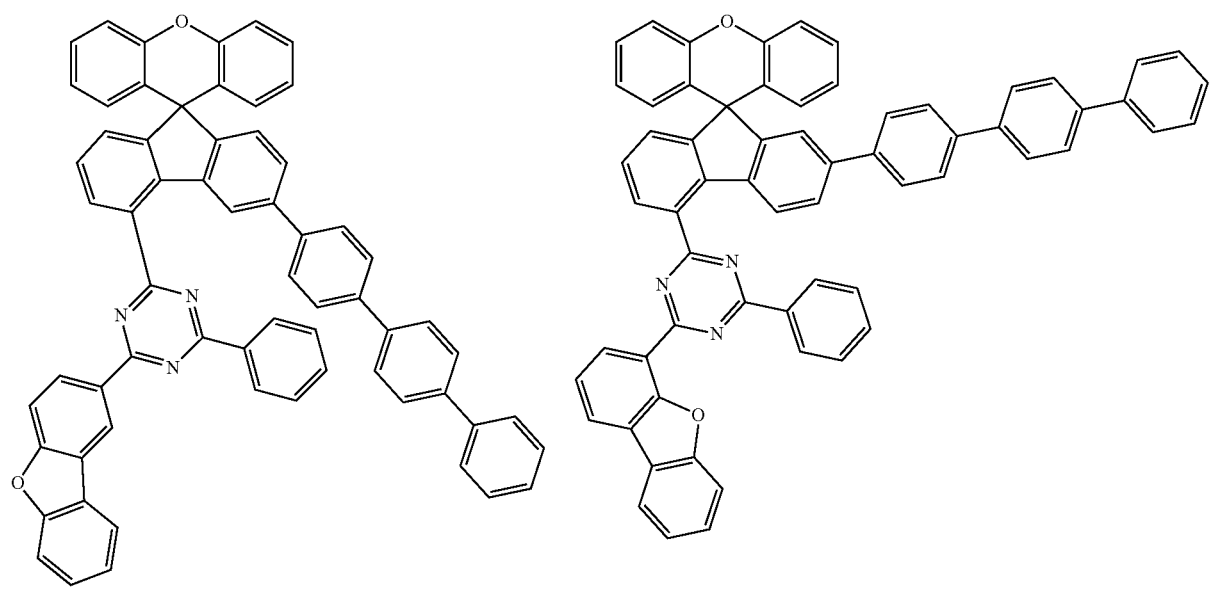
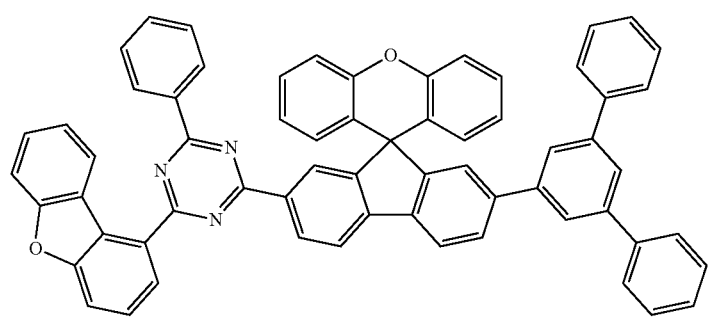

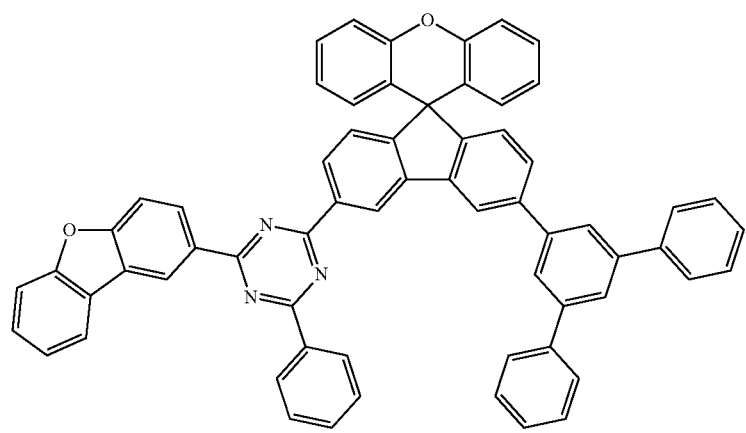
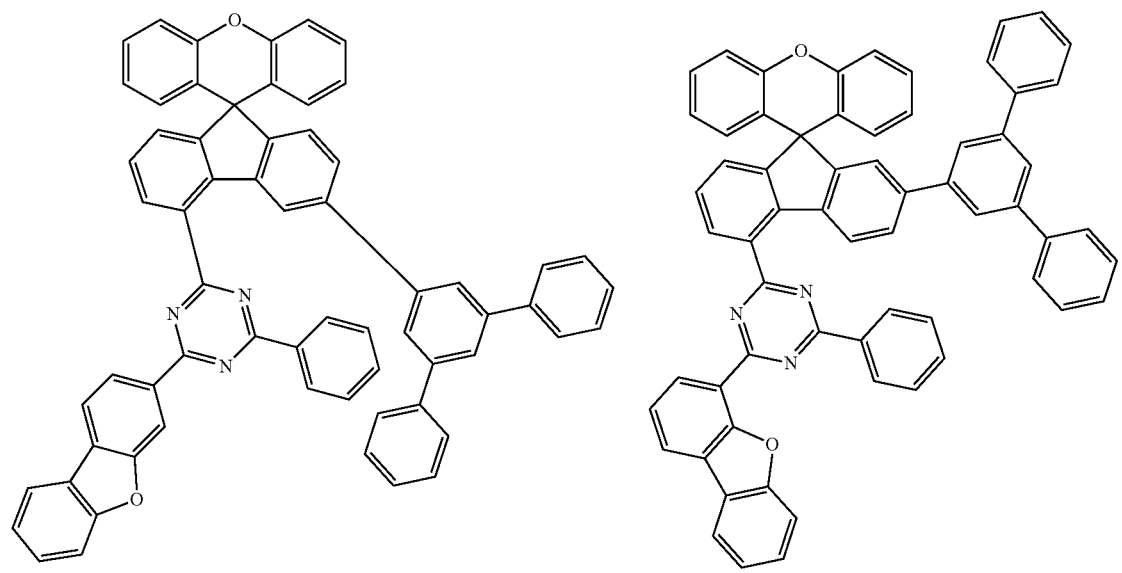
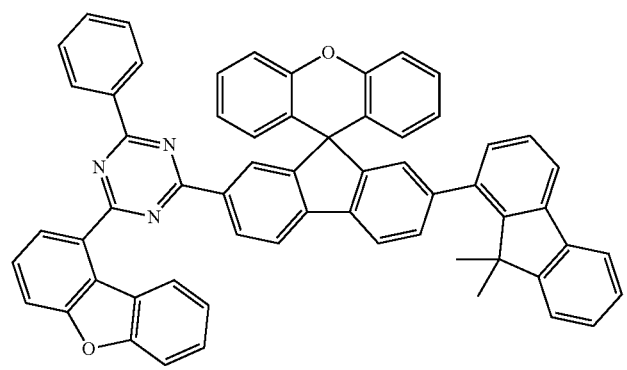

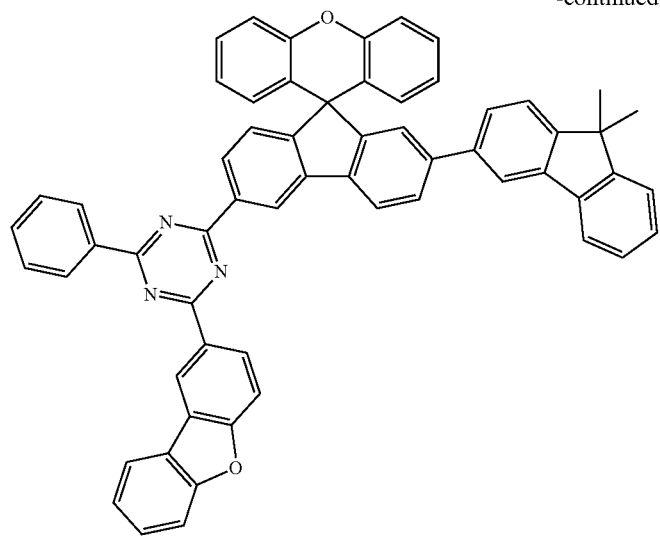
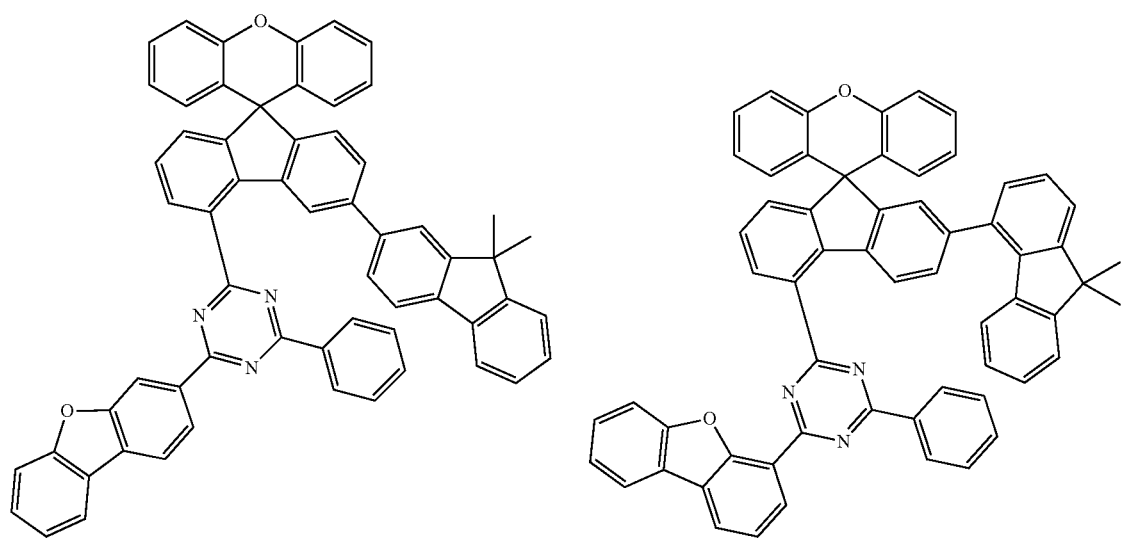
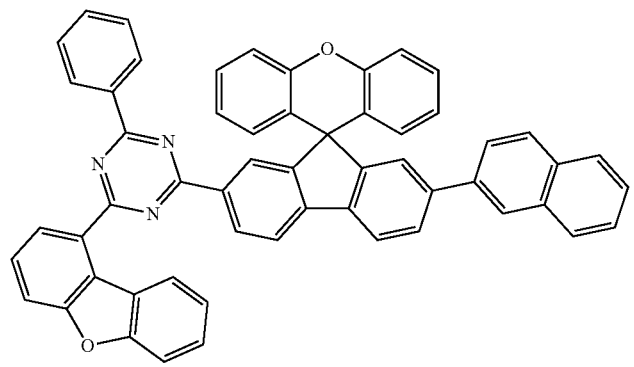

139
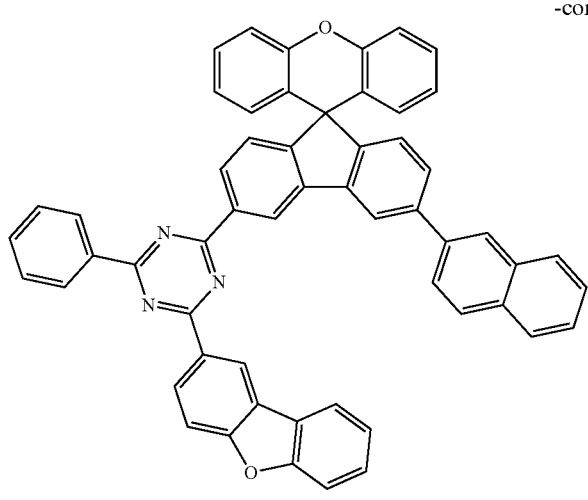
140
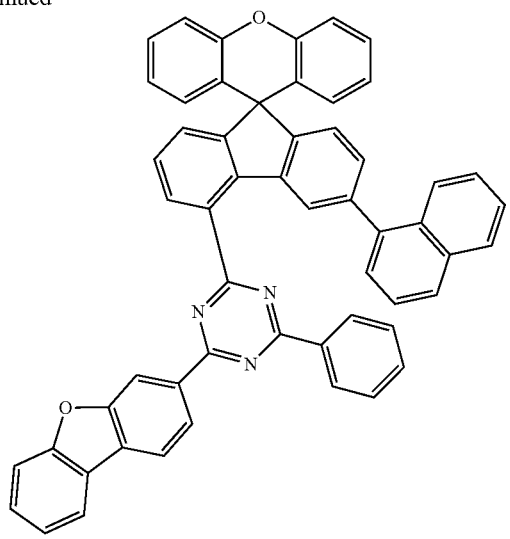
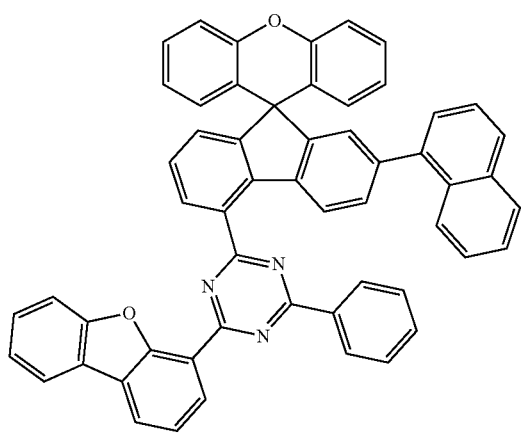
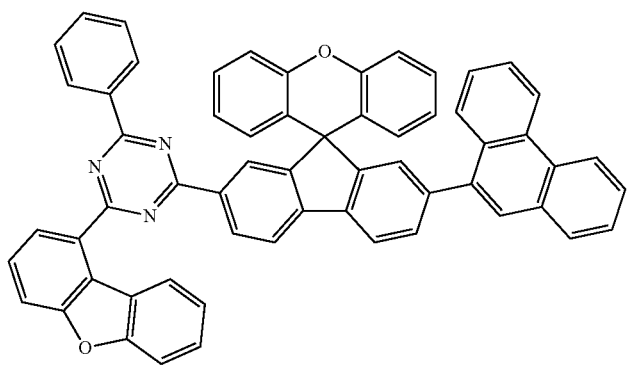
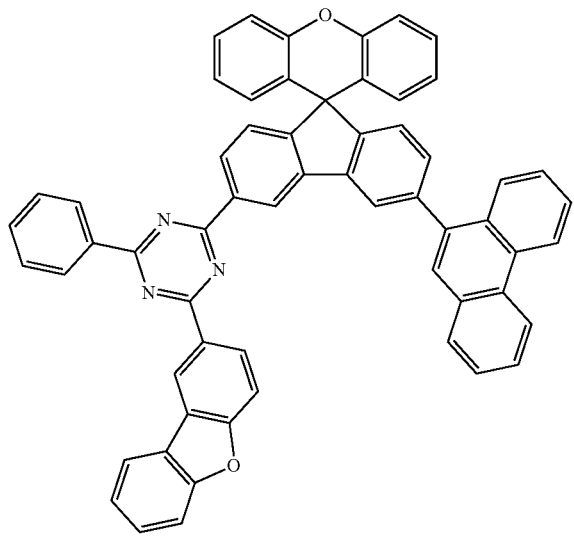
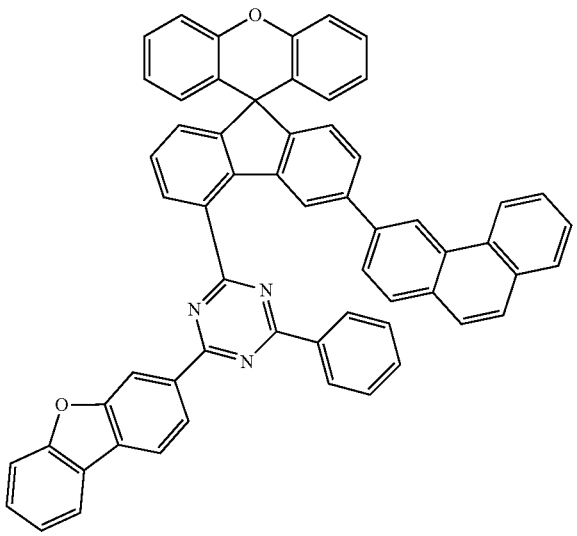

-continued
141
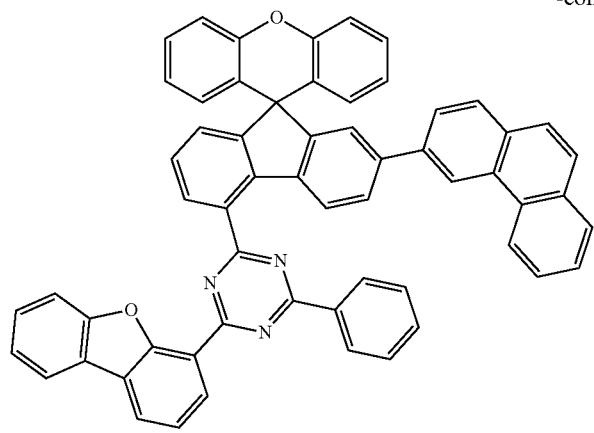
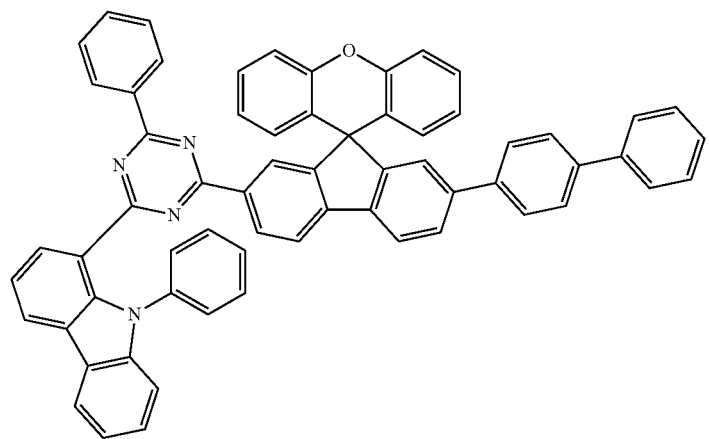
142
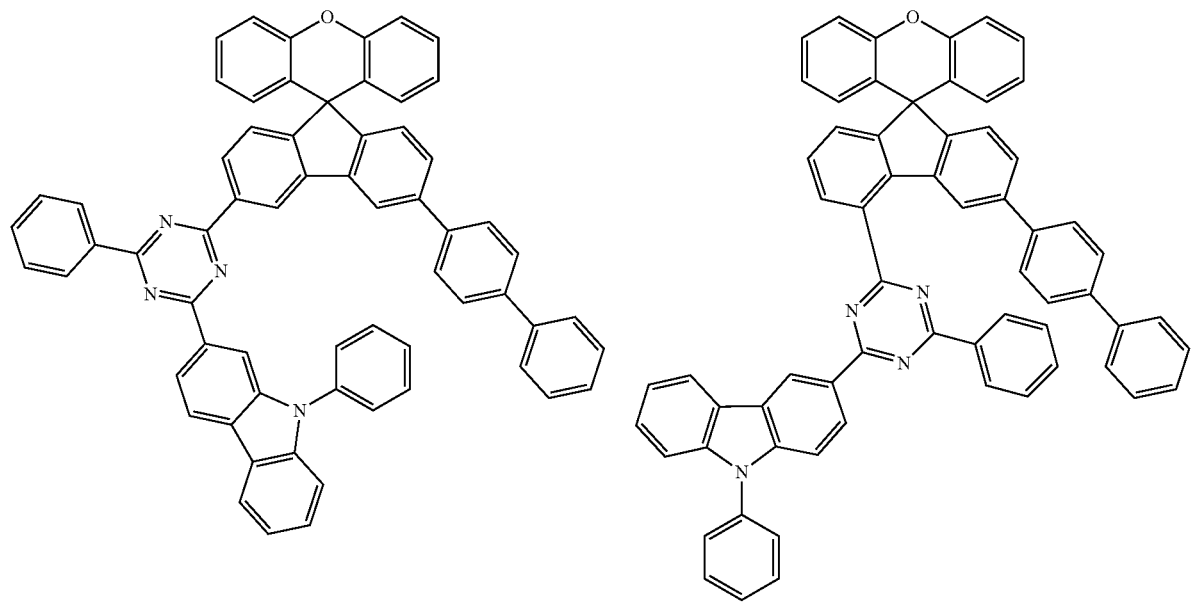

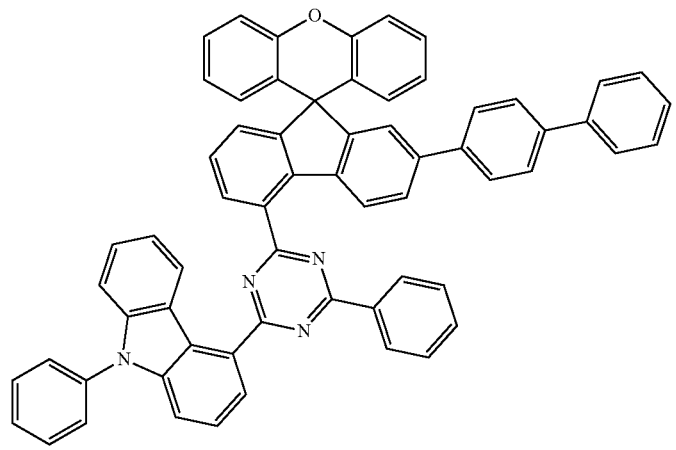
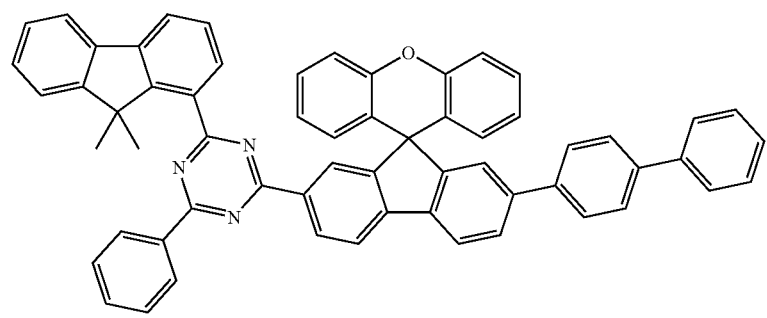
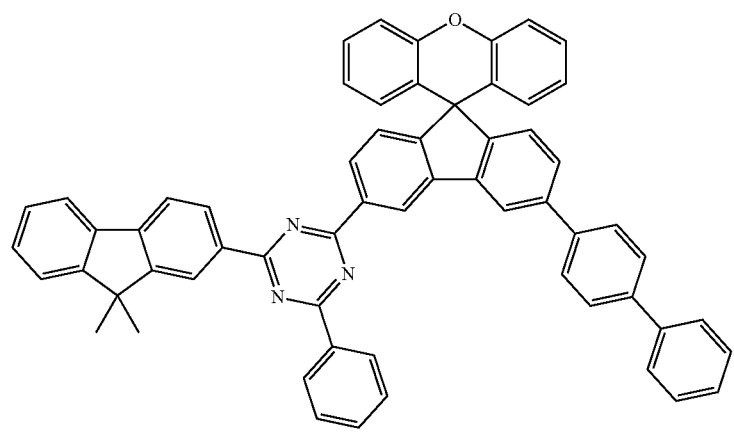

145
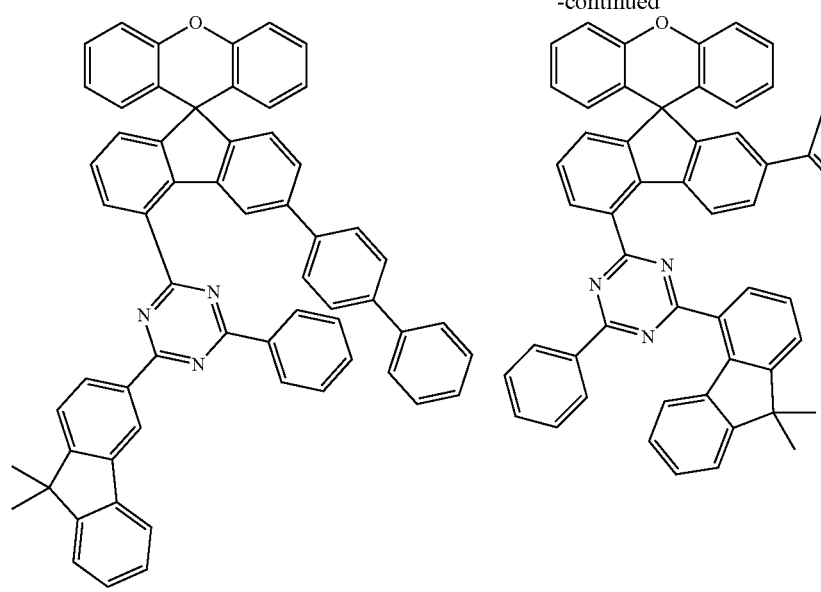
146
-continued
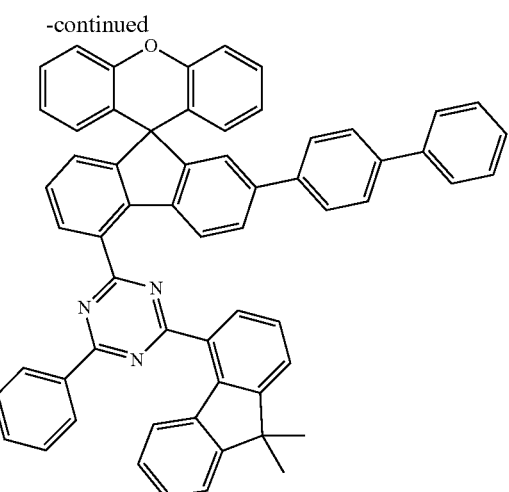
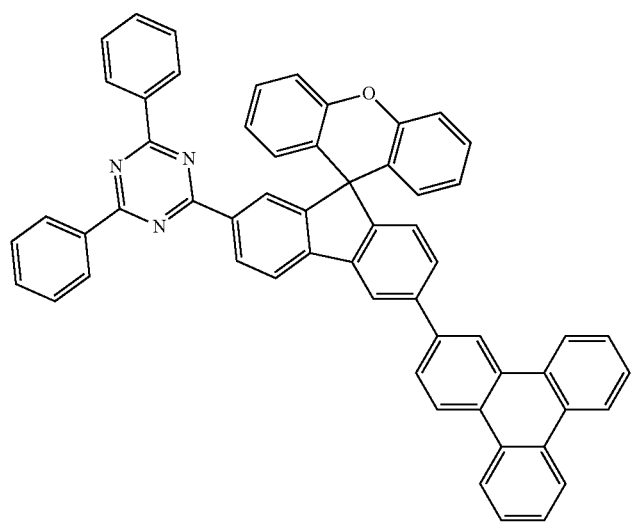
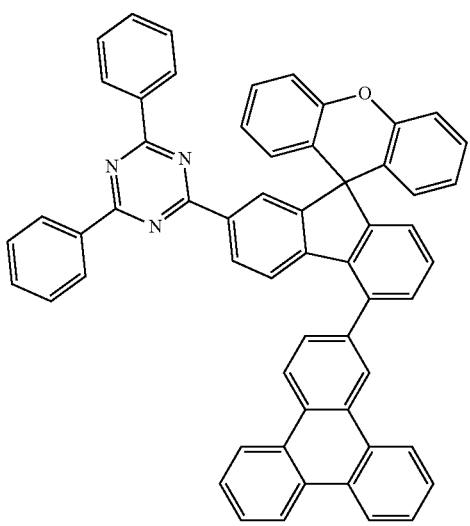
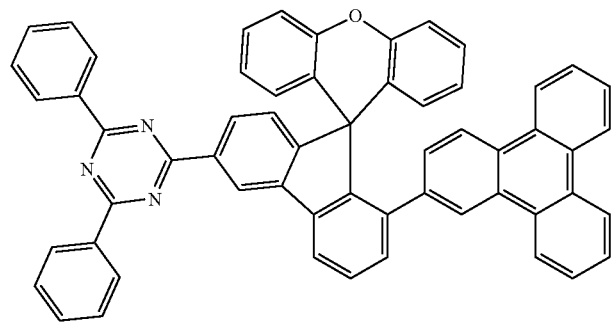

-continued
147
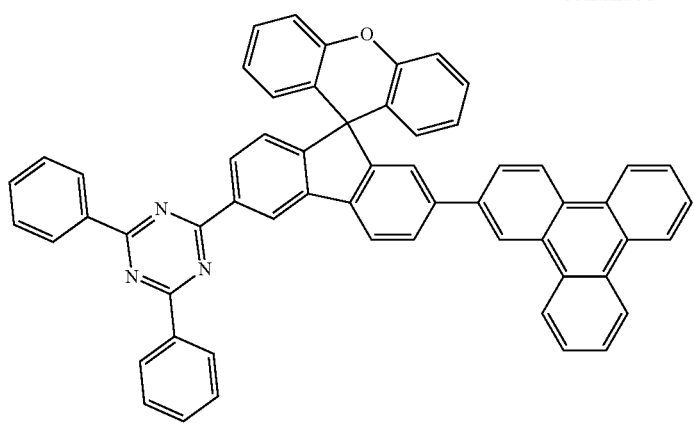
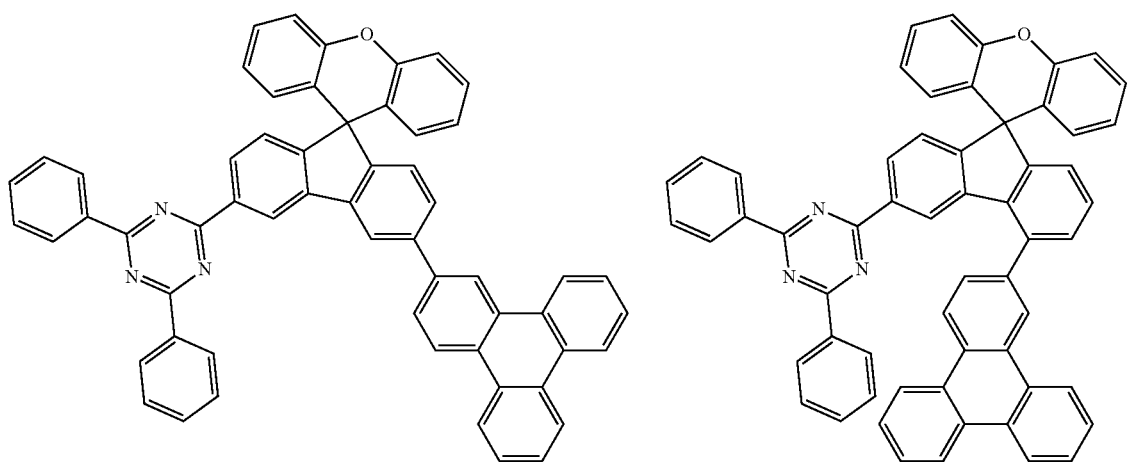
148
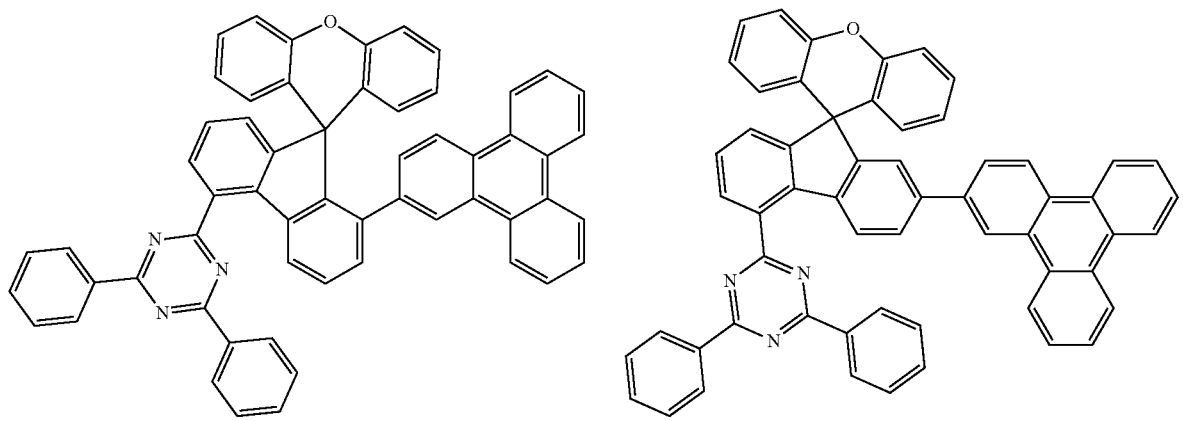

-continued

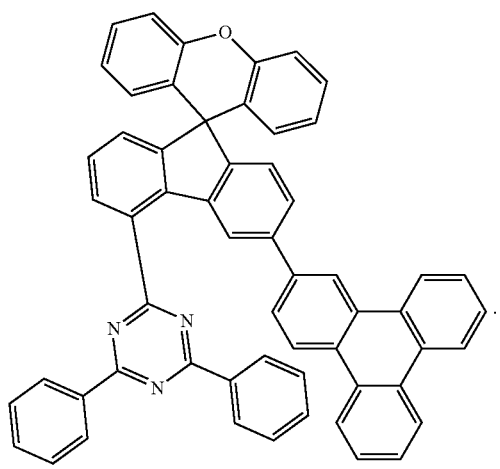

8. An organic light emitting device comprising:
a first electrode;
a second electrode provided opposite to the first electrode; and
one or more organic material layers provided between the first electrode and the second electrode,
wherein one or more layers of the organic material layers include the heterocyclic compound of claim 1.

9. The organic light emitting device of claim 8, wherein the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound.

10. The organic light emitting device of claim 8, wherein the organic material layer includes a hole blocking layer, and the hole blocking layer includes the heterocyclic compound.

11. The organic light emitting device of claim 8, wherein the organic material layer includes an electron control layer, and the electron control layer includes the heterocyclic compound.

12. The heterocyclic compound of claim 1, wherein Ar2 is an aryl group that is selected from among a phenyl group that is unsubstituted or substituted with an alkyl group, a biphenyl group that is unsubstituted or substituted with an alkyl group, a terphenyl group that is unsubstituted or substituted with an alkyl group, a quaterphenyl group that is unsubstituted or substituted with an alkyl group, a fluorenyl group that is unsubstituted or substituted with an alkyl group, a naphthyl group that is unsubstituted or substituted with a deuterium, a triphenylene group that is unsubstituted or substituted with a deuterium, a phenanthrene group that is unsubstituted or substituted with a deuterium, a chrysene group that is unsubstituted or substituted with a deuterium, a fluoranthene group that is unsubstituted or substituted with a deuterium, a pyrene group that is unsubstituted or substituted with a deuterium, a perylene group that is unsubstituted or substituted with a deuterium, a benzophenanthrene group that is unsubstituted or substituted with a deuterium, a benzotetraphene group that is unsubstituted or substituted with a deuterium, or a tetraphene group that is unsubstituted or substituted with a deuterium.

13. The heterocyclic compound of claim 1, wherein Ar2 is an aryl group that is selected from among a phenyl group that is unsubstituted or substituted with an alkyl group, a biphenyl group that is unsubstituted or substituted with a deuterium, a terphenyl group that is unsubstituted or substituted with a deuterium, a quaterphenyl group that is unsubstituted or substituted with a deuterium, a fluorenyl group that is unsubstituted or substituted with an alkyl group, a naphthyl group that is unsubstituted or substituted with a deuterium, a triphenylene group that is unsubstituted or substituted with a deuterium, a phenanthrene group that is unsubstituted or substituted with a deuterium, a chrysene group that is unsubstituted or substituted with a deuterium, a fluoranthene group that is unsubstituted or substituted with a deuterium, a pyrene group that is unsubstituted or substituted with a deuterium, a perylene group that is unsubstituted or substituted with a deuterium, a benzophenanthrene group that is unsubstituted or substituted with a deuterium, a benzotetraphene group that is unsubstituted or substituted with a deuterium, or a tetraphene group that is unsubstituted or substituted with a deuterium.

14. A heterocyclic compound of Chemical Formula 1:

[Chemical Formula 1]

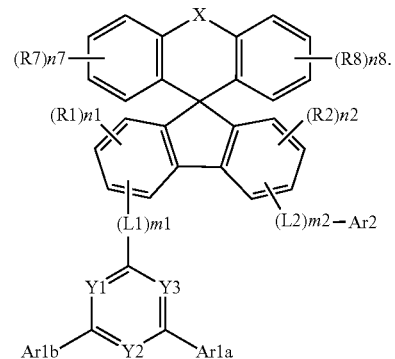

wherein, in Chemical Formula 1:
X is O or S;
Y1 to Y3 are the same as or different from each other, and each independently is N or CR, and at least two of Y1 to Y3 are N;
Ar1a and Ar1b are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

Ar2 is one selected from among the following structural formulae:

-continued

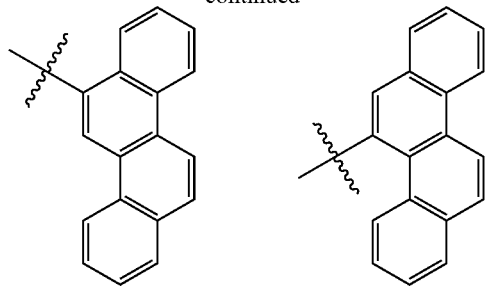

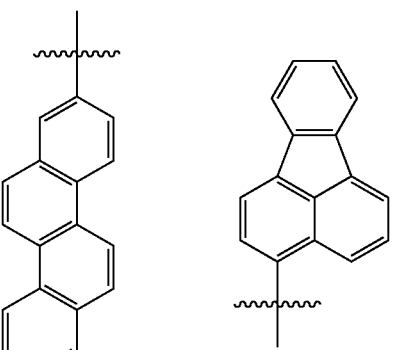

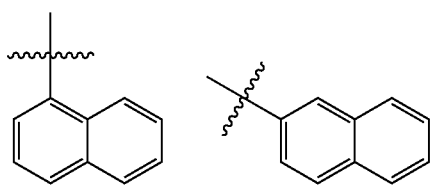

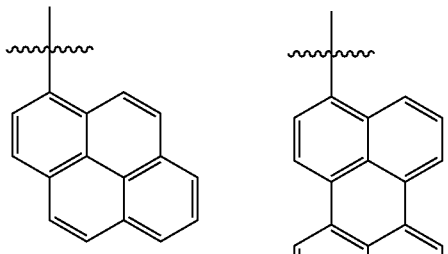

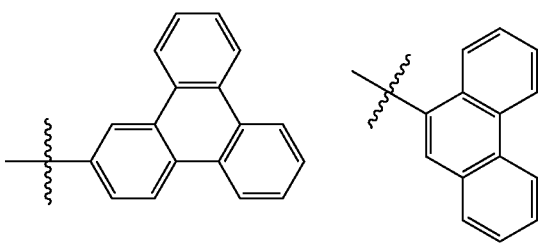

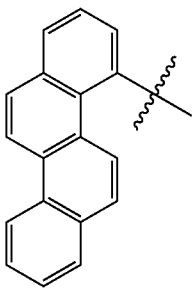
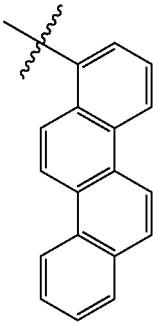

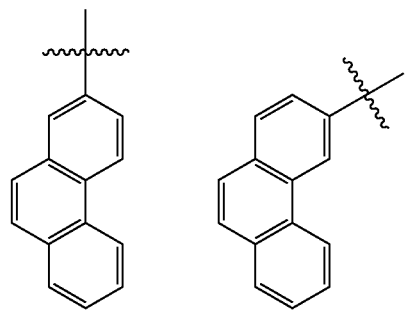

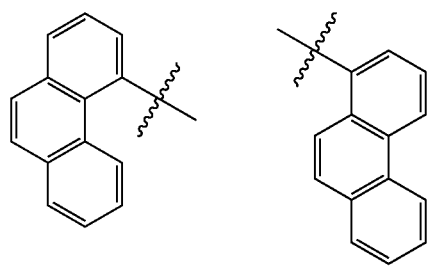
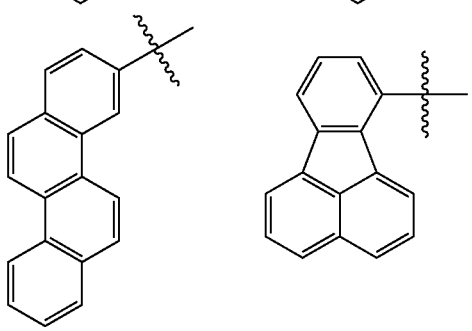

-continued

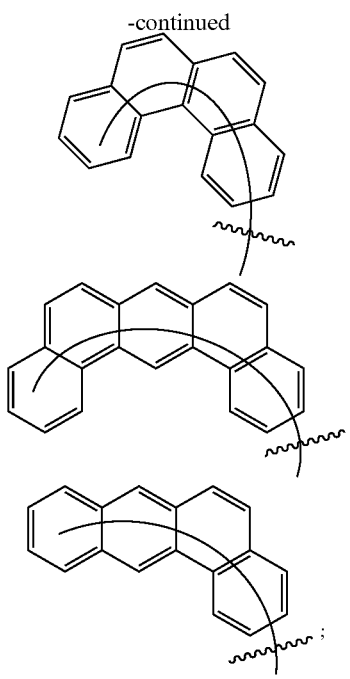

L1 is a direct bond;
L2 is a direct bond or a substituted or unsubstituted arylene group;
R, R1, R2, R7 and R8 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and
n1 and n2 are each independently an integer of 0 to 3, n7 and n8 are each independently an integer of 0 to 4, m1 is 1, and m2 is an integer of 1 or 2, and
when n1, n2, n7 and n8 are each an integer of 2 or greater, substituents in the parentheses are the same as or different from each other,
and when m2 is an integer of 2, substituents in the parentheses are the same as or different from each other.

15. An organic light emitting device comprising:
a first electrode;
a second electrode provided opposite to the first electrode; and
one or more organic material layers provided between the first electrode and the second electrode,
wherein one or more layers of the organic material layers include the heterocyclic compound of claim 14.

16. The organic light emitting device of claim 15, wherein the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound.

17. The organic light emitting device of claim 15, wherein:
the organic material layer includes a hole blocking layer, and the hole blocking layer includes the heterocyclic compound; or
the organic material layer includes an electron control layer, and the electron control layer includes the heterocyclic compound.

18. A heterocyclic compound of Chemical Formula 1:

[Chemical Formula 1]

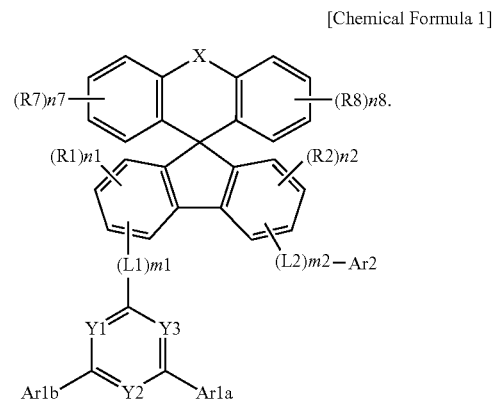

wherein, in Chemical Formula 1:
X is O or S;
Y1 to Y3 are the same as or different from each other, and each independently is N or CR, and at least two of Y1 to Y3 are N;
Ar1a and Ar1b are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

Ar2 is Chemical Formula 2:

[Chemical Formula 2]

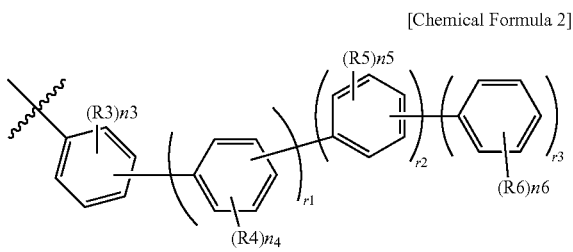

wherein in Chemical Formula 2:
R3 to R6 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

n3 to n5 are each independently an integer of 0 to 4, n6 is an integer of 0 to 5, and when n3 to n6 are each an integer of 2 or greater, substituents in the parentheses are the same as or different from each other;

r1 to r3 are each independently an integer of 0 to 5, and when r1 to r3 are each an integer of 2 or greater, structures in the parentheses are the same as or different from each other; and n3+r1=5, n4+r2=5 and n5+r3=5;

L1 is a direct bond;

L2 is a direct bond or a substituted or unsubstituted arylene group;

R, R1, R2, R7 and R8 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and n1 and n2 are each independently an integer of 0 to 3, n7 and n8 are each independently an integer of 0 to 4, m1 is 1, and m2 is an integer of 1 or 2, and when n1, n2, n7 and n8 are each an integer of 2 or greater, substituents in the parentheses are the same as or different from each other, and when m2 is an integer of 2, substituents in the parentheses are the same as or different from each other.

19. The heterocyclic compound of claim 18, wherein Chemical Formula 2 is one selected from among the following Chemical Formulae 2-1 to 2-6:

[Chemical Formula 2-1]

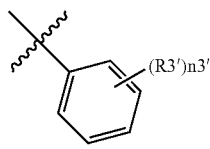

[Chemical Formula 2-2]

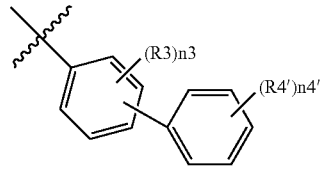

[Chemical Formula 2-3]

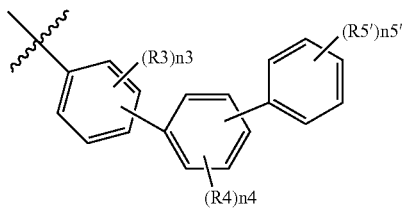

[Chemical Formula 2-4]

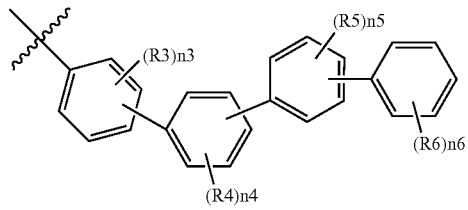

[Chemical Formula 2-5]

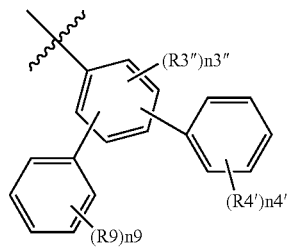

[Chemical Formula 2-6]

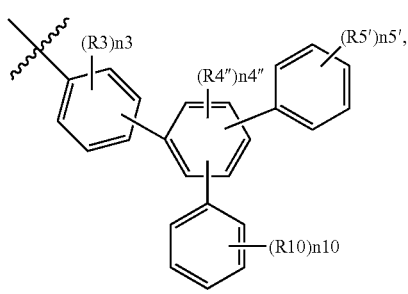

wherein in Chemical Formulae 2-1 to 2-6:
R3' to R5' have the same definitions as in R3 to R5 of Chemical Formula 2, respectively;
R9 and R10 have the same definitions as in R4 and R5 of Chemical Formula 2, respectively;
n3' to n5', n9 and n10 are each an integer of 0 to 5, and n3" and n4" are each an integer of 0 to 3;
when n3' to n5', n3", n4", n9 and n10 are each an integer of 2 or greater, substituents in the parentheses are the same as or different from each other; and
the remaining substituents have the same definitions as in Chemical Formula 2.

20. The heterocyclic compound of claim 18, wherein R3 to R6 are each hydrogen.

21. An organic light emitting device comprising:
a first electrode;
a second electrode provided opposite to the first electrode; and
one or more organic material layers provided between the first electrode and the second electrode,
wherein one or more layers of the organic material layers include the heterocyclic compound of claim 18.

22. The organic light emitting device of claim 21, wherein the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound.

23. The organic light emitting device of claim 21, wherein:
the organic material layer includes a hole blocking layer, and the hole blocking layer includes the heterocyclic compound; or
the organic material layer includes an electron control layer, and the electron control layer includes the heterocyclic compound.

* * * * *